(12) United States Patent  
Mascitti

(10) Patent No.: US 9,439,901 B2
(45) Date of Patent: Sep. 13, 2016

(54) DIOXA-BICYCLO[3.2.1]OCTANE-2,3,4-TRIOL DERIVATIVES

(71) Applicant: Pfizer Inc., New York, NY (US)

(72) Inventor: Vincent Mascitti, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/535,556

(22) Filed: Nov. 7, 2014

(65) Prior Publication Data

US 2015/0065512 A1     Mar. 5, 2015

Related U.S. Application Data

(60) Division of application No. 13/796,339, filed on Mar. 12, 2013, now abandoned, which is a continuation of application No. 13/498,702, filed as application No. PCT/IB2010/054775 on Oct. 21, 2010, now Pat. No. 8,669,380.

(60) Provisional application No. 61/372,938, filed on Aug. 12, 2010, provisional application No. 61/257,140, filed on Nov. 2, 2009.

(51) Int. Cl.
| | | |
|---|---|---|
| A61K 31/357 | (2006.01) | |
| A61K 31/155 | (2006.01) | |
| C07D 493/08 | (2006.01) | |
| A61K 31/4985 | (2006.01) | |
| A61K 45/06 | (2006.01) | |

(52) U.S. Cl.
CPC ......... *A61K 31/4985* (2013.01); *A61K 31/155* (2013.01); *A61K 31/357* (2013.01); *A61K 45/06* (2013.01); *C07D 493/08* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 4,598,089 A | 7/1986 | Hadvary et al. |
| 4,929,629 A | 5/1990 | Jeffrey |
| 5,047,518 A | 9/1991 | Furneaux et al. |
| 5,591,836 A | 1/1997 | Mazur et al. |
| 5,624,941 A | 4/1997 | Barth et al. |
| 6,069,238 A | 5/2000 | Hitchcock et al. |
| 6,414,126 B1 | 7/2002 | Ellsworth et al. |
| 6,486,299 B1 | 11/2002 | Shimkets |
| 6,515,117 B2 | 2/2003 | Ellsworth et al. |
| 6,555,519 B2 | 4/2003 | Washburn |
| 6,627,611 B2 | 9/2003 | Tomiyama et al. |
| 6,683,056 B2 | 1/2004 | Washburn et al. |
| 6,774,112 B2 | 8/2004 | Gougoutas |
| 6,815,428 B2 | 11/2004 | Ohsumi et al. |
| 6,838,442 B2 | 1/2005 | Bussolari et al. |
| 6,872,706 B2 | 3/2005 | Fujikura et al. |
| 6,908,905 B2 | 6/2005 | Ohsumi et al. |
| 6,936,590 B2 | 8/2005 | Washburn et al. |
| 6,972,283 B2 | 12/2005 | Fujikura et al. |
| 7,045,665 B2 | 5/2006 | Fujikura et al. |
| 7,053,060 B2 | 5/2006 | Fujikura et al. |
| 7,056,892 B2 | 6/2006 | Fujikura et al. |
| 7,084,123 B2 | 8/2006 | Fujikura et al. |
| 7,087,579 B2 | 8/2006 | Nishimura et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |
| 7,217,697 B2 | 5/2007 | Shiohara et al. |
| 7,247,705 B2 | 7/2007 | Iwamoto et al. |
| 7,250,522 B2 | 7/2007 | Sato et al. |

(Continued)

FOREIGN PATENT DOCUMENTS

| | | |
|---|---|---|
| CA | 2572149 | 1/2006 |
| CA | 2666375 | 9/2007 |

(Continued)

OTHER PUBLICATIONS

Ehrenkranz, et al., "Phlorizin: a review", Diabetes/Metabolism Research and Reviews, vol. 21(1), pp. 31-38 (2005).

(Continued)

*Primary Examiner* — San-Ming Hui
*Assistant Examiner* — Andrew Lee
(74) *Attorney, Agent, or Firm* — Lisa A. Samuels

(57) ABSTRACT

Compounds of Formula (A) and (B) are described herein and the uses thereof for the treatment of diseases, conditions and/or disorders mediated by sodium-glucose transporter inhibitors (in particular, SGLT2 inhibitors).

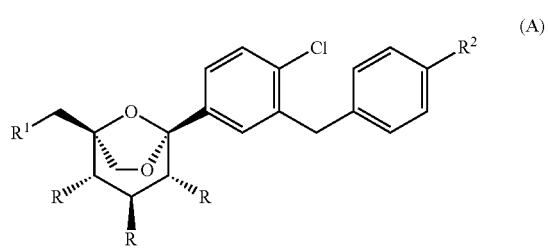

(A)

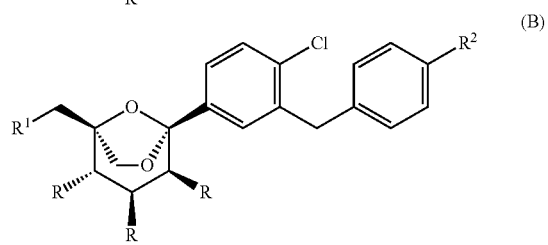

(B)

2 Claims, No Drawings

(56) References Cited

U.S. PATENT DOCUMENTS

| | | |
|---|---|---|
| 7,271,153 B2 | 9/2007 | Nishimura et al. |
| 7,288,528 B2 | 10/2007 | Frick et al. |
| 7,294,618 B2 | 11/2007 | Fushimi et al. |
| 7,371,730 B2 | 5/2008 | Iyobe et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,113 B2 | 5/2008 | Fishimi et al. |
| 7,375,213 B2 | 5/2008 | Deshpande et al. |
| 7,393,836 B2 | 7/2008 | Eckhardt et al. |
| 7,414,072 B2 | 8/2008 | Sato et al. |
| 7,417,032 B2 | 8/2008 | Eckhardt et al. |
| 7,419,959 B2 | 9/2008 | Eckhardt et al. |
| 7,439,232 B2 | 10/2008 | Kakinuma et al. |
| 7,541,341 B2 | 6/2009 | Fushimi et al. |
| 7,560,230 B2 | 7/2009 | Tidmarsh |
| 7,566,699 B2 | 7/2009 | Fushimi et al. |
| 7,576,064 B2 | 8/2009 | Kikuchi et al. |
| 7,579,449 B2 | 8/2009 | Eckhardt et al. |
| 7,589,193 B2 | 9/2009 | Washburn et al. |
| 7,635,684 B2 | 12/2009 | Fushimi et al. |
| 7,655,633 B2 | 2/2010 | Fujikura et al. |
| 7,687,469 B2 | 3/2010 | Eckhardt et al. |
| 8,080,580 B2 * | 12/2011 | Mascitti et al. ............... 514/456 |
| 2002/0034799 A1 | 3/2002 | Donoho et al. |
| 2002/0081678 A1 | 6/2002 | Merkulov et al. |
| 2002/0111315 A1 | 8/2002 | Washburn et al. |
| 2003/0022309 A1 | 1/2003 | Merkulov et al. |
| 2003/0045553 A1 | 3/2003 | Bussolari et al. |
| 2003/0054453 A1 | 3/2003 | Curtis et al. |
| 2003/0195235 A1 | 10/2003 | Bussolari et al. |
| 2003/0199557 A1 | 10/2003 | Bussolari et al. |
| 2004/0063170 A1 | 4/2004 | Fujikura et al. |
| 2004/0259819 A1 | 12/2004 | Frick et al. |
| 2005/0089955 A1 | 4/2005 | Gong et al. |
| 2005/0186613 A1 | 8/2005 | Merkulov et al. |
| 2005/0233988 A1 | 10/2005 | Nomura et al. |
| 2006/0019948 A1 | 1/2006 | Eckhardt et al. |
| 2006/0035841 A1 | 2/2006 | Eckhardt et al. |
| 2006/0035844 A1 | 2/2006 | Ito et al. |
| 2006/0063711 A1 | 3/2006 | Iwamoto et al. |
| 2006/0121465 A1 | 6/2006 | Lang et al. |
| 2006/0122126 A1 | 6/2006 | Imamura et al. |
| 2006/0189548 A1 | 8/2006 | Himmelsbach et al. |
| 2007/0004648 A1 | 1/2007 | Himmelsbach et al. |
| 2007/0009615 A1 | 1/2007 | Zhong |
| 2007/0027092 A1 | 2/2007 | Himmelsbach et al. |
| 2007/0036874 A1 | 2/2007 | Zhong |
| 2007/0049537 A1 | 3/2007 | Eckhardt et al. |
| 2007/0054867 A1 | 3/2007 | Eckhardt et al. |
| 2007/0059356 A1 | 3/2007 | Almarsson et al. |
| 2007/0099237 A1 | 5/2007 | Rodriguez-Hornedo |
| 2007/0185197 A1 | 8/2007 | Fujikura et al. |
| 2007/0197449 A1 | 8/2007 | Fushimi et al. |
| 2007/0197450 A1 | 8/2007 | Fushimi et al. |
| 2007/0197623 A1 | 8/2007 | Brummerhop et al. |
| 2007/0259821 A1 | 11/2007 | Eckhardt et al. |
| 2007/0275907 A1 | 11/2007 | Chen et al. |
| 2007/0293690 A1 | 12/2007 | Tomiyama et al. |
| 2008/0045466 A1 | 2/2008 | Katsuno et al. |
| 2008/0096802 A1 | 4/2008 | Bussolari et al. |
| 2008/0132563 A1 | 6/2008 | Kikinuma et al. |
| 2008/0139484 A1 | 6/2008 | Teranishi et al. |
| 2008/0234367 A1 | 9/2008 | Washburn et al. |
| 2008/0318874 A1 | 12/2008 | Matsuoka et al. |
| 2008/0319047 A1 | 12/2008 | Matsuoka et al. |
| 2009/0030006 A1 | 1/2009 | Kobayashi et al. |
| 2009/0054356 A1 | 2/2009 | Fushimi et al. |
| 2009/0074738 A1 | 3/2009 | Yonekubo et al. |
| 2009/0075864 A1 | 3/2009 | Bussolari et al. |
| 2009/0137499 A1 | 5/2009 | Honda et al. |
| 2009/0143316 A1 | 6/2009 | Imamura et al. |
| 2009/0182039 A1 | 7/2009 | Imamura et al. |
| 2009/0214477 A1 | 8/2009 | Betz et al. |
| 2010/0004465 A1 | 1/2010 | Kakinuma et al. |
| 2010/0093744 A1 | 4/2010 | Sato |

FOREIGN PATENT DOCUMENTS

| | | |
|---|---|---|
| CA | 2655780 | 12/2007 |
| DE | 3212682 | 10/1982 |
| DE | 10006887 | 9/2001 |
| EP | 129748 | 9/1987 |
| EP | 0341062 | 11/1989 |
| EP | 576357 | 3/1997 |
| EP | 0850948 | 1/1998 |
| EP | 1609798 | 12/2005 |
| EP | 1609799 | 12/2005 |
| EP | 1852439 | 7/2007 |
| EP | 2048152 | 4/2009 |
| EP | 2048153 | 4/2009 |
| JP | 2003012686 | 1/2003 |
| JP | 2004196788 | 7/2004 |
| JP | 2004359630 | 12/2004 |
| JP | 2005247834 | 9/2005 |
| JP | 2006117651 | 5/2006 |
| JP | 2008050353 | 3/2008 |
| WO | 9109537 | 7/1991 |
| WO | 9307167 | 4/1993 |
| WO | 9841648 | 9/1998 |
| WO | 0157214 | 8/2001 |
| WO | 03011880 | 2/2003 |
| WO | 03020737 | 3/2003 |
| WO | 03055914 | 7/2003 |
| WO | 03056005 | 7/2003 |
| WO | 03056329 | 7/2003 |
| WO | 2004019958 | 3/2004 |
| WO | 2004099230 | 11/2004 |
| WO | 2004106352 | 12/2004 |
| WO | 2005011592 | 2/2005 |
| WO | 2005012242 | 2/2005 |
| WO | 2005012243 | 2/2005 |
| WO | 2005012318 | 2/2005 |
| WO | 2005012321 | 2/2005 |
| WO | 2005012326 | 2/2005 |
| WO | 2005095372 | 10/2005 |
| WO | 2005095373 | 10/2005 |
| WO | 2005100998 | 10/2005 |
| WO | 2006062224 | 6/2006 |
| WO | 2006090577 | 8/2006 |
| WO | 2006117359 | 9/2006 |
| WO | 2006117360 | 9/2006 |
| WO | 2006108842 | 10/2006 |
| WO | 2006115137 | 11/2006 |
| WO | 2006120208 | 11/2006 |
| WO | 2007000445 | 1/2007 |
| WO | 2007014895 | 2/2007 |
| WO | 2007031548 | 3/2007 |
| WO | 2007126117 | 8/2007 |
| WO | 2007128480 | 11/2007 |
| WO | 2007129668 | 11/2007 |
| WO | 2007136116 | 11/2007 |
| WO | 2007140191 | 12/2007 |
| WO | 2008002824 | 1/2008 |
| WO | 2008013280 | 1/2008 |
| WO | 2008013321 | 1/2008 |
| WO | 2008013322 | 1/2008 |
| WO | 2008020011 | 2/2008 |
| WO | 2008034859 | 3/2008 |
| WO | 2008042688 | 4/2008 |
| WO | 2008049923 | 5/2008 |
| WO | 2008055870 | 5/2008 |
| WO | 2008055940 | 5/2008 |
| WO | 2008109591 | 9/2008 |
| WO | 2008115574 | 9/2008 |
| WO | 2009014970 | 1/2009 |
| WO | 2009022010 | 2/2009 |

(56) References Cited

FOREIGN PATENT DOCUMENTS

| WO | 2009026537 | 2/2009 |
|---|---|---|
| WO | 2009091082 | 7/2009 |
| WO | 2010023594 | 3/2010 |

OTHER PUBLICATIONS

Mancuso, et al., "Activated Dimethyl Sulfoxide: Useful Reagents for Synthesis", Synthesis, vol. 1981(3); pp. 165-185 (1981).
Meng, et al., "Discovery of Dapagliflozin: A Potent, Selective Renal Sodium-Dependent Glucose Cotransporter 2 (SGLT2) Inhibitor for the Treatment of Type 2 Diabetes", Journal of Medicinal Chemistry, vol. 51(5), pp. 1145-1149 (2008).
Fujimori, et al., "Remogliflozin Etabonate, in a Novel Category of Selective Low-Affinity Sodium Glucose Cotransporter (SGLT2) Inhibitors, Exhibits Antidiabetic Efficacy in Rodent Models", The Journal of Pharmacology and Experimental Therapeutics, vol. 327(1), pp. 268-276 (2008).
Lee, et al., "The High Affinity of Na+/Glucose Cotransporter", The Journal of Biological Chemistry, vol. 269(16), pp. 12032-12039 (1994).
Chasis, et al., "The Action of Phlorizin on the Execretion of Glucose, Xylose, Sucrose, Creatinine and Urea by Man", Journal of Clinical Investigation, vol. 12(6), pp. 1083-1090 (1933).
Idris, et al., "Sodium-glucose co-transporter-2 inhibitors: an emerging new class of oral antidiabetic drug", Diabetes, Obesity and Metabolism, vol. 11(2), pp. 79-88 (2009).
Kanai, et al., "The Human Kidney Low Affinity Na+/glucose cotransporter SGLT2: Delineation of the Major Renal Reabsorptive Mechanism for D-Glucose", Journal of Clinical Investigation, vol. 93(1), pp. 397-404 (1994).
Takagaki, et al. "Glucose to Value-added Chemicals: Anhydroglucose Formation by Selective Dehydration over Solid Acid Catalysts", Chemistry Letters, vol. 38(7), pp. 650-651 (2009).
Goodwin, et al., "Novel L-Xylose Derivatives as Selective Sodium-Dependent Glucose Cotransporter 2 (SGLT2) Inhibitors for the Treatment of Type 2 Diabetes", Journal of Medicinal Chemistry, vol. 52(20), pp. 6201-6204 (2009).
Capon, "Mechanism in Carbohydrate Chemistry", Chemical Reviews, vol. 69(4), pp. 407-498 (1969).
Basha, et al., "A Mild, General Method for Conversion of Esters to Amides", Tetrahedron Letters, vol. 18(48), pp. 4171-4174 (1977).
Witczak, et al., "A Convenient Synthesis of the (+) Enantiomer of Levoglucosenone and its 5-Hydroxymethyl Analog", Synlett, vol. 1996(1), pp. 108-110 (1996).
Mazur, et al., "Chemoenzymic Approaches to the Preparation of 5-C-(Hydroxymethyl)hexoses", Journal of Organic Chemistry, vol. 62(13), pp. 4471-4475 (1997).
Siebum, et al., "Galactose oxidase and alcohol oxidase: Scope and limitations for the enzymatic synthesis of aldehydes", Journal of Molecular Catalysis B: Enzymatic, vol. 41, pp. 141-145 (2006).
Angelin, et al., "Direct, Mild and Selective Synthesis of Unprotected Dialdo-Glycosides", European Journal of Organic Chemistry, vol. 2006(19), pp. 4323-4326 (2006).
Deshpande, et al., "Remarkable B-Selectivity in the Synthesis of B-1-C-arylglucosides: Stereoselective Reduction of Acetyl-Protected Methyl 1-C-Arylglucosides without Acetoxy-Group Participation", Journal of Organic Chemistry, vol. 72(25), pp. 9746-9749 (2007).
Czernecki, et al., "C-Glycosides. 9. Sterospecific Synthesis of C-Glycosidic Spiroketal of the Papulacandins", Journal of Organic Chemistry, vol. 56(22), pp. 6289-6292 (1991).
Barrett, et al., "Total Synthesis of the Antifungal Agent Papulacandin D", J. Chem. Soc., Chem. Commun., Issue 11, pp. 1147-1148 (1995).
Hu, et al., "O-Spiro C-aryl glucosides as novel sodium-dependent glucose co-transporter 2 (SGLT2) inhibitors", Bioorganic & Medicinal Chemistry Letters, vol. 19, pp. 5632-5635 (2009).

Borghese, et al., "Inhibitors of Sodium/Glucose Cotransport", Drugs of the Future, vol. 34(4), pp. 297-305 (2009).
Handlon, "Sodium glucose co-transporter 2 (SGLT2) inhibitors as potential antidiabetic agents", Expert Opinion on Therapeutic Patents, vol. 15(11), pp. 1531-1540 (2005).
Asano, et al., "SGLT as a therapeutic target", Drugs of the Future, vol. 29(5), pp. 461-466 (2004).
Ellsworth, et al., "Aglycone exploration of C-arylglucoside inhibitors of renal sodium-dependent glucose transporter SGLT2", Bioorganic & Medicinal Chemistry Letters, vol. 18(17), pp. 4770-4773 (2008).
McGinnis, et al., Actual Causes of Death in the United States, JAMA, vol. 270(18), pp. 2207-2212 (1993).
Hanashima, et al., "Synthesis of Sulfoquinovosylacylglycerols, Inhibitors of Eukaryotic DNA Polymerase a and B", Bioorganic & Medicinal Chemistry, vol. 9(2), pp. 367-376 (2001).
Gent, et al., "The Allyl Ether as a Protecting Froup in Carbohydrate Chemistry. Part VI. The Allyl Ether as a 'Temporary' Protecting Group in Oligosaccharide Synthesis", Journal of the Chemical Society Perkin Transaction 1, vol. 1974, pp. 1835-1839 (1974).
Wessel, "Use of Trifluoromethanesulfonic Acid in Fischer Glycosylations", J. Carbohydrate Chemistry, vol. 7(1), pp. 263-269 (1988).
Yuasa, et al., "A Practical Synthesis of 2,3,4,6-Tetra-0-acetyl-1-0-(2-propenyl)-B-D-glucopyranoside Using ZnCl2", Organic Process Research & Development, vol. 8(3), pp. 405-407 (2004).
Omura, et al., "Oxidation of Alcohols by 'Activated' Dimethyl Sulfoxide. A Preparative, Steric and Mechanistic Study", Tetrahedron, vol. 34(11), pp. 1651-1660 (1978).
Ozane, et al., "A Stabilized Formulation of IBX (SIBX) for Safe Oxidation Reactions Including a New Oxidative Demethylation of Phenolic Methyl Aryl Ethers", Organic Letters, vol. 5(16), pp. 2903-2906 (2003).
Schaffer, Branched-chain Higher Sugars. III. A 4-C-(Hydroxymethyl)-pentose, Journal of the American Chemical Society, vol. 81(20), pp. 5452-5454 (1959).
Amigues, et al., "Synthesis of cyclophospho-glucoses and glucitols" Tetrahedron, vol. 63(40), pp. 10042-10053 (2007).
Nahm, et al., "N-Methoxy-N-Methylamides as Effective Acylating Agents", Tetrahedron Letters, vol. 22(39), pp. 3815-3818 (1981).
Kornblum, et al., "A New and Selective Method of Oxidation, the Conversion of Alkyl Halides and Alkyl Tosylates to Aldehydes", Journal of the American Chemical Society, vol. 81(15), pp. 4113-4114 (1959).
Zhang, et al., PTP1B as a drug target: recent developments in PTP1B inhibitor discovery, Drug Discovery Today, vol. 12(9-10), pp. 373-381 (2007).
Fabian, "Cambridge Structural Database Analysis of Molecular Complementarity in Cocrystals", Crystal Growth & Design, vol. 9(3), pp. 1436-1443 (2009).
Lv, et al., "Exploration of 0-spiroketal C-arylglucosides as novel and selective renal sodium-dependent glucose co-transporter 2 (SGLT2) inhibitors", Bioorganic & Medicinal Chemistry Letters, vol. 19(24), pp. 6877-6881 (2009).
Washburn, "Evolution of sodium glucose co-transporter 2 inhibitors as anti-diabetic agents", Expert Opinion on Therapeutic Patents, vol. 19(11), pp. 1485-1499 (2009).
Washburn, "Development of the Renal Glucose Reabsorption Inhibitors: A New Mechanism for the Pharmacotherapy of Diabetes Mellitus Type 2", Journal of Medicinal Chemistry, vol. 52(7), pp. 1785-1794 (2009).
OECD Guideline for the Testing of Chemicals Draft Proposal for a New Guideline 487: In Vitro Mammalian Cell Micronucleus Test (MNvit), Draft Test Guideline Dec. 13, 2007 (Version 3).
OECD Guideline for the Testing of Chemicals 473: In Vitro Mammalian Chromosome Aberration Test, Adopted: Jul. 21, 1997.
OECD Guideline for Testing of Chemicals 471: Bacterial Reverse Mutation Test, Adopted: Jul. 21, 1997.
OECD Guideline for the Testing of Chemicals 474: Mammalian Erythrocyte Micronucleus Test, Adopted: Jul. 21, 1997.
Yamanoi, et al., "Trifluoromethanesulfonic Acid Efficiently Catalyzed the Intramolecular Glycosidation of 1-C-Alkyl-D-

(56) References Cited

OTHER PUBLICATIONS hexopyranoses to Form the Anhydroketopyranoses Having 6,8-Dioxabicyclo[3.2.1]octane Structures", Synlett, No. 19, pp. 2973-2977 (2005).

Isaji, "Sodium-glucose cotransporter inhibitors for diabetes", Current Opinion in Investigational Drugs, vol. 8(4), pp. 285-292 (2007).
Mascitti, et al., "Stereoselective Synthesis of a Dioxa-bicyclo[3.2.1]octane SGLT2 Inhibitor", Organic Letters, vol. 12 (13), pp. 2940-2943 (2010).

* cited by examiner

DIOXA-BICYCLO[3.2.1]OCTANE-2,3,4-TRIOL DERIVATIVES

CROSS REFERENCE TO RELATED APPLICATIONS

This application claims the benefit of priority from U.S. patent application Ser. No. 13/796,339 filed Mar. 12, 2013, which claims priority from U.S. patent application Ser. No. 13/498,702 issued as U.S. Pat. No. 8,669,380 on Mar. 11, 2014 which claims priority from U.S. Provisional Application Ser. No. 61/257,140 filed Nov. 2, 2009 and U.S. Provisional Application Ser. No. 61/372,938 filed Aug. 12, 2010,all of which are incorporated in their entireties for all purposes.

FIELD OF THE INVENTION

This invention relates to dioxa-bicyclo[3.2.1]octane-2,3,4-triol derivatives, pharmaceutical compositions and the uses thereof as sodium-glucose co-transporter (SGLT) inhibitors.

BACKGROUND

Obesity is a significant health problem due to its serious medical complications that include co-morbidities such as hypertension, insulin resistance, diabetes, coronary artery disease and heart failure (collectively referred to as Metabolic Syndrome). Obesity and its related co-morbidities continue to cause rising health issues in the developed world and are beginning to affect the developing world as well. The negative health consequences of obesity make it the second leading cause of preventable death in the United States and impart a significant economic and psychosocial effect on society. See, McGinnis M, Foege W H., "Actual Causes of Death in the United States," *JAMA,* 270, 2207-12 (1993). There is a need to identify and develop new medications that treat and/or prevent obesity and its associated co-morbidities, in particular Type II (Type 2) diabetes.

More recently, sodium-glucose co-transporter (SGLT) inhibitors, particularly SGLT2 inhibitors, have been shown to block the reabsorption of glucose from the renal filtrate in the glomerulus thereby inducing glucose excretion in the urine. As excess glucose is excreted, there is a decrease in blood glucose level, decreased hepatic storage of glucose, decreased insulin secretion and, subsequently, decreased carbohydrate conversion to fat and, ultimately, reduced accumulated fat. Selective inhibition of SGLT2 is expected to normalize plasma glucose by enhancing glucose excretion. Consequently, SGLT2 inhibitors provide an attractive means for the improvement of diabetic conditions without increasing body weight or the risk of hypoglycemia. See, Isaji, M., *Current Opinion Investigational Drugs,* 8(4), 285-292 (2007). For a general review of SGLT as a therapeutic target, see also Asano, T., et al., *Drugs of the Future,* 29(5), 461-466 (2004).

Representative examples of glycosides that have been shown to be useful for the treatment of NIDDM and obesity can be found in the following disclosures: U.S. Pat. Nos. 6,515,117; 6,414,126; 7,101,856; 7,169,761; and 7,202,350; U.S. Publication Nos.: US2002/0111315; US2002/0137903; US2004/0138439; US2005/0233988; US2006/0025349; US2006/0035841; and US2006/0632722; and PCT Publication Nos.: WO01/027128; WO02/044192; WO02/088157; WO03/099836; WO04/087727; WO05/021566; WO05/085267; WO06/008038; WO06/002912; WO06/062224; WO07/000445; WO07/093610; and WO08/002824.

Certain glycosides are genotoxic and impact a cell's genetic material such that they may be potentially mutagenic or carcinogenic. Genotoxic materials may be detected using standard assays such as the In Vitro Mammalian Cell Micronucleus Test (MNvit), Organization for Economic Co-Operation and Development (OECD) Draft Test Guideline (Draft TG) 487 (2007); In vitro Mammalian Chromosomal Aberration Test, OECD TG 473 (1997); Bacterial Reverse Mutation Test, OECD TG 471 (1997); Mammalian Erythrocyte Micronucleus Test, OECD TG 474 (1997); or the like. Consequently, there still exists a need for a more effective and safe therapeutic treatment and/or prevention of obesity and its associated co-morbidities, in particular, Type 2 diabetes and related disorders.

SUMMARY

One aspect of this invention includes compounds of Formula (A) or Formula (B)

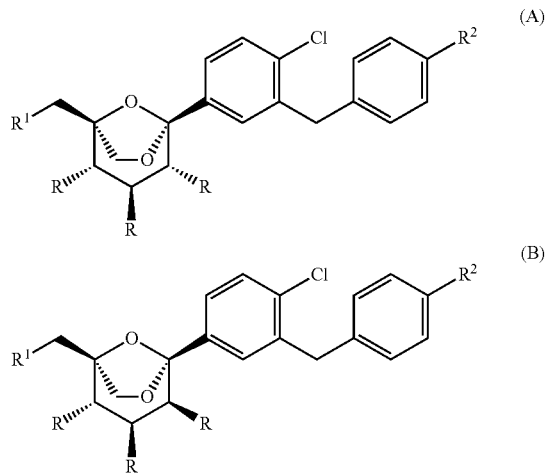

wherein
R is —OH or, when $R^1$ is —O—C(O)—($C_1$-$C_4$)alkyl or —O—C(O)-aryl, R is the same as $R^1$ or —OH;
$R^1$ is —OH, F, Cl, —O—C(O)—($C_1$-$C_4$)alkyl, —O—C(O)-aryl, —O—C(O)—O—($C_1$-$C_4$)alkyl or —O—C(O)—O-aryl; and
$R^2$ is —OH, —O—($C_1$-$C_4$)alkyl or —O—$CH_2$—$CH_2$—O—$R^{2a}$;
with the proviso that when R is —OH and $R^1$ is —OH, $R^2$ is —OH or —O—$CH_2$—$CH_2$—O—$R^{2a}$;
$R^{2a}$ is H, —C(O)—($C_1$-$C_4$)alkyl, —C(O)-aryl, —C(O)—O—($C_1$-$C_4$)alkyl or —C(O)—O-aryl;
and pharmaceutically acceptable salts thereof.

Another aspect of this invention is a pharmaceutical composition that comprises (1) a compound of this invention, and (2) a pharmaceutically acceptable excipient, diluent, or carrier. Preferably, the composition comprises a therapeutically effective amount of a compound of this invention. The composition may also contain at least one additional pharmaceutical agent. Preferred agents include anti-obesity agents and/or anti-diabetic agents.

In yet another aspect of this invention, a method for treating a disease, disorder, or condition modulated by SGLT2 inhibition in animals is provided that includes the step of administering to an animal (preferably, a human) in need of such treatment a therapeutically effective amount of a compound of this invention (or a pharmaceutical composition thereof). Diseases, conditions, and/or disorders modulated by SGLT2 inhibition include, e.g., Type II diabetes, diabetic nephropathy, insulin resistance syndrome, hyperglycemia, hyperinsulinemia, hyperlipidemia, impaired glucose tolerance, obesity (including weight control or weight maintenance), hypertension, and reducing the level of blood glucose.

Compounds of this invention may be administered in combination with other pharmaceutical agents (in particular, anti-obesity and anti-diabetic agents described herein below). The combination therapy may be administered as (a) a single pharmaceutical composition which comprises a compound of this invention, at least one additional pharmaceutical agent described herein and a pharmaceutically acceptable excipient, diluent, or carrier; or (b) two separate pharmaceutical compositions comprising (i) a first composition comprising a compound of this invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

It is to be understood that both the foregoing summary and the following detailed description are exemplary and explanatory only and are not restrictive of the invention, as claimed.

DETAILED DESCRIPTION

This invention may be understood even more readily by reference to the following detailed description of exemplary embodiments of the invention and the examples included therein.

Before the compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting. The plural and singular should be treated as interchangeable, other than the indication of number.

As used herein, the term "alkyl" refers to a hydrocarbon radical of the general formula $C_nH_{2n+1}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neo-pentyl, 3,3-dimethylpropyl, hexyl, 2-methylpentyl, and the like). Similarly, the alkyl portion (i.e., alkyl moiety) of an alkoxy group has the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of listed substituents.

"Aryl" refers to an aromatic ring, such as benzene, phenyl, or naphthalene.

The phrase "therapeutically effective amount" means an amount of a compound of this invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refer to the inhibition of the sodium-glucose transporter (in particular, SGLT2) with compounds of this invention thereby partially or fully preventing glucose transport across the transporter.

The term "compounds of this invention" (unless specifically identified otherwise) refer to compounds of Formula (A), Formula (B) and all pure and mixed stereoisomers (including diastereoisomers and enantiomers), tautomers and isotopically labeled compounds. Hydrates and solvates of the compounds of this invention are considered compositions of this invention, wherein the compound is in association with water or solvent, respectively. The compounds may also exist in one or more crystalline states, i.e. as co-crystals, polymorphs, or they may exist as amorphous solids. All such forms are encompassed by the invention and the claims.

In one embodiment, the compound is a compound of Formula (A).

In another embodiment, $R^1$ is —OH.

In a further embodiment, $R^2$ is —OH.

In yet another embodiment, $R^2$ is —O—$CH_2CH_2OH$.

The compounds of this invention contain asymmetric or chiral centers, and, therefore, exist in different stereoisomeric forms. Unless specified otherwise, it is intended that all stereoisomeric forms of the compounds of this invention as well as mixtures thereof, including racemic mixtures, form part of this invention. In addition, this invention embraces all geometric and positional isomers. For example, if a compound of this invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization, distillation, sublimation. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of this invention may be atropisomers (e.g., substituted biaryls) and are considered as part of this invention. Enantiomers can also be separated by use of a chiral HPLC (high performance liquid chromatography) column.

It is also possible that the intermediates and compounds of this invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. The equilibrium between closed and opened form of some intermediates (and/or mixtures of intermediates) is reminiscent of the process of mutarotation involving aldoses, known by those skilled in the art.

This invention also embraces isotopically-labeled compounds which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of this invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of this invention can generally be prepared by following procedures substantially analogous to those disclosed in the Schemes and/or in the Examples herein below, by substituting an isotopically labeled reagent for a non-isotopically labeled reagent.

Some of the compounds of this invention may form salts with pharmaceutically acceptable cations or anions. All such salts are within the scope of this invention and they can be prepared by conventional methods such as by combining the acidic and basic entities, usually in a stoichiometric ratio, in either an aqueous, non-aqueous or partially aqueous medium, as appropriate. The salts are recovered by filtration, by precipitation with a non-solvent followed by filtration, by evaporation of the solvent, or, in the case of aqueous solutions, by lyophilization, as appropriate. The compounds are obtained in crystalline form according to procedures known in the art, such as by dissolution in an appropriate solvent(s) such as ethanol, hexanes or water/ethanol mixtures.

"Pharmaceutically acceptable salts" is intended to refer to either "pharmaceutically acceptable acid addition salts" or "pharmaceutically acceptable basic addition salts" depending upon actual structure of the compound. "Pharmaceutically acceptable acid addition salts" is intended to apply to any non-toxic organic or inorganic acid addition salt of the compounds of this invention or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents. "Pharmaceutically acceptable basic addition salts" is intended to apply to any non-toxic organic or inorganic basic addition salts of the compounds of this invention, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality of intermediates may be necessary. The need for such protection will vary depending on the nature of the remote functionality and the conditions of the preparation methods. A "hydroxy-protecting group" refers to a substituent of a hydroxy group that blocks or protects the hydroxy functionality. Suitable hydroxyl-protecting groups (O-Pg) include for example, allyl, acetyl (Ac), silyl (like trimethylsily (TMS) or tert-butyldimethylsilyl (TBS)), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl)ethoxymethyl (SEM), and the like (benzylidene for protection of 1,3-diols). The need for such protection is readily determined by one skilled in the art. For a general description of protecting groups and their use, see T. W. Greene, *Protective Groups in Organic Synthesis*, John Wiley & Sons, New York, 1991.

Scheme 1 outlines the general procedures one could use to provide compounds of the present invention.

Scheme 1
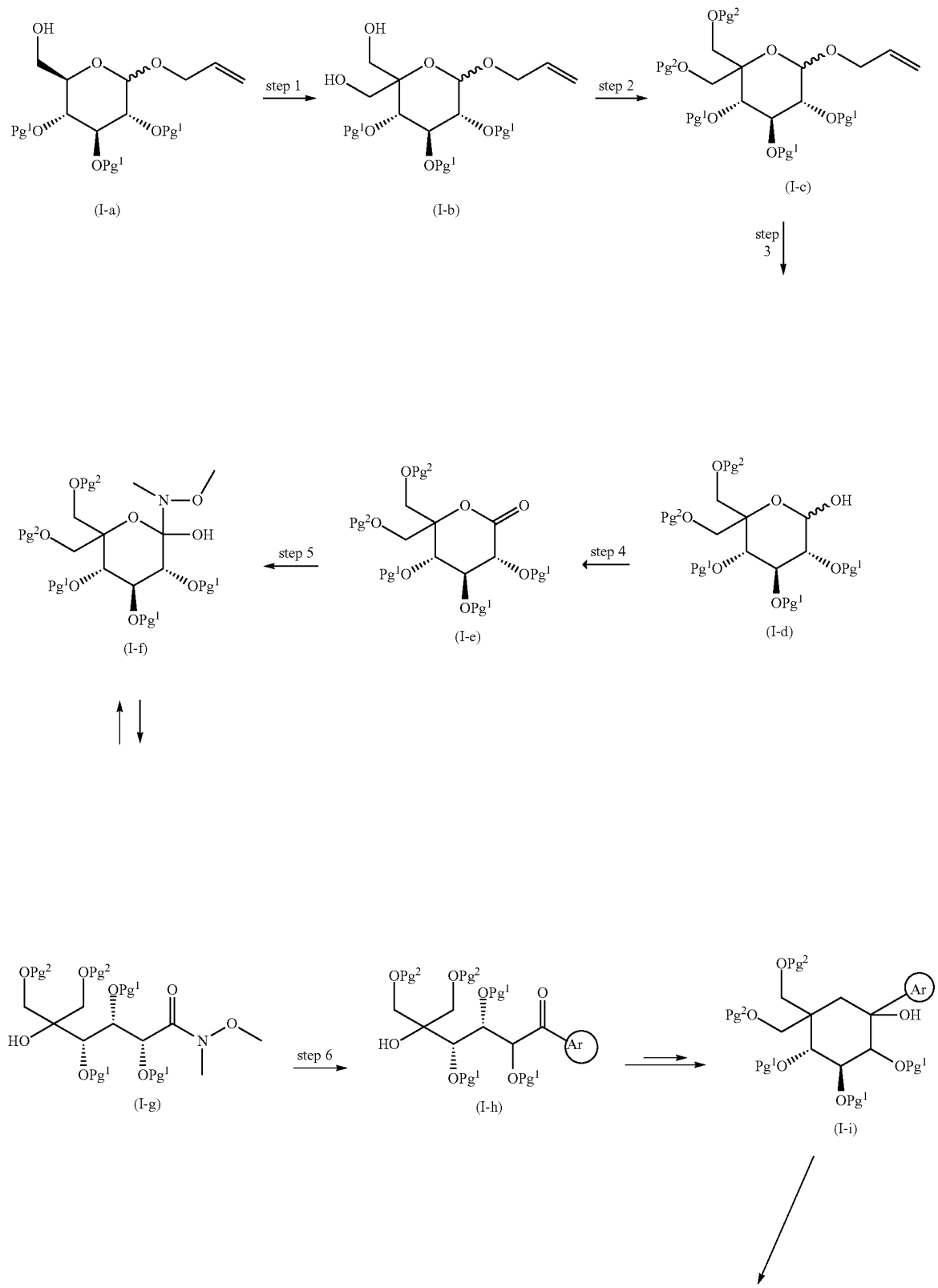

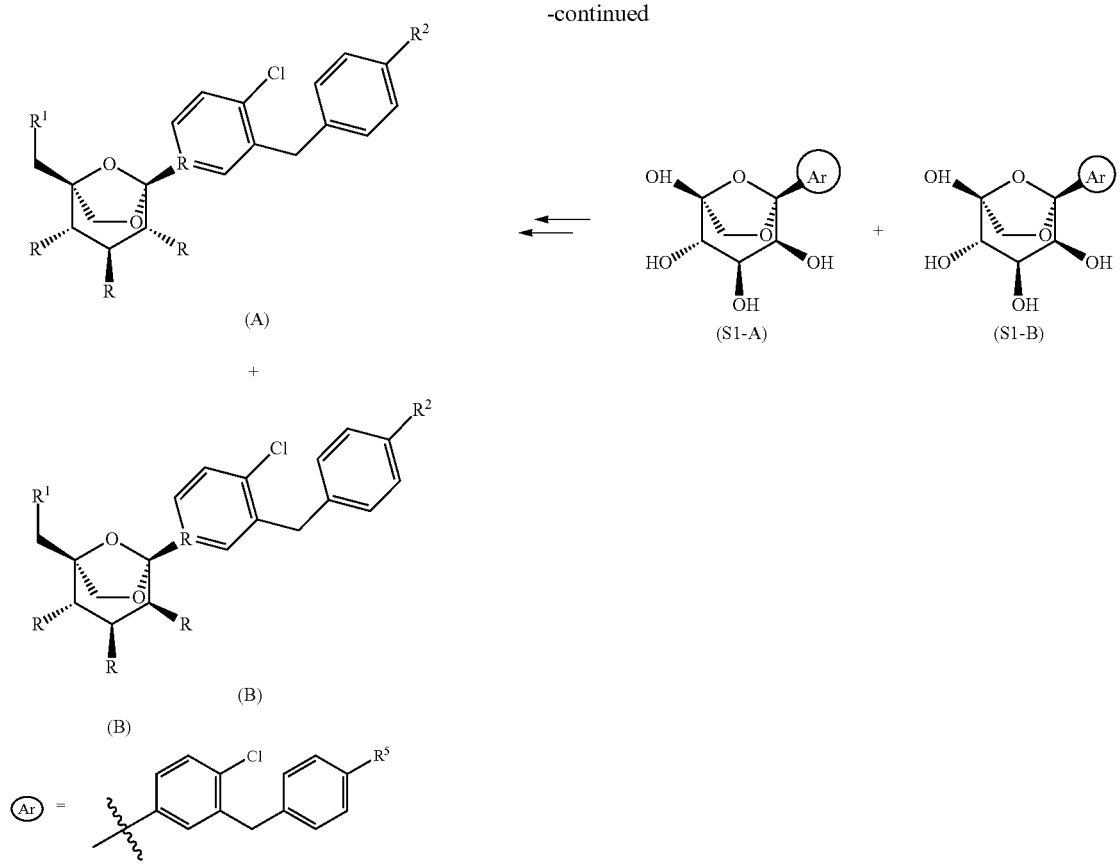

Allyl 2,3,4-tri-O-benzyl-D-glucopyranoside (I-a, where $Pg^1$ is a benzyl group) can be prepared by procedures described by Shinya Hanashima, et al., in *Bioorganic & Medicinal Chemistry*, 9, 367 (2001); Patricia A. Gent et al. in *Journal of the Chemical Society, Perkin* 1, 1835 (1974); Hans Peter Wessel in the *Journal of Carbohydrate Chemistry*, 7, 263, (1988); or Yoko Yuasa, et al., in *Organic Process Research & Development*, 8, 405-407 (2004). In step 1 of Scheme 1, the hydroxymethylene group can be introduced onto the glycoside by means of a Swern oxidation followed by treatment with formaldehyde in the presence of an alkali metal hydroxide (e.g., sodium hydroxide). This is referred to as an aldol-Cannizzaro reaction. The Swern oxidation is described by Kanji Omura and Daniel Swern in *Tetrahedron*, 34, 1651 (1978). Modifications of this process known to those of skill in the art may also be used. For example, other oxidants, like stabilized 2-iodoxybenzoic acid described by Ozanne, A. et al. in *Organic Letters*, 5, 2903 (2003), as well as other oxidants known by those skilled in the art can also be used. The aldol Cannizzaro sequence has been described by Robert Schaffer in the *Journal of The American Chemical Society*, 81, 5452 (1959) and Amigues, E. J., et al., in *Tetrahedron*, 63, 10042 (2007).

In step 2 of Scheme 1, protecting groups ($Pg^2$) can be added by treating intermediate (I-b) with the appropriate reagents and procedures for the particular protecting group desired. For example, p-methoxybenzyl (PMB) groups may be introduced by treatment of intermediate (I-b) with p-methoxybenzyl bromide or p-methoxybenzyl chloride in the presence of sodium hydride, potassium hydride, potassium tert-butoxide in a solvent like tetrahydrofuran, 1,2-dimethoxyethane or N,N-dimethylformamide (DMF). Conditions involving para-methoxybenzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used. Benzyl (Bn) groups may be introduced by treatment of intermediate (I-b) with benzyl bromide or benzyl chloride in the presence of sodium hydride, potassium hydride, potassium tert-butoxide in a solvent like tetrahydrofuran, 1,2-dimethoxyethane or N,N-dimethylformamide. Conditions involving benzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used.

In step 3 of Scheme 1, the allyl protection group is removed (e.g., by treatment with palladium chloride in methanol; cosolvent like dichloromethane may also be used; other conditions known by those skilled in the art could also be used, see T. W. Greene, *Protective Groups in Organic Synthesis*, John Wiley & Sons, New York, 1991) to form the lactol (I-d).

In step 4 of Scheme 1, oxidation of the unprotected hydroxyl group to an oxo group (e.g., Swern oxidation) then forms the lactone (I-e).

In step 5 of Scheme 1, the lactone (I-e) is reacted with N,O-dimethyl hydroxylamine hydrochloride to form the corresponding Weinreb amide which may exist in equilibrium in a closed/opened form. (I-f/I-g). The "Weinreb amide" (I-g) can be made using procedures well known to those of skill in the art. See, Nahm, S., and S. M. Weinreb, *Tetrahedron Letters*, 22 (39), 3815-1818 (1981). For example, intermediate (I-f/I-g) can be prepared from the commercially available N,O-dimethylhydroxylamine hydrochloride and an activating agent (e.g., trimethylaluminum).

In step 6 of Scheme 1, the arylbenzyl group (Ar, where $R^5$ is OEt, OTBS, or any suitably protected precursor to the claimed $R^2$) is introduced using the desired organometallic reagent (e.g., organo lithium compound (ArLi) or organomagnesium compound (ArMgX)) in tetrahydrofuran (THF) at a temperature ranging from about −78° C. to about 20° C. followed by hydrolysis (upon standing in protic conditions) to the corresponding lactol (I-i) which may be in equilibrium with the corresponding ketone (I-h). The bridged ketal motif found in (A) and (B) can be prepared by removing the protecting groups ($Pg^2$) using the appropriate reagents for the protecting groups employed. For example, the PMB protecting groups may be removed by treatment with trifluoroacetic acid in the presence of anisole and dichloromethane (DCM) at about 0° C. to about 23° C. (room temperature). The remaining protecting groups ($Pg^1$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce compounds (S1-A) and (S1-B). Depending on $R^5$, the compounds thus obtained can then be easily functionalized to other compounds of structures (A) and (B) from the present invention using well known protective and functional groups manipulation sequences known by those skilled in the art. See examples section for further details.

The compounds or intermediates of the present invention may be prepared as co-crystals using any suitable method. A representative scheme for preparing such co-crystals is described in Scheme 2.

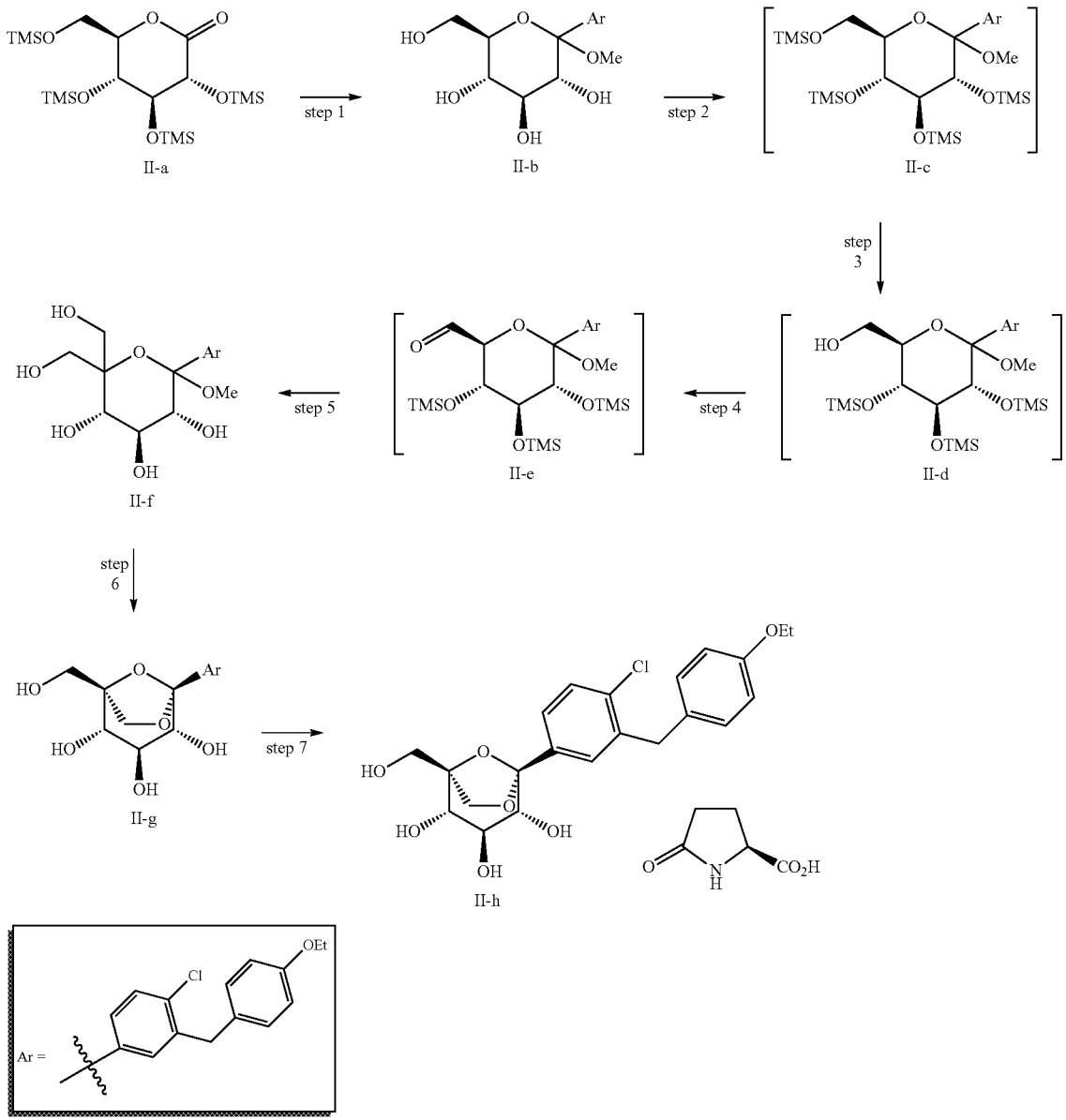

In Scheme 2, wherein Me is methyl and Et is ethyl, in step 1, 1-(5-bromo-2-chlorobenzyl)-4-ethoxybenzene is dissolved in 3:1, toluene: tetrahydrofuran followed by cooling the resulting solution to <−70° C. To this solution is added hexyllithium while maintaining the reaction at ≤−65° C. followed by stirring for 1 hour. (3R,4S,5R,6R)-3,4,5-tris(trimethylsilyloxy)-6-((trimethylsilyloxy)methyl)-tetrahydropyran-2-one (II-a) is dissolved in toluene and the resulting solution is cooled to −15° C. This solution is then added to the −70° C. aryllithium solution followed by stirring for 1 hour. A solution of methanesulfonic acid in methanol is then added followed by warming to room temperature and stirring for 16 to 24 hours. The reaction is deemed complete when the α-anomer level is ≤3%. The reaction is then basified by the addition of 5 M aqueous sodium hydroxide solution. The resulting salts are filtered off followed by concentration of the crude product solution. 2-methyltetrahydrofuran is added as a co-solvent and the organic phase is extracted twice with water. The organic phase is then concentrated to 4 volumes in toluene. This concentrate is then added to a 5:1, heptane:toluene solution causing precipitate to form. The solids are collected and dried under vacuum to afford a solid.

In step 2 of Scheme 2, to (II-b) in methylene chloride is added imidazole followed by cooling to 0° C. and then addition of trimethylsilylchloride to give the persilylated product. The reaction is warmed to room temperature and quenched by the addition of water, and the organic phase is washed with water. This crude methylene chloride solution of (II-c) is dried over sodium sulfate and then taken on crude into the next step.

In step 3 of Scheme 2, the crude solution of (II-c) in methylene chloride is concentrated to low volume and then the solvent is exchanged to methanol. The methanol solution of (II-c) is cooled to 0° C., then 1 mol % of potassium carbonate is added as a solution in methanol followed by stirring for 5 hours. The reaction is then quenched by addition of 1 mol % acetic acid in methanol, followed by warming to room temperature, solvent exchange to ethyl acetate, and then filtration of the minor amount of inorganic solids. The crude ethyl acetate solution of (II-d) is taken directly into the next step.

In step 4 of Scheme 2, the crude solution of (II-d) is concentrated to low volume, then diluted with methylene chloride and dimethylsulfoxide. Triethylamine is added followed by cooling to 10° C. and then sulfur trioxide pyridine complex is added in 3 portions as a solid at 10 minute intervals. The reaction is stirred an additional 3 hours at 10° C. before quenching with water and warming to room temperature. The phases are separated followed by washing the methylene chloride layer with aqueous ammonium chloride. The crude methylene chloride solution of (II-e) is taken directly into the next step.

In step 5 of Scheme 2, the crude solution of (II-e) is concentrated to low volume and then the solvent is exchanged to ethanol. Thirty equivalents of aqueous formaldehyde is added followed by warming to 55° C. An aqueous solution of 2 equivalents of potassium phosphate, tribasic is added followed by stirring for 24 hours at 55° C. The reaction temperature is then raised to 70° C. for an additional 12 hours. The reaction is cooled to room temperature, diluted with test-butyl methyl ether and brine. The phases are separated followed by solvent exchange of the organic phase to ethyl acetate. The ethyl acetate phase is washed with brine and concentrated to low volume. The crude concentrate is then purified by silica gel flash chromatography eluting with 5% methanol, 95% toluene. Product containing fractions are combined and concentrated to low volume. Methanol is added followed by stirring until precipitation occurs. The suspension is cooled and the solids are collected and rinsed with heptane followed by drying. Product (II-f) is isolated as a solid.

In step 6 of Scheme 2, compound (II-f) is dissolved in 5 volumes of methylene chloride followed by the addition of 1 mol % SiliaBond® tosic acid and stirring for 18 hours, at room temperature. The acid catalyst is filtered off and the methylene chloride solution of (II-g) is taken directly into the next step co-crystallization procedure.

In step 7 of Scheme 2, the methylene chloride solution of (II-g) is concentrated and then the solvent is exchanged to 2-propanol. Water is added followed by warming to 55° C. An aqueous solution of L-pyroglutamic acid is added followed by cooling the resulting solution to room temperature. The solution is then seeded and granulated for 18 hours. After cooling, the solids are collected and rinsed with heptane followed by drying. Product (II-h) is isolated as a solid.

An alternative synthetic route for compounds (S1-A) is depicted in Scheme 3 and described below.

Scheme 3

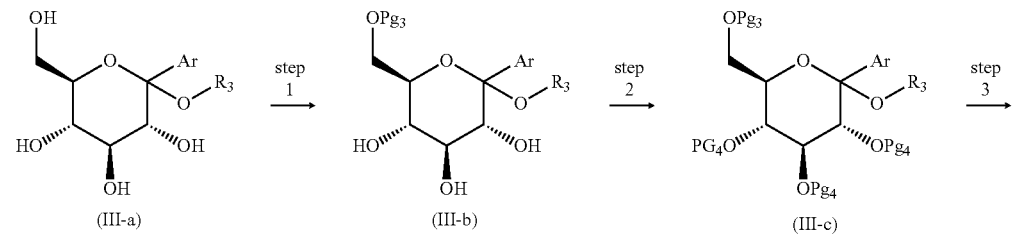

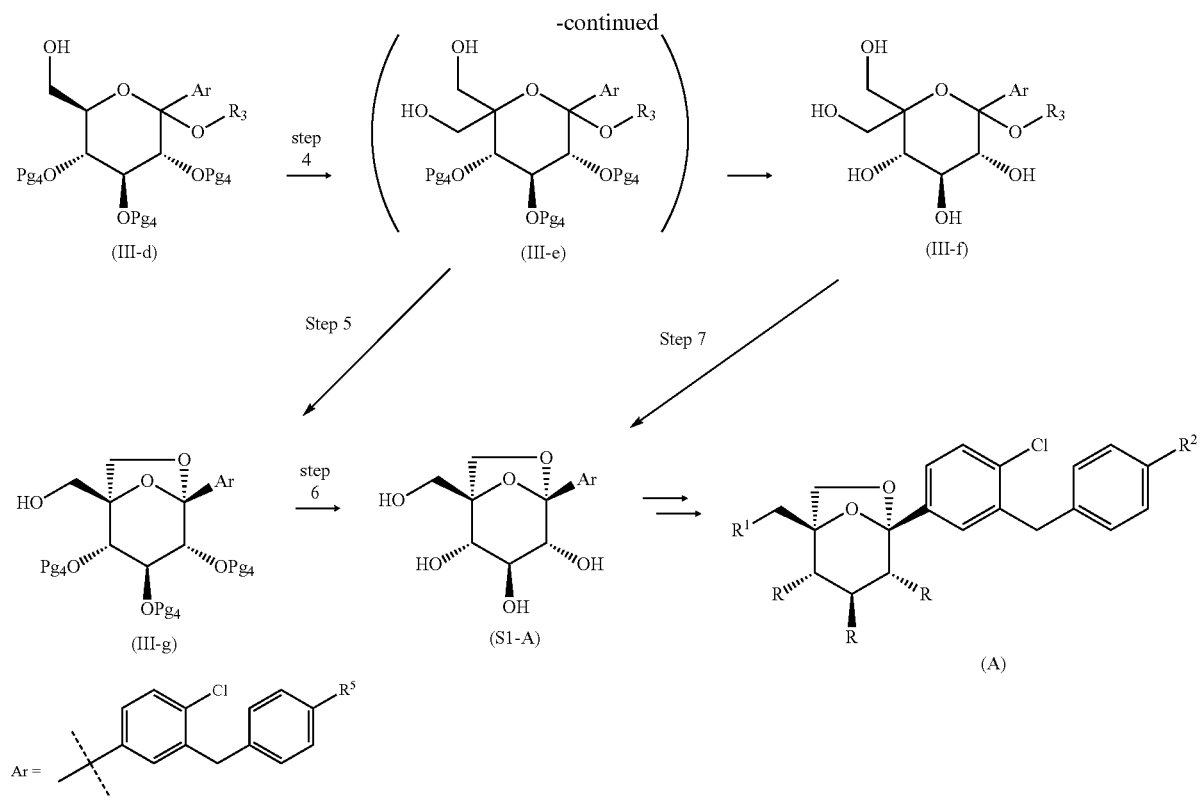

The synthesis of (III-a), where $R_3$ is an alkyl or fluoro substituted alkyl (except for the carbon adjacent to the oxygen atom) can be prepared in a similar way as described in step 1 of Scheme 2. In step 1 of Scheme 3, the primary hydroxyl group is selectively protected by an appropriate protective group. For example, a trityl group ($Pg_3$=Tr) can be introduced by treatment of intermediate (III-a) with chlorotriphenylmethane in presence of a base like pyridine in a solvent like toluene, tetrahydrofuran or dichloromethane at a temperature ranging from about 0 degrees Celsius to about room temperature. Additional examples of such protective groups and experimental conditions are known by those skilled in the art and can be found in T. W. Greene, *Protective Groups in Organic Synthesis*, John Wiley & Sons, New York, 1991.

In step 2 of Scheme 3, the secondary hydroxyl groups can be protected by the appropriate protecting groups. For example, benzyl groups ($Pg_4$ is Bn) can be introduced by treatment of intermediate (III-b) with benzyl bromide or benzyl chloride in the presence of sodium hydride, potassium hydride, potassium tert-butoxide in a solvent like tetrahydrofuran, 1,2-dimethoxyethane or N,N-dimethylformamide at a temperature ranging from about 0 degrees Celsius to about 80 degrees Celsius. Acetyl or benzoyl groups ($Pg_4$=Ac or Bz) may be introduced by treatment of intermediate (III-b) with acetyl chloride, acetyl bromide or acetic anhydride or benzoyl chloride or benzoic anhydride in the presence of a base like triethylamine, N,N-diisopropylethylamine or 4-(dimethylamino)pyridine in a solvent like tetrahydrofuran, 1,2-dimethoxyethane or dichloromethane at a temperature ranging from about 0 degrees Celsius to about 80 degrees Celsius.

In step 3 of Scheme 3, the primary hydroxyl group is deprotected to lead to intermediate (III-d). When $Pg_3$ is Tr, intermediate (III-c) is treated in the presence of an acid like para-toluenesulfonic acid in a alcoholic solvent like methanol at a temperature ranging from about −20 degrees Celsius to about room temperature to provide intermediate (III-d). Cosolvents like chloroform may be used.

In step 4 of Scheme 3, a hydroxymethylene group is introduced through a process similar to the one already described in Scheme 1 (step 1) and Scheme 2 (steps 4 and 5). Other sources of formaldehyde, like paraformaldehyde in a solvent like ethanol at a temperature ranging from about room temperature to about 70 degrees Celsius in the presence of an alkali metal alkoxide can also be used in this step. When $Pg_4$ is Bn, this step provides intermediate (III-e) and when $Pg_4$ is Ac or Bz, this step provides intermediate (III-f).

In step 5 of Scheme 3, intermediate (III-e) is treated with an acid like trifluoroacetic acid or an acidic resin in a solvent like dichloromethane at a temperature ranging from about −10 degrees Celsius to about room temperature to produce intermediate (III-g).

In step 6 of Scheme 3, the remaining protecting groups ($Pg_4$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce compound (S1-A).

In step 7 of Scheme 3, intermediate (III-f) is treated with an acid like trifluoroacetic acid or an acidic resin in a solvent like dichloromethane at a temperature ranging from about −10 degrees Celsius to about room temperature to produce product (S1-A).

Depending on $R^5$, the compounds thus obtained can then be easily functionalized to other compounds from the present invention of structure (A) using well known protective and functional groups manipulation sequences known by those skilled in the art. See examples section for further details.

Another alternative scheme for synthesizing product (A) is depicted in Scheme 4 and described below.

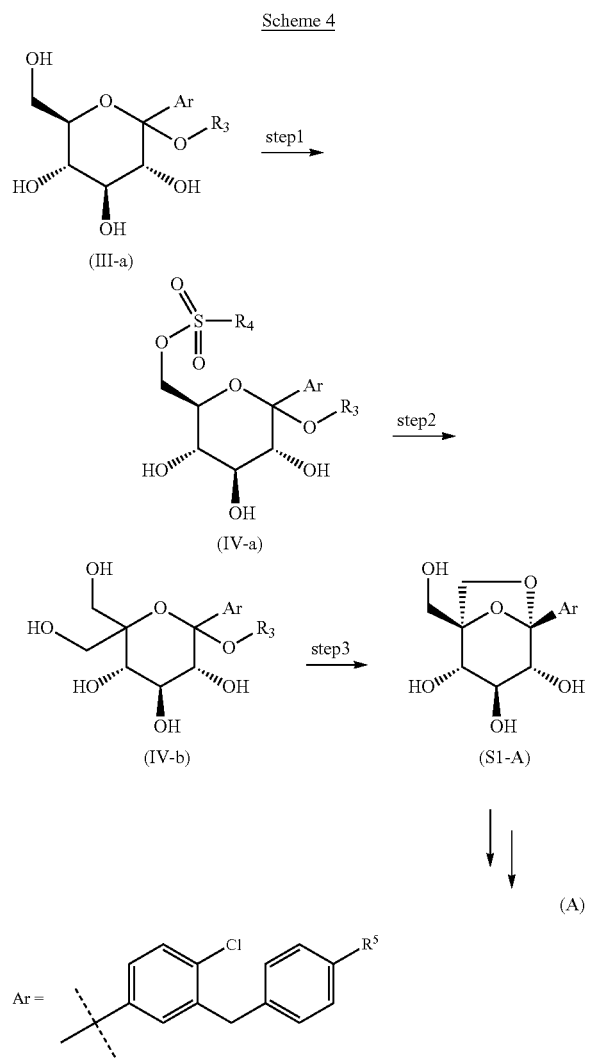

In step 1 of Scheme 4, intermediate (III-a) is treated with the appropriate arylsulfonyl chloride $R_4SO_2Cl$ or arylsulfonic anhydride $R_4S(O)_2OS(O)_2R_4$ (wherein $R_4$ is an optionally substituted aryl group, such as found in the arylsulfonyl chlorides 4-methyl-benzenesulfonyl chloride, 4-nitro-benzenesulfonyl chloride, 4-fluoro-benzenesulfonyl chloride, 2,6-dichloro-benzenesulfonyl chloride, 4-fluoro-2-methyl-benzenesulfonyl chloride, and 2,4,6-trichloro-benzenesulfonyl chloride, and in the arylsulfonic anhydride, p-toluenesulfonic anhydride) in presence of a base like pyridine, triethylamine, N,N-diisopropylethylamine in a solvent like tetrahydrofuran, 2-methyltetrahydrofuran at a temperature ranging from about −20 degrees Celsius to about room temperature. Some Lewis acids like zinc(II) bromide may be used as additives.

In step 2 of Scheme 4, intermediate (IV-a) is submitted to a Kornblum-type oxidation (see, Kornblum, N., et al., *Journal of The American Chemical Society*, 81, 4113 (1959)) to produce the corresponding aldehyde which may exist in equilibrium with the corresponding hydrate and/or hemiacetal form. For example intermediate (IV-a) is treated in the presence of a base like pyridine, 2,6-lutidine, 2,4,6-collidine, N,N-diisopropylethylamine, 4-(dimethylamino)pyridine in a solvent like dimethyl sulfoxide at a temperature ranging from about room temperature to about 150 degrees Celsius. The aldehyde intermediate produced is then submitted to the aldol/Cannizzaro conditions described for step 1 (Scheme 1) and step 5 (Scheme 2) to produce intermediate (IV-b).

In step 3 of Scheme 4, intermediate (IV-b) is treated with an acid like trifluoroacetic acid or an acidic resin in a solvent like dichloromethane at a temperature ranging from about −10 degrees Celsius to about room temperature to produce (S1-A). Depending on $R^5$, the compounds thus obtained can then be easily functionalized to other claimed compounds of structure (A) from the present invention using well known protective and functional groups manipulation sequences known by those skilled in the art. See examples section for further details.

Compounds (A) and (B) of the present invention can also be accessed via the process described in Scheme 5.

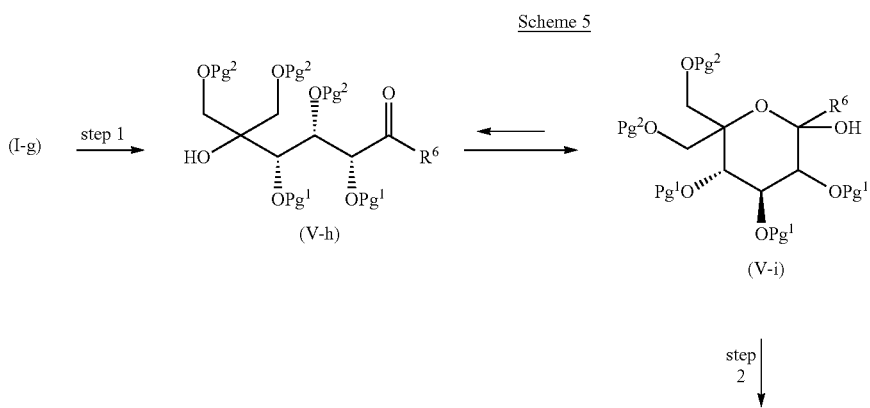

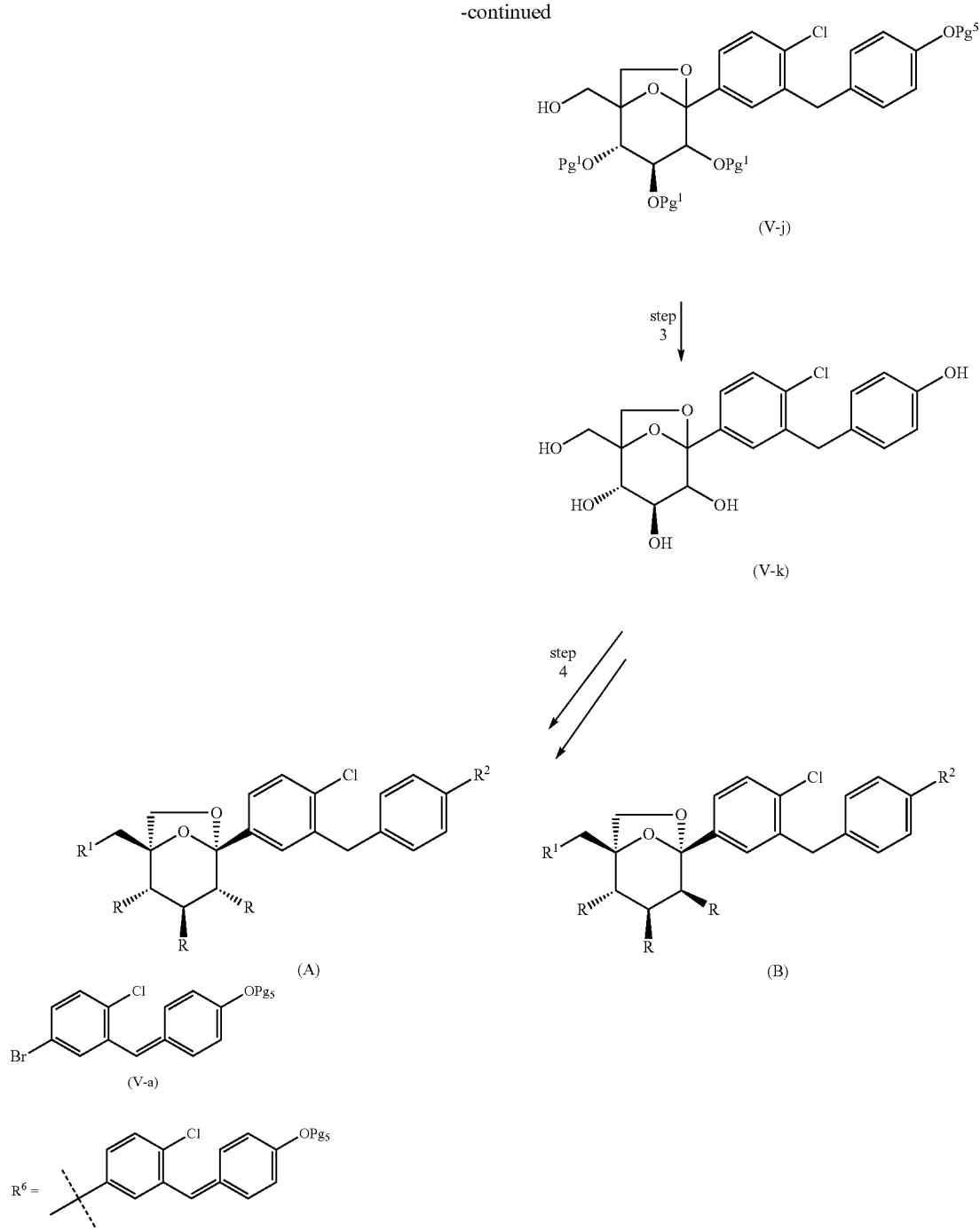

In step 1 of Scheme 5, which provides intermediate (V-i), the organometallic addition step is carried out in a similar way to the one described in Scheme 1, step 6, using the organometallic reagent derived from (V-a), where Pg$_5$ is a suitable protective group for the hydroxyl group. For instance Pg$_5$ can be a tert-butyldimethylsilyl group (TBS) (see US2007/0054867 for preparation of for instance {4-[(5-bromo-2-chloro-phenyl)-methyl]-phenoxy}-tert-butyl-dimethyl-silane).

In step 2 of Scheme 5, when Pg$^2$=PMB, intermediate (V-i) is treated with an acid like trifluoroacetic acid, methanesulfonic acid or an acidic resin in presence of anisole in a solvent like dichloromethane at a temperature ranging from about −10 degrees Celsius to about room temperature to produce intermediate (V-j).

In step 3 of Scheme 5, protecting groups (Pg$_5$) and (Pg$^1$) can be removed to provide (V-k). Typically (Pg$_5$) is TBS and Pg$^1$ is Bn. In this circumstance, the protecting groups are removed by sequential treatment of (V-j) with 1) tetrabutylammonium fluoride in a solvent like tetrahydrofuran or 2-methyltetrahydrofuran at a temperature ranging from 0 degrees Celsius to about 40 degrees Celsius and 2) treatment with formic acid in the presence of palladium (Pd black) in a protic solvent (e.g., ethanol/THF) at about room temperature. In this sequence, the order of the 2 reactions is interchangeable.

In step 4 of Scheme 5, intermediate (V-k) can for example be treated with an alkylating agent of choice under classical conditions to selectively alkylate the phenol group. Furthermore, the compounds thus obtained can then be easily functionalized to other claimed compounds of structure (A) and (B) from the present invention using well known protective and functional groups manipulation sequences known by those skilled in the art. See examples section for further details.

One skilled in the art would also understand that the chemistry described above in schemes 1 to 5 represents different ways of accessing intermediate (V-k).

Compounds of this invention are useful for treating diseases, conditions and/or disorders modulated by the inhibition of the sodium-glucose transporters (in particular SGLT2); therefore, another embodiment of this invention is a pharmaceutical composition comprising a therapeutically effective amount of a compound of this invention and a pharmaceutically acceptable excipient, diluent or carrier. The compounds of this invention (including the compositions and processes used therein) may also be used in the manufacture of a medicament for the therapeutic applications described herein.

A typical formulation is prepared by mixing a compound of this invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of this invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of this invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of this invention or stabilized form of the compound (e.g., complex with a cyclodextrin derivative or other known complexation agent)) is dissolved in a suitable solvent in the presence of one or more of the excipients described above. The compound of this invention is typically formulated into pharmaceutical dosage forms to provide an easily controllable dosage of the drug and to give the patient an elegant and easily handleable product.

The pharmaceutical compositions also include solvates and hydrates of the compounds of this invention. The term "solvate" refers to a molecular complex of this invention (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The crystalline forms may also exist as complexes with other innocuous small molecules, such as L-phenylalanine, L-proline, L-pyroglutamic acid and the like, as co-crystals or solvates or hydrates of the co-crystalline material. The solvates, hydrates and co-crystalline compounds may be prepared using procedures described in PCT Publication No. WO 08/002824, incorporated herein by reference, or other procedures well-known to those of skill in the art.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

This invention further provides a method of treating diseases, conditions and/or disorders modulated by the inhibition of sodium-glucose transporters in an animal that includes administering to an animal in need of such treatment a therapeutically effective amount of a compound of this invention or a pharmaceutical composition comprising an effective amount of a compound of this invention and a pharmaceutically acceptable excipient, diluent, or carrier. The method is particularly useful for treating diseases, conditions and/or disorders that benefit from the inhibition of SGLT2.

One aspect of this invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of this invention is the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, delayed wound healing, hyperinsulinemia, elevated blood levels of fatty acids, hyperlipidemia, hypertriglyceridemia, Syndrome X, increased high density lipoprotein levels, insulin resistance, hyperglycemia, and diabetic complications (such as atherosclerosis, coronary heart disease, stroke, peripheral vascular disease, nephropathy, hypertension, neuropathy, and retinopathy).

Yet another aspect of this invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005).

Preferably, administration of the compounds of this invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of this invention may also provide a statistically significant ($p<0.05$) reduction in glucose serum levels.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of this invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of this invention in combination with other pharmaceutical agents are also provided. Suitable pharmaceutical agents that may be used in combination with the compounds of this invention include anti-obesity agents (including appetite suppressants), anti-diabetic agents, anti-hyperglycemic agents, lipid lowering agents, anti-inflammatory agents and anti-hypertensive agents.

Suitable anti-obesity agents include cannabinoid-1 (CB-1) antagonists (such as rimonabant), 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, β$_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), PYY$_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of this invention include CB-1 antagonists (e.g., rimonabant, taranabant, surinabant, otenabant, SLV319 (CAS No. 464213-10-3) and AVE1625 (CAS No. 358970-97-5)), gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3, 6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), PYY$_{3-36}$ (as used herein "PYY$_{3-36}$" includes analogs, such as peglated PYY$_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of this invention and combination therapies are administered in conjunction with exercise and a sensible diet.

Suitable anti-diabetic agents include an acetyl-CoA carboxylase-2 (ACC-2) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3, exendin-4, and liraglutide), a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, a VPAC2 receptor agonist and a glucokinase activator. Preferred anti-diabetic agents are metformin and DPP-IV inhibitors (e.g., sitagliptin, vildagliptin, alogliptin and saxagliptin).

Suitable anti-inflammatory agents include genital tract/urinary tract infection preventatives and treatments. Exemplary agents include cranberries (i.e. *Vaccinium macrocarpon*) and cranberry derivatives such as cranberry juice, cranberry extracts or flavonols of cranberries. Cranberry extracts may include one or more flavonols (i.e. anthocyanins and proanthocyanidins) or a purified cranberry flavonol compound, including myricetin-3-β-xylopyranoside, quercetin-3-β-glucoside, quercetin-3-α-arabinopyranoside, 3'-methoxyquercetin-3-α-xylopyranoside, quercetin-3-O-(6"-p-coumaroyl)-β-galactoside, quercetin-3-O-(6"-benzoyl)-β-galactoside, and/or quercetin-3-α-arabinofuranoside.

Embodiments of this invention are further illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), and Accela ChemBio (San Diego, Calif.).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (delta) relative to residual solvent as an internal reference. The peak shapes are denoted as follows: s, singlet; d, doublet; dd, doublet of doublet; t, triplet; q, quartet; m, multiplet; bs or br.s., broad singlet; 2s, two singlets; br.d., broad doublet. Electrospray ionization mass spectra (ES) were obtained on a Waters™ ZMD instrument (carrier gas: nitrogen; solvent A: water/0.01% formic acid, solvent B: acetonitrile/0.005% formic acid; available from Waters Corp., Milford, Mass.). High resolution mass spectra (HRMS) were obtained on an Agilent™ Model 6210 or 6220A time of flight. Where the intensity of single chlorine or single bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given.

Column chromatography was performed with either Baker™ silica gel (40 microm; J.T. Baker, Phillipsburg, N.J.) or Silica Gel 50 (EM Sciences™ Gibbstown, N.J.) in glass columns or in Flash 40 Biotage™ columns (ISC, Inc., Shelton, Conn.). MPLC (medium pressure liquid chromatography) was performed using a Biotage™ SP purification system or a Combiflash® Companion® from Teledyne™ Isco™; Biotage™ SNAP cartridge KPsil or Redisep Rf silica (from Teledyne™ Isco™) under low nitrogen pressure were used. HPLC (high performance liquid chromatography) was performed using a Shimadzu™ 10A LC-UV or a Agilent™ 1100 preparatory HPLC. Except where otherwise noted, all reactions were run under an inert atmosphere of nitrogen gas using anhydrous solvents. Also, except where otherwise noted, all reactions were run at room temperature (~23° C.). When doing TLC (thin layer chromatography), $R_f$ is defined as the ratio of the distance traveled by the compound divided by the distance traveled by the eluent. $R_t$ (retention time).

Starting Materials

Generally, any of the following starting materials can be prepared using the procedures described in Schemes 7 or 8 of US Publication No. 2008/0132563, or alternatively, Schemes 2, 3 or 8 of US Publication No. 2007/0259821. More specifically, the following starting materials used in the following Examples can be prepared using the procedures described in the corresponding references or purchased from the corresponding vendor.

4-(5-bromo-2-chloro-benzyl)-phenol can be prepared by the procedures described in Example III of EP1828216B1.

4-Bromo-1-chloro-2-(4-ethoxy-benzyl)-benzene and (5-bromo-2-chlorophenyl)(4-ethoxyphenyl)-methanone may be purchased from Shanghai Haoyuan Chemexpress Co., Ltd., Shanghai, People's Republic of China.

The following starting materials were prepared as described below.

4-(5-bromo-2-chloro-benzyl)-phenol

To a solution of 4-bromo-1-chloro-2-(4-ethoxy-benzyl)-benzene (5.0 g, 15.35 mmol) in dichloromethane (20.0 mL) cooled to 0 degrees Celsius under nitrogen was added drop-wise over 30 minutes a 1M solution of boron tribromide in dichloromethane (17.0 mL, 17.0 mmol). After the addition was complete, the reaction was allowed to warm to room temperature overnight (~16 hours). The reaction was cooled to 0 degrees Celsius and quenched with an aqueous solution of 1N hydrochloric acid. The resulting mixture was stirred for 30 minutes and extracted using dichloromethane. The organic layer was separated and the aqueous layer was extracted two times with dichloromethane. The combined organic layers were dried over magnesium sulfate, filtered and concentrated under reduced pressure. The reaction was purified by flash chromatography over silica gel using the ISCO automated chromatography unit (120 g silica gel column) and eluting with a gradient of 0 to 100% ethyl acetate in heptane. 3.53 g of desired product obtained (77% yield). $^1H$ NMR (400 MHz, METHANOL-$d_4$) delta ppm 3.94 (s, 2 H), 6.70 (d, J=8.6 Hz, 2 H), 6.98 (d, J=8.4 Hz, 2 H), 7.23-7.34 (m, 3 H).

Alternative Procedure:

To a solution of 4-bromo-1-chloro-2-(4-ethoxy-benzyl)-benzene (10.0 g, 30.71 mmol) in dichloromethane (40.0 mL) cooled to 0 degrees Celsius under nitrogen was added drop-wise over 30 minutes a 1M solution of boron trichloride in dichloromethane (34 mL, 34.0 mmol). After the addition was complete, the reaction was allowed to warm to room temperature overnight (~16 hours). The reaction mixture was cooled to 0 degrees Celsius and an aqueous solution of 1N hydrochloric acid was added. The resulting mixture was stirred for 30 minutes and then extracted using dichloromethane. The organic layer was separated and the aqueous layer was extracted two times with dichloromethane. The combined organic layers were dried over magnesium sulfate, filtered and concentrated under reduced pressure. The TLC showed only 50% conversion. The crude material was redissolved in dichloromethane (40 mL), cooled to 0 degrees Celsius, and a 1M solution of boron tribromide in dichloromethane (31 mL, 31 mmol) was added dropwise. The reaction mixture was allowed to warm to room temperature over the weekend (~55 hours). The reaction mixture was cooled to 0 degrees Celsius and an aqueous solution of 1N hydrochloric acid was added dropwise. The resulting mixture was stirred for 30 minutes and then extracted using dichloromethane. The organic layer was separated and the aqueous layer was extracted two times with dichloromethane. The combined organic layers were dried over magnesium sulfate, filtered and concentrated under reduced pressure. The reaction was purified by flash chromatography over silica gel using the ISCO automated chromatography unit (120 g silica gel column) and eluting with a gradient of 0 to 100% ethyl acetate in heptane. 9 g (98% yield) of the desired product obtained as a white solid.

[4-(5-Bromo-2-chloro-benzyl)-phenoxy]-tert-butyl-dimethyl-silane

To a solution of 4-(5-bromo-2-chloro-benzyl)-phenol (9.01 g, 30.28 mmol) dissolved in N,N-dimethylformamide (100 mL) and cooled to 0 degrees Celsius (ice bath) was added imidazole (4.53 g, 66.6 mmol) and 4-dimethylaminopyridine (370 mg, 3.03 mmol). tert-butylchlorodimethylsilane (6.85 g, 45.4 mmol) was added and the ice bath was removed. The reaction mixture was allowed to stir at room temperature overnight (~16 hours), water (400 mL) was added and the resulting mixture was extracted with ethyl acetate (200 mL). The aqueous layer was extracted two additional times with ethyl acetate (200 mL). The combined organic layers were washed with water (200 mL), brine (200 mL), dried over sodium sulfate, filtered and concentrated under reduced pressure. The crude material was purified by flash chromatography over silica gel using the ISCO automated chromatography unit (120 g silica gel column) and eluting with a gradient of 0 to 50% ethyl acetate in heptane. 12.4 g (99% yield) of product obtained as a clear oil. $^1$H NMR (400 MHz, CHLOROFORM-d) delta ppm 0.18 (s, 6 H), 0.97 (s, 9 H), 3.96 (s, 2 H), 6.77 (d, J=8.4 Hz, 2 H), 7.01 (d, J=8.4 Hz, 2 H), 7.17-7.30 (m, 3 H).

Preparation of Intermediates

Preparation of Intermediate ((2R,3R,4S,5R)-6-allyloxy-3,4,5-tris-benzyloxy-tetrahydro-pyran-2-yl)-methanol (I-1a)

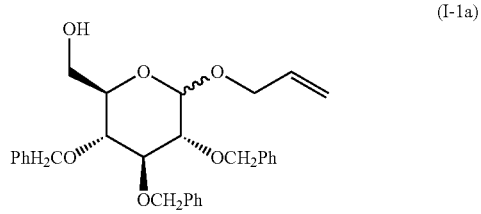

(I-1a)

A suspension of D-glucose (1.2 kg, 6.6 mol), trifluoromethane sulfonic acid (12 mL) and allyl alcohol (5 L) was heated at 80° C. for 3 days. The mixture was cooled down to room temperature, the volatiles were removed in vacuo and the residue dissolved in N,N-dimethylformamide (8 L). This was split into four equal reactions and to each was added trityl chloride (463 g, 1.67 mol) and triethylamine (231 mL, 1.67 mol). A slight exotherm was observed while adding the triethylamine. The reaction mixture was stirred for 2 days at 30° C. and then each reaction split in half, giving eight equal reactions. To each of these reactions was added benzyl chloride (300 mL, 2.60 mol), followed by portionwise addition of sodium hydride (102.5 g, 2.60 mol) maintaining the reaction temperature between 40 to 50° C. After complete addition, the reaction mixtures were stirred at room temperature for 20 hours. Each reaction was then poured onto ice/water (2 L) and extracted with ethyl acetate (2.5 L). The organic phases of each were washed with saturated brine/water (1:1, 2×2 L), combined and dried over magnesium sulfate (product $R_f$ 0.85 in 3:1 hexanes/ethyl acetate), After filtration and evaporation the residue was dissolved in a mixture of dichloromethane (16 L) and methanol (4 L). The mixture was split into 5 equal portions and to each was added sulfuric acid (32 mL). The reactions were stirred for 3 hours, washed with brine/2M aqueous sodium hydroxide solution (1:1, 2×2 L), combined and dried over magnesium sulfate. After filtration and concentration in vacuo, the residue was further purified on silica gel eluting with 30% ethyl acetate in toluene to give intermediate compound (I-1a) as a mixture of anomers (1.77 kg, 54% yield from D-glucose). $R_f$ 0.15 in 3:1 hexanes/ethyl acetate.

Preparation of Intermediate ((3S,4S,5R)-6-allyloxy-3,4,5-tris-benzyloxy-2-hydroxymethyl-tetrahydro-pyran-2-yl)-methanol (I-1b)

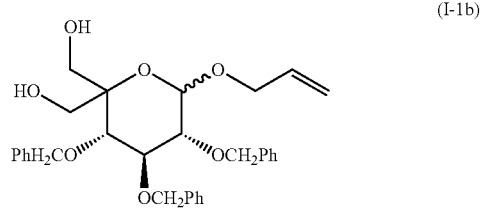

(I-1b)

A solution of dimethylsulfoxide (87 mL, 1.22 mol) in dichloromethane (160 mL) was added dropwise to a solution of oxalyl chloride (64.7 mL, 0.76 mol) in dichloromethane (2.5 L) at −78° C. After complete addition a solution of intermediate (I-1a) (287 g, 0.59 mol) in dichloromethane (500 mL) was added dropwise at −78° C. After complete addition the reaction mixture was stirred for 30 minutes and triethylamine (417 mL, 2.9 mol) was added dropwise. After complete addition the reaction mixture was allowed to self warm to room temperature. The reaction was then washed with 1M aqueous hydrochloric acid solution (2 L) and water (2 L), and then dried over magnesium sulfate. This reaction procedure was repeated on six equivalent reactions and after drying they were combined and evaporated to give the aldehyde as a yellow oil (1.71 kg). This oil was dissolved in isopropanol (2.57 L) and split into seven equal reactions. To each of these was added a 37% aqueous formaldehyde solution (0.79 L, 10 mol), followed by the dropwise addition of a solution of sodium hydroxide (32 g, 0.8 mol) in water (130 mL). After complete addition the reaction mixture was stirred at room temperature for 2 days. The reaction mixture was diluted with brine (2 L) and extracted with ethyl acetate (2 L). The organic phase was further washed with saturated aqueous sodium bicarbonate solution (2 L), brine (2 L) and then dried over magnesium sulfate. The organic phases from the seven reactions were combined, evaporated and the residue purified on silica gel (eluting with 4 to 1 up to 1 to 1 hexanes in ethyl acetate) to give intermediate compound (I-1b) as a mixture of anomers (980 g, 53% yield over the two steps). $R_f$ 0.57 and 0.60 in 1:1 hexanes/ethyl acetate.

(3S,4S,5R)-6-allyloxy-3,4,5-tris-benzyloxy-2,2-bis-(4-methoxy-benzyloxymethyl)-tetrahydro-pyran (I-1c)

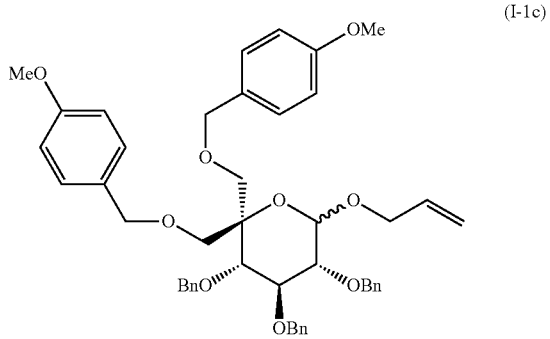

(I-1c)

The starting diol [((3S,4S,5R)-6-allyloxy-3,4,5-tris-benzyloxy-2-hydroxymethyl-tetrahydro-pyran-2-yl)-methanol (I-1b: 10 g, 19.208 mmol) was dissolved in N,N-dimethylformamide (70 mL) and cooled to 0° C. Sodium hydride (60% dispersion in mineral oil, 1.69 g, 42.3 mmol) was added and the reaction was allowed to stir at 0° C. for 1 hour before the addition of 1-bromomethyl-4-methoxy-benzene (5.96 mL, 40.3 mmol). The reaction was then heated to 60° C. overnight. The mixture was cooled down to room temperature and the reaction was quenched with water and extracted with ethyl acetate (2 times). The combined organic layers were washed with water, brine, dried over sodium sulfate, filtered and concentrated under reduced pressure. The reaction was then chromatographed over silica gel (eluting with a gradient of 0 to 80% ethyl acetate in heptane) yielding 7.55 g (52% yield) of product (I-1c). MS 778.8 (M+NH$_4^+$; positive mode).

(3R,4S,5S)-3,4,5-tris-benzyloxy-6,6-bis-(4-methoxy-benzyloxymethyl)-tetrahydro-pyran-2-ol (I-1d)

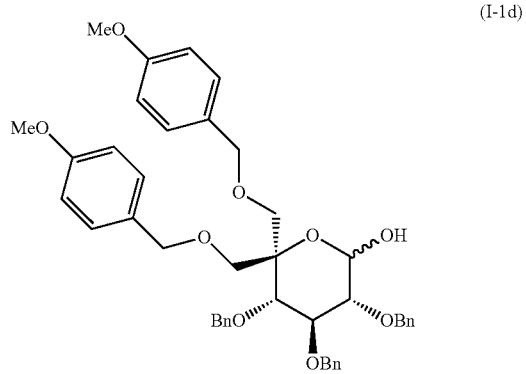

(I-1d)

To a solution of starting material ((3S,4S,5R)-6-allyloxy-3,4,5-tris-benzyloxy-2,2-bis-(4-methoxy-benzyloxymethyl)-tetrahydro-pyran, (I-1c: 7.55 g, 9.92 mmol) in methanol (60 mL) and dichloromethane (20 mL) at room temperature was added in palladium (II) chloride (528 mg, 2.98 mmol) and the resulting mixture was stirred at this temperature for 4 hours. TLC indicated the clean formation of a more polar product. The reaction was filtered through Celite® and concentrated under reduced pressure. The crude material was chromatographed over silica gel eluting with a gradient of 0 to 80% ethyl acetate in heptane yielding 5.6 g (78% yield) of product (I-1d). MS 738.8 (M+NH$_4^+$; positive mode).

(3R,4S,5S)-3,4,5-tris-benzyloxy-6,6-bis-(4-methoxy-benzyloxymethyl)-tetrahydro-pyran-2-one (I-1e)

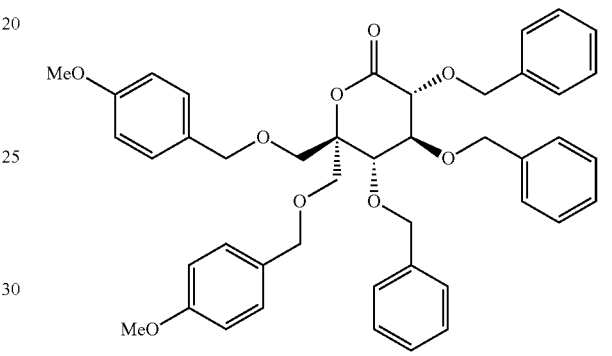

(I-1e)

To a solution of oxalyl dichloride (1.9 mL, 23 mmol) in dichloromethane (65 mL) at −78° C. was added a solution of dimethyl sulfoxide (3.3 mL, 47 mmol) in dichloromethane (5 mL) and the resulting solution was stirred at this temperature for 30 minutes. A solution of starting material ((3R,4S,5S)-3,4,5-tris-benzyloxy-6,6-bis-(4-methoxy-benzyloxymethyl)-tetrahydro-pyran-2-ol, (I-1d, 5.6 g, 7.7 mmol) in dichloromethane (15.0 mL) was then added dropwise and the resulting mixture was stirred for 30 minutes allowing the temperature to rise to −60° C. Triethylamine (9.7 mL, 69.5 mmol) was added dropwise and the mixture allowed to warm up to 0° C. over 1 hour. The reaction was quenched by addition of saturated aqueous ammonium chloride solution and the organic phase was dried over magnesium sulfate, filtered and concentrated under reduced pressure. The crude material was purified by flash chromatography over silica gel eluting with a gradient of 0 to 60% ethyl acetate in heptane to produce the product (I-1e) (4 g, 72% yield).

$^1$H NMR (400 MHz, chloroform-d) delta ppm 3.24 (d, J=10 Hz, 1 H), 3.40-3.47 (m, 2 H), 3.74 (s, 3 H), 3.77 (s, 3 H), 3.86 (d, J=10 Hz, 1 H), 4.07 (d, J=8.6 Hz, 1 H), 4.15 (d, J=9.6 Hz, 1 H), 4.35-4.55 (m, 6 H), 4.65-4.72 (m, 2 H), 4.82 (d, J=11 Hz, 1 H), 4.87 (d, J=11.2 Hz, 1 H), 5.10 (d, J=11.1 Hz, 1 H), 6.74-6.79 (m, 2 H), 6.81-6.85 (m, 2 H), 7.11 (dd, J=7.0, 2.5 Hz, 2 H), 7.17-7.41 (m, 17 H).

(2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) and/or (3R,4S,5S)-3,4,5-tris-benzyloxy-6,6-bis-(4-methoxy-benzyloxymethyl)-2-(methoxy-methyl-amino)-tetrahydro-pyran-2-ol (I-1f)

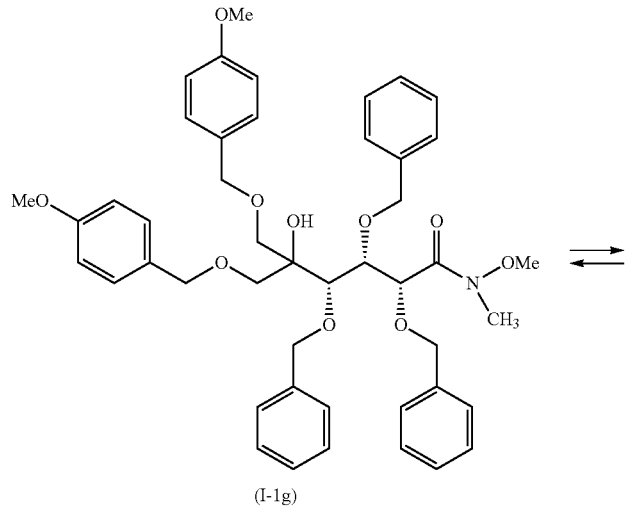

(I-1g)

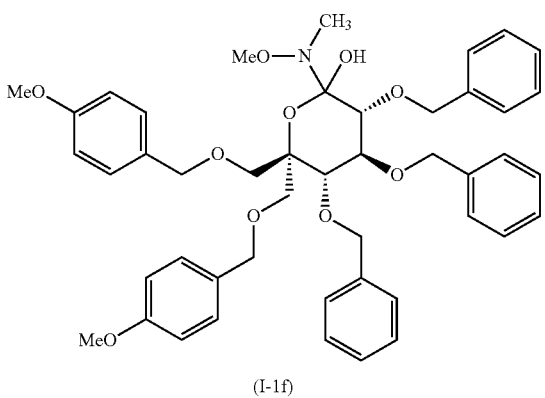

(I-1f)

To a solution of lactone ((3R,4S,5S)-3,4,5-tris-benzyloxy-6,6-bis-(4-methoxy-benzyloxymethyl)-tetrahydro-pyran-2-one (I-1e: 10.4 g, 14.5 mmol) and N,O-dimethyl-hydroxylamine hydrochloride (1.77 g, 29.0 mmol) in dichloromethane (100 mL) at 0° C. was added dropwise a 2.0 M solution of trimethyl aluminum in hexanes (14.5 mL, 29.0 mmol) and the resulting solution was stirred at room temperature for 16 hours. The reaction mixture was cooled to 0° C. and quenched by slow addition of aqueous 1N hydrochloric acid solution. The resulting mixture was allowed to stir for 1 hour. The organic phase was separated and washed with aqueous 1N hydrochloric acid solution, dried over sodium sulfate, filtered, and concentrated under reduced pressure. The crude material was purified by medium pressure chromatography (gradient of 5 to 40% ethyl acetate in heptane) yielding 6.5 g (58%) of product.

$^1$H NMR (400 MHz, chloroform-d) delta ppm 2.62 (br. s, 1 H), 2.94 (br. s., 3 H), 3.23 (br. s., 3 H), 3.42 (d, J=9.4 Hz, 1 H), 3.50-3.60 (m, 3 H), 3.75 (s, 3 H), 3.77 (s, 3 H), 4.03 (d, J=6.9 Hz, 1 H), 4.20 (dd, J=6.9, 3.3 Hz, 1 H), 4.31-4.44 (m, 5 H), 4.46-4.51 (m, 2 H), 4.53 (d, J=12 Hz, 1 H), 4.66 (d, J=12 Hz, 1 H), 4.80 (br. d, J=11.5 Hz, 1 H), 4.87 (d, J=11.4 Hz, 1 H), 6.77-6.83 (m, 4 H), 7.15-7.35 (m, 19 H). ([M+H$^+$] 780.8, positive mode; [M+HCO$_2$] 824.7, negative mode). HRMS calculated for C$_{46}$H$_{54}$NO$_{10}$ (M+H$^+$) 780.3742. found 780.3708.

(4S,5S)-3,4,5-tris-benzyloxy-2-[4-chloro-3-(4-ethoxy-benzyl)-phenyl]-6,6-bis-(4-methoxy-benzyloxymethyl)-tetrahydro-pyran-2-ol (I-1i)

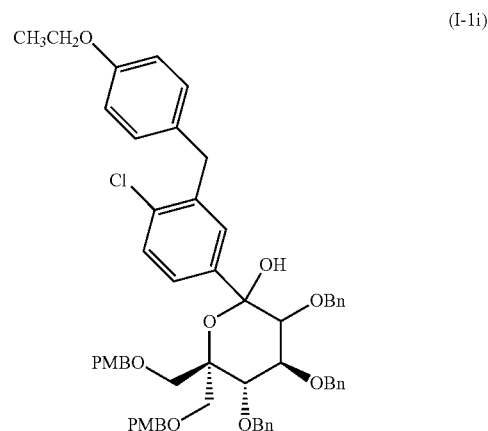

(I-1i)

n-Butyl lithium (1.0 mL, 2.5 M/hexanes, 3.25 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 4-bromo-1-chloro-2-(4-ethoxy-benzyl)-benzene (815 mg, 3.25 equivalents) in anhydrous tetrahydrofuran (2.9 mL) at −78° C. and the resulting solution was stirred at this temperature for an additional hour. A solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) (600 mg) in anhydrous tetrahydrofuran (1.45 mL) was then added dropwise over 1.3 hours using a syringe pump and the resulting mixture was stirred at −78° C. for 1 hour before being allowed to warm to −25° C. over 14 hours (put in a deep Dewar covered with aluminum foil to maintain cold temperature; size of Dewar: external diameter 10 cm, internal diameter 8 cm, height 9 cm). Diethyl ether was added and the reaction was quenched by dropwise addition of aqueous 1M hydrochloric acid solution. The resulting biphasic mixture was stirred at room temperature for 15 minutes. The organic phase was separated, washed with brine, dried over magnesium sulfate, filtered and concentrated. Chromatography over silica gel using a gradient of 10 to 40% ethyl acetate in heptane gave the product as a mixture of isomers (280 mg, 38% yield).

HRMS calculated for $C_{59}H_{61}O_{10}ClNa$ (M+Na$^+$) 987.3845. found 987.3840.

{(2S,3S)-2,3,4-tris-benzyloxy-5-[4-chloro-3-(4-ethoxy-benzyl)-phenyl]-6,8-dioxa-bicyclo[3.2.1]oct-1-yl}-methanol (I-1k):

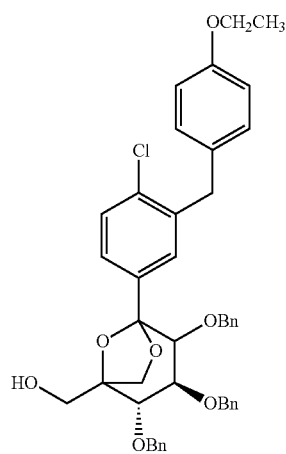

(I-1k)

To a solution of the intermediate I-1i (1.46 g) in dichloromethane (31 mL) was added anisole (900 microL, ~5 equivalents) followed by 31 mL of a solution of 20% trifluoroacetic acid in dichloromethane and the resulting mixture was stirred at room temperature for 1 hour. The mixture was concentrated and the crude was chromatographed over silica gel using a gradient of 10 to 30% ethyl acetate in heptane to afford the product as a mixture of isomers (670 mg, 63% yield).

HRMS calculated for $C_{43}H_{44}O_7Cl$ (M+H$^+$) 707.2770. found 707.2765.

(1S,2S,3S,4R,5S)-5-[4-chloro-3-(4-ethoxy-benzyl)-phenyl]-1-hydroxymethyl-6,8-dioxa-bicyclo[3.2.1] octane-2,3,4-triol (1A) and (1S,2S,3S,4S,5S)-5-[4-chloro-3-(4-ethoxy-benzyl)-phenyl]-1-hydroxymethyl-6,8-dioxa-bicyclo[3.2.1]octane-2,3,4-triol (1B)

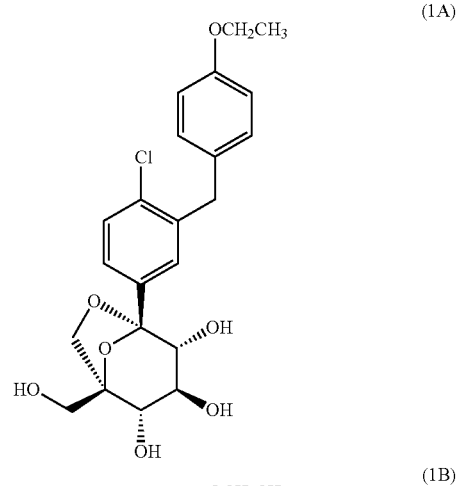

(1A)

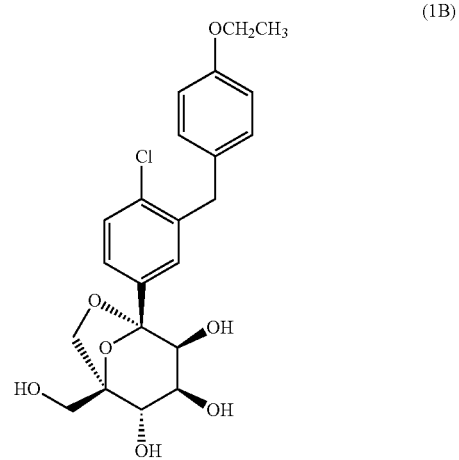

(1B)

To a solution of {(2S,3S)-2,3,4-tris-benzyloxy-5-[4-chloro-3-(4-ethoxy-benzyl)-phenyl]-6,8-dioxa-bicyclo [3.2.1]oct-1-yl}-methanol (I-1k: 335 mg) in ethanol/tetrahydrofuran (10 mL, 4/1 volume) was added successively formic acid (420 microL, 22 equivalents) and palladium black (208 mg, 4 equivalents) and the resulting mixture was stirred at room temperature. After 1 hour, additional formic acid (420 microL, 22 equivalents) and palladium black (208 mg, 4 equivalents) were added and the mixture was allowed to stir for an additional hour at room temperature. The palladium was filtered and the crude mixture obtained after evaporation of solvent was purified by HPLC preparative.

HPLC preparative: reverse phase C18 Gemini column 5 micrometer 30×100 mm, 40 mL/minute, gradient of acetonitrile/0.1% formic acid:water/0.1% formic acid; 25 to 50% of acetonitrile/0.1% formic acid over 18 minutes; UV detection: 220 nm. The HPLC indicated a ratio of diastereomers of 1.1:1 (1A:1B).

(1A): (60 mg, 29% yield); R$_t$=12.4 minutes; the fractions containing the product were concentrated under reduced pressure. The crude material was precipitated from ethyl acetate and heptane. The resulting white solid was washed with heptane 2 times and dried under reduced pressure.

MS (LCMS) 437.3 (M+H$^+$; positive mode); 481.3 (M+HCO$_2^-$; negative mode). $^1$H NMR (400 MHz, methanol-d$_4$) delta 7.43 (d, 1H, J=1.9 Hz), 7.36 (dd, 1H, J=8.3 and 2 Hz), 7.32 (d, 1H, J=8.3 Hz), 7.08-7.04 (m, 2H), 6.79-6.75 (m, 2H), 4.12 (d, 1H, J=7.5 Hz), 4.00 (s, 2H), 3.96 (q, 2H, J=7.0 Hz), 3.81 (d, 1H, J=12.5 Hz), 3.75 (dd, 1H, J=8.3 and 1.3 Hz), 3.65 (d, 1H, J=12.5 Hz), 3.63 (t, 1H, J=8.2 Hz), 3.57 (dd, 1H, J=7.5 and 1.3 Hz), 3.52 (d, 1H, J=8.0 Hz), 1.33 (t, 3H, J=6.9 Hz). HRMS calculated for C$_{22}$H$_{26}$O$_7$Cl (M+H$^+$) 437.1361. found 437.1360.

(1B): (30 mg, 15% yield); R$_t$=13.2 minutes; the fractions containing the product were concentrated under reduced pressure. The crude material was precipitated from ethyl acetate and heptane. The resulting white solid was washed with heptane 2 times and dried under reduced pressure.

MS (LCMS) 437.3 (M+H$^+$; positive mode) 481.3 (M+HCO$_2^-$, negative mode). $^1$H NMR (400 MHz, methanol-d$_4$) delta 7.48 (d, 1H, J=1.9 Hz) 7.40 (dd, 1H, J=8.1 and 1.9 Hz), 7.32 (d, 1H, J=8.3 Hz), 7.08-7.03 (m, 2H), 6.80-6.74 (m, 2H), 4.04-3.99 (m, 3H), 3.95 (q, 2H, J=7 Hz), 3.89-3.81 (m, 4H), 3.73 (d, 1H, J=12.5 Hz), 3.49 (d, 1H, J=7.3 Hz), 1.32 (t, 3H, J=7 Hz). HRMS calculated for C$_{22}$H$_{26}$O$_7$Cl (M+H$^+$) 437.1361. found 437.1358.

(2S,3R,4S,5S,6R)-2-[4-chloro-3-(4-hydroxy-benzyl)-phenyl]-6-hydroxymethyl-2-methoxy-tetrahydro-pyran-3,4,5-triol

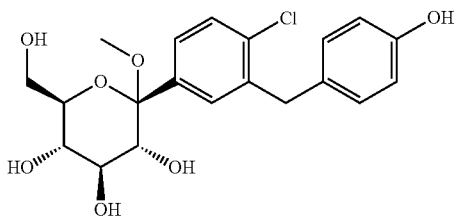 [SMILES: CO[C@@]1(c2ccc(Cl)c(Cc3ccc(O)cc3)c2)O[C@H](CO)[C@@H](O)[C@H](O)[C@H]1O]

A 2.5 M solution of n-butyl lithium in hexane (15 mL, 37.5 mmol) was slowly added to a stirred solution of [4-(5-bromo-2-chloro-benzyl)-phenoxy]-tert-butyl-dimethyl-silane (12.6 g, 30.6 mmol) in 75 mL of a dry THF (25 mL) and toluene (50 mL) solution cooled at −78 degrees Celsius under nitrogen. After stirring for 30 minutes following the addition, the solution was transferred by cannula to a stirring solution of (3R,4S,5R,6R)-3,4,5-tris-trimethylsilanyloxy-6-trimethylsilanyloxymethyl-tetrahydro-pyran-2-one (18.6 g, 40 mmol) in 50 mL of toluene at −78 degrees Celsius. After 1.5 hours following the addition the reaction was quenched at −78 degrees Celsius by the dropwise addition of 5 mL of methanol containing methanesulfonic acid (0.5 mL) and the resulting mixture was allowed to warm to room temperature overnight (~16 hours). An additional 4.5 mL of methylsulfonic acid in 50 mL of methanol was added dropwise at room temperature and the reaction mixture was stirred at room temperature for an additional 24 hours. A solution of saturated aqueous sodium bicarbonate (300 mL) and ethyl acetate (100 mL) were added and the resulting mixture was stirred for 1 hour. The layers were separated and the aqueous layer was extracted two additional times with ethyl acetate (100 mL). The combined organic layers were washed with brine, dried over sodium sulfate, filtered and concentrated under reduced pressure. The crude material was purified by flash chromatography over silica gel using the ISCO automated chromatography unit (two 120 g silica gel columns) and eluting with a gradient of 0 to 30% methanol in dichloromethane. 4.2 g (33% yield) of product obtained as an off white solid. LCMS 433 (M+Na$^+$, positive mode). $^1$H NMR (500 MHz, METHANOL-d$_4$) delta ppm 3.08 (s, 3 H), 3.10 (d, J=9.5 Hz, 1 H), 3.43 (t, J=9.3 Hz, 1 H), 3.60 (ddd, J=9.9, 5.7, 2.0 Hz, 1 H), 3.76 (t, J=9.1 Hz, 1 H), 3.82 (dd, J=12.0, 5.6 Hz, 1 H), 3.94 (dd, J=12.1, 1.8 Hz, 1 H), 3.96-4.10 (m, 2 H), 6.69 (d, J=8.3 Hz, 2 H), 7.02 (d, J=8.3 Hz, 2 H), 7.37 (d, J=8.3 Hz, 1 H), 7.46 (dd, J=8.3, 2.0 Hz, 1 H), 7.54 (d, J=1.7 Hz, 1 H).

Methyl 1-C-[4-chloro-3-(4-{[(2,6-dichlorophenyl)sulfonyl]oxy}benzyl)phenyl]-6-O-[(2,6-dichlorophenyl)sulfonyl]-alpha-D-glucopyranoside

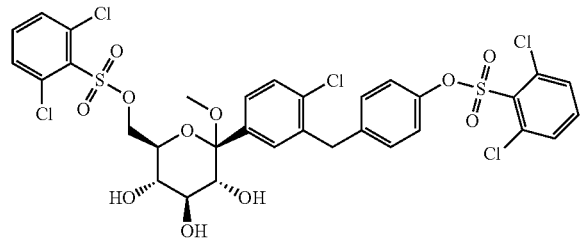 [SMILES: CO[C@@]1(c2ccc(Cl)c(Cc3ccc(OS(=O)(=O)c4c(Cl)cccc4Cl)cc3)c2)O[C@H](COS(=O)(=O)c2c(Cl)cccc2Cl)[C@@H](O)[C@H](O)[C@H]1O]

To a solution of [(2S,3R,4S,5S,6R)-2-[4-chloro-3-(4-hydroxy-benzyl)-phenyl]-6-hydroxymethyl-2-methoxy-tetrahydro-pyran-3,4,5-triol (4.2 g, 10.22 mmol) dissolved in 2-methyl tetrahydrofuran (40 mL) and cooled to 0 degrees Celsius was added triethylamine (4.27 mL, 30.7 mmol), zinc bromide (6.53 g, 26.6 mmol) followed by portionwise addition 2,6-dichlorobenzenesulfonyl chloride (0.610 g, 2.48 mmol). The reaction mixture was warmed to room temperature and allowed to stir overnight (~16 hours). The reaction was quenched by addition of an aqueous solution of 1N hydrochloric acid (100 mL) and water (100 mL). The reaction mixture was extracted using ethyl acetate (100 mL) and the aqueous layer was extracted with ethyl acetate (100 mL) an additional time. The combined organic layers were washed with brine, dried over sodium sulfate, filtered, and concentrated under reduced pressure. 5.6 g (66% yield) of the desired product obtained as an off white solid. $^1$H NMR (400 MHz, METHANOL-d$_4$) delta ppm 3.00 (s, 3 H), 3.03 (d, J=9.4 Hz, 1 H), 3.38 (t, J=9.5 Hz, 1 H), 3.71 (t, J=9.2 Hz, 1 H), 3.79 (ddd, J=10.1, 5.9, 1.5 Hz, 1 H), 4.00-4.14 (m, 2 H), 4.43 (dd, J=10.7, 5.9 Hz, 1 H), 4.55 (dd, J=10.8, 1.5 Hz, 1 H), 7.01 (d, J=8.6 Hz, 2 H), 7.16 (d, J=8.6 Hz, 2 H), 7.24-7.30 (m, 1 H), 7.31-7.36 (m, 1 H), 7.44-7.61 (m, 7 H).

(2S,3R,4S,5S)-2-[4-Chloro-3-(4-hydroxy-benzyl)-phenyl]-6,6-bis-hydroxymethyl-2-methoxy-tetrahydro-pyran-3,4,5-triol

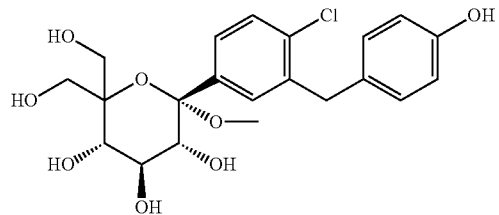 [SMILES: CO[C@@]1(c2ccc(Cl)c(Cc3ccc(O)cc3)c2)OC(CO)(CO)[C@@H](O)[C@H](O)[C@H]1O]

A solution of methyl 1-C-[4-chloro-3-(4-{[(2,6-dichlorophenyl)sulfonyl]oxy}benzyl)phenyl]-6-O-[(2,6-dichlorophenyl)sulfonyl]-alpha-D-glucopyranoside (7 g, 8.44 mmol) dissolved in dimethylsulfoxide (35.3 mL) was placed in a pre-dried 250 mL three neck round bottom flask equipped with a thermometer to monitor internal temperature. To this solution was added 2,4,6-collidine (5.6 mL, 42.2 mmol) and the reaction mixture was heated at 127 degrees Celsius. The internal temperature reached 123 degrees Celsius after 20 minutes, at which point the heating block was turned off and after an additional 20 minutes the flask was removed from the heating block and the reaction mixture was cooled to room temperature and used in the next step without further work-up or purification.

To the above crude solution was added ethanol (70 mL) and the resulting mixture was heated at 55 degrees Celsius. Paraformaldehyde (5090 mg, 169 mmol) was added followed by the addition of 21% sodium ethoxide solution in denatured ethanol (15.8 mL, 42.4 mmol) and the resulting mixture was allowed to stir at 55 degrees Celsius for 16 hours before being cooled to room temperature. The reaction was quenched by the addition of water (125 mL) containing 18 equivalents of $NaHSO_3$ and the resulting mixture was stirred for 90 minutes. The volatiles were removed under reduced pressure. Water (625 mL) was added and the resulting mixture was extracted with ethyl acetate (250 mL). The aqueous layer was extracted 4 times with ethyl acetate. The combined organic layers were washed with brine, dried over sodium sulfate, filtered and concentrated under reduced pressure. The reaction was purified by flash chromatography over silica gel using the ISCO automated chromatography unit (two 120 g silica gel columns) and eluting with a gradient of 5 to 25% methanol in dichloromethane. The crude material was purified by preparative HPLC on a Phenomenex HILIC(Diol) 250×21.2 mm 5 micrometer column eluting with a flow rate of 28 mL/minute; mobile phases A: Heptane and B: Ethanol. The product was eluted using a gradient of 5% ethanol for 1.5 minutes and increased in a linear gradient to 100% ethanol over 8.5 minutes to give the product (586 mg, 16% yield, retention time=9.8 minutes). UV detection: 220 nm. LCMS 439 (M–H$^+$; negative mode)$^1$H NMR (400 MHz, METHANOL-d$_4$) delta ppm 3.03 (d, J=9.6 Hz, 1 H), 3.09 (s, 3 H), 3.74 (d, J=10.0 Hz, 1 H), 3.80 (d, J=11.9 Hz, 1 H), 3.87-3.97 (m, 4 H), 4.00-4.07 (m, 1 H), 4.14 (d, J=11.5 Hz, 1 H), 6.65 (d, J=8.4 Hz, 2 H), 6.98 (d, J=8.4 Hz, 2 H), 7.31 (d, J=8.4 Hz, 1 H), 7.45 (dd, J=8.4, 2.0 Hz, 1 H), 7.50 (d, J=1.8 Hz, 1 H).

(5-bromo-2-chlorophenyl)(4-ethoxyphenyl)methanol

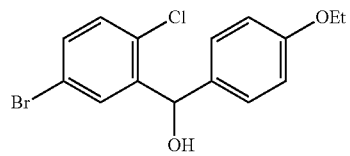 [SMILES: CCOc1ccc(C(O)c2cc(Br)ccc2Cl)cc1]

To a suitable reaction flask was charged (5-bromo-2-chlorophenyl)(4-ethoxyphenyl)methanone (103.06 mmoles, 35.00 g) and acetonitrile (6.68 moles, 350.00 mL, 274.15 g) to afford a clear solution. The solution was cooled to 0 degrees Celsius and sodium borohydride (128.82 mmoles, 4.87 g) was added portionwise. The reaction was stirred for approximately 30 minutes at 0 degrees Celsius, and then at room temperature until completion (as determined by HPLC analysis).

To the reaction mixture was then added water (40 mL), followed by brine (50 mL). The layers were shaken together, allowed to settle and then were separated. The organic phase was concentrated to an oil. Methyl tert-butyl ether (200 mL) was added followed by a slow addition of 1N hydrochloric acid. Vigorous gas evolution was observed. The layers were shaken together, allowed to settle and then were separated. The organic phase was washed with brine (50 mL), dried over magnesium sulfate, filtered and concentrated to afford the crude product as a pale yellow solid (35.38 g, 100% yield). $^1$H-NMR (400 MHz, dimethylsulfoxide-d6) delta 7.84 (d, 1H, J=2.5 Hz), 7.47 (dd, 1H, J=8.5, 2.5 Hz), 7.33 (d, 1H, 8.5 Hz), 7.21 (d, 2H, 8.5 Hz), 6.85 (d, 2H, 8.5 Hz), 5.88 (s, 1H), 3.97 (q, 2H, 7 Hz), 1.29 (t, 3H, 7 Hz).

2-(benzyloxy(4-ethoxyphenyl)methyl)-4-bromo-1-chlorobenzene

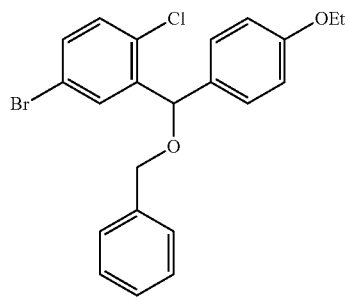 [SMILES: CCOc1ccc(C(OCc2ccccc2)c2cc(Br)ccc2Cl)cc1]

To a suitable reaction flask was charged (5-bromo-2-chlorophenyl)(4-ethoxyphenyl)methanol (5.85 mmoles; 2.00 g) and tetrahydrofuran (245.77 mmoles; 20.00 mL; 17.72 g) to afford a clear solution. Sodium hydride (8.78 mmoles; 351.22 mg) was then added in small portions to minimize the rate of hydrogen gas evolution. The reaction was stirred for approximately 30 minutes at room temperature, and then benzyl bromide (8.78 mmoles; 1.05 mL; 1.50 g) was added slowly. The reaction was allowed to stir at room temperature until completion (as determined by HPLC analysis).

To the reaction mixture was then added 1N hydrochloric acid (10 mL) and ethyl acetate (30 mL). The layers were shaken together, allowed to settle and then were separated. The organic phase was washed with saturated aqueous sodium chloride (10 mL) and then was dried over magnesium sulfate, filtered and concentrated to provide the crude product (3.12 g).

The crude oil was purified by flash chromatography on silica gel eluting with a gradient of 0 to 5% ethyl acetate in hexanes to afford 1.98 g of product as a clear oil (78% yield).

$^1$H-NMR (400 MHz, dimethylsulfoxide-d6) delta 7.78 (d, 1H, J=2.5 Hz), 7.53 (dd, 1H, J=8.5, 2.5 Hz), 7.39 (d, 1H, 8.5 Hz), 7.36-7.25 (m, 7H), 6.90 (m, 2H), 5.72 (s, 1H), 4.48 (m, 2H), 3.99 (q, 2H, 7 Hz), 1.30 (t, 3H, 7 Hz).

$^{13}$C-NMR (100 MHz, dimethylsulfoxide-d6) delta 158.2, 142.0, 137.8, 131.8, 131.5, 131.2, 131.0, 130.2, 128.7, 128.3, 127.6, 127.6, 120.5, 114.3, 77.8, 70.1, 63.0, 14.6.

2-(allyloxy(4-ethoxyphenyl)methyl)-4-bromo-1-chlorobenzene

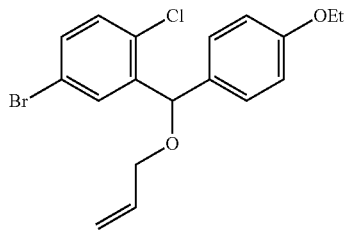 [SMILES: C=CCOC(c1ccc(OCC)cc1)c1cc(Br)ccc1Cl]

To a suitable reaction flask was charged (5-bromo-2-chlorophenyl)(4-ethoxyphenyl)methanol (2.93 mmoles; 1.00 g) and tetrahydrofuran (122.89 mmoles; 10.00 mL; 8.86 g) to afford a clear solution. Sodium hydride (8.14 mmoles; 325.61 mg) was then added in small portions to minimize the rate of hydrogen gas evolution. The reaction was stirred for approximately 30 minutes at room temperature, and then allyl bromide (8.55 mmoles; 0.740 mL; 1.03 g) was added slowly. The reaction was allowed to stir at room temperature until completion (as determined by GCMS analysis).

To the reaction mixture was then added 1N hydrochloric acid (10 mL) and ethyl acetate (20 mL). The layers were shaken together, allowed to settle and then were separated. The organic phase was washed with saturated aqueous sodium chloride (10 mL) and then was dried over magnesium sulfate, filtered and concentrated to provide the crude product (1.07 g).

The crude oil was purified by flash chromatography on silica gel eluting with a gradient of 0 to 5% ethyl acetate in hexanes to afford 858 mg of product as a clear oil (77% yield).

$^1$H-NMR (400 MHz, dimethylsulfoxide-d6) delta 7.75 (d, 1H, J=2.5 Hz), 7.51 (dd, 1H, J=8.5, 2.5 Hz), 7.38 (d, 1H, 8.5 Hz), 7.23 (m, 2H), 6.88 (m, 2H), 5.92 (m, 1H), 5.65 (s, 1H), 5.26 (m, 1H), 5.18 (m, 1H), 4.01-3.93 (m, 4H), 1.30 (t, 3H, 7 Hz).

$^{13}$C-NMR (100 MHz, dimethylsulfoxide-d6) delta 158.6, 142.5, 135.1, 132.2, 131.9, 131.6, 131.3, 130.4, 129.1, 120.8, 117.3, 114.7, 77.9, 69.4, 63.4, 15.0.

((5-bromo-2-chlorophenyl)(4-ethoxyphenyl)methoxy)(tert-butyl)dimethylsilane

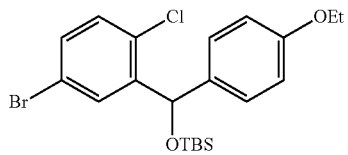 [SMILES: CCOc1ccc(C(O[Si](C)(C)C(C)(C)C)c2cc(Br)ccc2Cl)cc1]

To a suitable reaction flask was charged (5-bromo-2-chlorophenyl)(4-ethoxyphenyl)methanol (2.93 mmoles; 1.00 g) and tetrahydrofuran (122.89 mmoles; 10.00 mL; 8.86 g) to afford a clear solution. Triethylamine (3.81 mmoles; 0.530 mL; 385.06 mg) was then added via syringe, followed by tert-butyl dimethylsilyl trifluoromethanesulfonate (3.81 mmoles; 0.875 mL; 1.01 g) at room temperature. The reaction was allowed to stir at room temperature until completion (as determined by GCMS analysis).

To the reaction mixture was then added deionized water (10 mL) and ethyl acetate (20 mL). The layers were shaken together, allowed to settle and then were separated. The organic phase was washed with saturated aqueous sodium chloride (10 mL) and then was dried over magnesium sulfate, filtered and concentrated to provide the crude product (1.45 g).

The crude oil was purified by flash chromatography on silica gel eluting with a gradient of 0 to 5% ethyl acetate in hexanes to afford 1.00 g of product as a clear oil (75% yield).

$^1$H-NMR (400 MHz, dimethylsulfoxide-d6) delta 7.81 (d, 1H, J=2.5 Hz), 7.46 (dd, 1H, J=8.5, 2.5 Hz), 7.34 (d, 1H, 8.3 Hz), 7.24 (m, 2H), 6.85 (m, 2H), 6.00 (s, 1H), 3.95 (q, 2H, 7 Hz), 1.28 (t, 3H, 7 Hz), 0.85 (s, 9H), −0.02 (s, 3H), −0.06 (s, 3H).

$^{13}$C-NMR (100 MHz, dimethylsulfoxide-d6) delta 157.8, 144.5, 134.0, 131.5, 131.2, 130.3, 129.7, 127.6, 120.3, 114.1, 71.7, 62.9, 25.5, 17.8, 14.6, −5.0, −5.2.

Example 1

(1S,2S,3S,4R,5S)-5-[4-chloro-3-(4-hydroxy-benzyl)-phenyl]-1-hydroxymethyl-6,8-dioxa-bicyclo[3.2.1]octane-2,3,4-triol

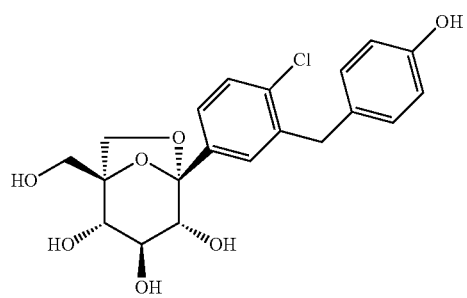 [SMILES: OC[C@@]12CO[C@@](c3ccc(Cl)c(Cc4ccc(O)cc4)c3)(O1)[C@H](O)[C@@H](O)[C@@H]2O]

To a solution of (2S,3R,4S,5S)-2-[4-Chloro-3-(4-hydroxy-benzyl)-phenyl]-6,6-bis-hydroxymethyl-2-methoxy-tetrahydro-pyran-3,4,5-triol (580 mg, 1.32 mmol) in a mixture of dichloromethane (5 mL) of and 2-methyltetrahydrofuran (5 mL) was added Silicycle® Si-Tosic acid derivatized silica gel (40-63 micrometer, 0.68 mmol/g) Silicagel bound toluenesulfonic acid (1 g) and the reaction mixture was allowed to stir at room temperature overnight (~16 hours). The mixture was filtered through a plug of Celite® and the plug rinsed with dichloromethane:2-methyl-tetrahydrofuran (40 mL; 1:1 volume). The crude material was purified by preparative HPLC on a Phenomenex Gemini NX 150×21.2 5 mm column eluting with a flow rate of 28 mL/minute; mobile phases A: water with 1% ammonium hydroxide modifier and B: methanol with 1% ammonium hydroxide modifier. The product was eluted using a gradient of 5% methanol with 1% ammonium hydroxide modifier for 1.5 minutes and increased in a linear gradient to 100% methanol with 1% ammonium hydroxide modifier over 8.5 minutes to give the product (375 mg; 69.7% yield, retention time=9.8 minute). LCMS 407 (M−H$^+$, negative mode). $^1$H NMR (500 MHz, METHANOL-d4) delta ppm 3.56 (d, J=7.8 Hz, 1 H), 3.61 (d, J=7.3 Hz, 1 H), 3.66 (t, J=8.2 Hz, 1 H), 3.69 (d, J=12.4 Hz, 1 H), 3.79 (d, J=8.3 Hz, 1 H), 3.85 (d, J=12.4 Hz, 1 H), 4.01 (s, 2 H), 4.16 (d, J=7.3 Hz, 1 H), 6.69 (d, J=8.3 Hz, 2 H), 7.02 (d, J=8.3 Hz, 2 H), 7.34-7.37 (m, 1 H), 7.37-7.41 (m, 1 H), 7.45 (d, J=1.5 Hz, 1 H).

Example 2

Acetic acid (1R,2S,3S,4R,5S)-3,4-diacetoxy-1-acetoxymethyl-5-[4-chloro-3-(4-ethoxy-benzyl)-phenyl]-6,8-dioxa-bicyclo[3.2.1]oct-2-yl ester

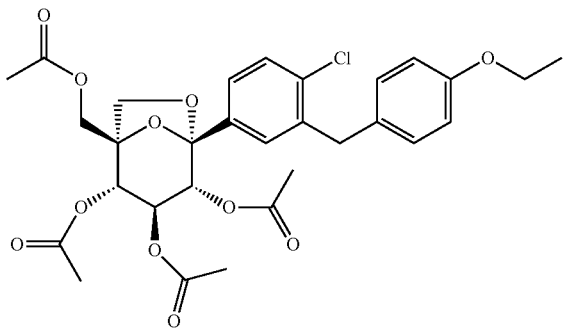 [SMILES: CCOc1ccc(Cc2cc([C@]34OC[C@](COC(C)=O)(O3)[C@@H](OC(C)=O)[C@H](OC(C)=O)[C@H]4OC(C)=O)ccc2Cl)cc1]

To a solution of (1S,2S,3S,4R,5S)-5-[4-Chloro-3-(4-ethoxy-benzyl)-phenyl]-1-hydroxymethyl-6,8-dioxa-bicyclo[3.2.1]octane-2,3,4-triol (1A, 1.22 g, 2.792 mmol) in tetrahydrofuran (10 mL) cooled to 0 degrees Celsius were added N,N-diisopropylethylamine (3.5 mL, 20 mmol) and 4-dimethylaminopyridine (0.25 g, 2.0 mmol). Acetic anhydride (1.58 mL, 16.8 mmol) was slowly added so that the temperature did not exceed 10 degrees Celsius and the resulting solution was warmed to room temperature and stirred overnight (~16 hours). Ethyl acetate and a aqueous solution of 1N hydrochloric acid were added, the organic phase was separated and the aqueous phase was extracted three times with ethyl acetate. The combined organic layers were washed with brine, dried over magnesium sulfate, filtered, and concentration under reduced pressure. The crude product was purified by flash chromatography over silica gel using the biotage automated chromatography unit (50 g silica gel column) and eluting with 0 to 100% ethyl acetate in heptane. The product was recrystallized using hot methanol (30 mL) and allowing the material to cool forming small white shards. The white solid was filtered and washed with 50 mL of cold methanol yielding 590 mg (35% yield) of crystalline white solid (mp 134.3 degrees Celsius).

(LCMS) 622.4 (M+NH$_4^+$; positive mode). $^1$H NMR (400 MHz, CHLOROFORM-d) delta ppm 1.39 (t, J=7.03 Hz, 3 H), 1.69 (s, 3 H), 1.98 (s, 3 H), 2.04 (s, 3 H), 2.09 (s, 3 H), 3.70 (dd, J=8.10, 1.46 Hz, 1 H), 3.93-4.02 (m, 2 H), 3.99 (d, J=7.03 Hz, 2 H), 4.08 (d, J=15.20 Hz, 1 H), 4.42 (d, J=8.20 Hz, 1 H), 4.53 (d, J=12.50 Hz, 1 H), 5.28 (d, J=8.01 Hz, 1 H), 5.39 (t, J=8.30 Hz, 1 H), 5.48 (dd, J=8.6, 1 Hz, 1 H), 6.80 (d, J=8.79 Hz, 2 H), 7.06 (d, J=8.79 Hz, 2 H), 7.30-7.37 (m, 3 H).

The filtrate was concentrated under reduced pressure. To the solid was added methanol (~15 mL) and the mixture was heated until the solid dissolved. The solution was allowed to cool and to this solution were added seed crystals. The resulting white crystalline shards were filtered and collected yielding additional 577 mg (34% yield) of crystalline white solid.

Example 3

Acetic acid (1R,2S,3S,4R,5S)-5-[4-chloro-3-(4-ethoxy-benzyl)-phenyl]-2,3,4-trihydoxy-6,8-dioxa-bicyclo[3.2.1]oct-1-ylmethyl ester

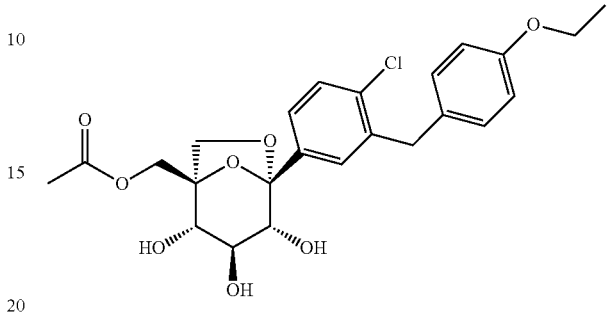

To a vigorously stirred solution of (1S,2S,3S,4R,5S)-5-[4-Chloro-3-(4-ethoxy-benzyl)-phenyl]-1-hydroxymethyl-6,8-dioxa-bicyclo[3.2.1]octane-2,3,4-triol (1A, 0.481 g, 1.1 mmol) in collidine (2.5 mL) cooled to −35 degrees Celsius was added drop-wise over 10 minutes acetyl chloride (0.149 mL, 2.1 mmol). After 1 hour, methanol (0.5 mL) was added and the reaction mixture was allowed to warm to room temperature. The crude mixture was concentrated under reduced pressure and codistilled three times with toluene. The crude material was purified by flash chromatography over silica gel using the biotage automated chromatography unit (50 g silica gel column) and eluting with a gradient of 0 to 15% methanol in dichloromethane. 456 mg (87% yield) of product obtained as a white solid.

(LCMS) 523.3 (M+HCOO$^-$: negative mode). $^1$H NMR (400 MHz, METHANOL-d$_4$) delta ppm 1.35 (t, J=6.93 Hz, 3 H), 2.05 (s, 3 H), 3.52 (d, J=7.81 Hz, 1 H), 3.59 (dd, J=7.71, 1.46 Hz, 1 H), 3.63 (t, J=8.10 Hz, 1 H), 3.76 (dd, J=8.30, 1.27 Hz, 1 H), 3.98 (q, J=6.96 Hz, 2 H), 4.03 (s, 2 H), 4.17 (d, J=12.7 Hz, 1 H), 4.19 (d, J=8 Hz, 1 H), 4.41 (d, J=12.30 Hz, 1 H), 6.80 (d, J=8.79 Hz, 2 H), 7.08 (d, J=8.79 Hz, 2 H), 7.34-7.36 (m, 2 H), 7.40 (s, 1 H).

Example 4

Carbonic acid (1R,2S,3S,4R,5S)-5-[4-chloro-3-(4-ethoxy-benzyl)-phenyl]-2,3,4-trihydoxy-6,8-dioxa-bicyclo[3.2.1]oct-1-ylmethyl ester ethyl ester

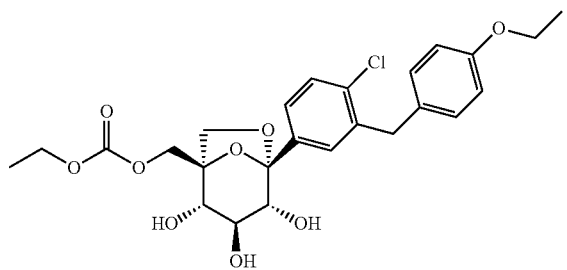 [SMILES: CCOC(=O)OC[C@@]12CO[C@@](c3ccc(Cl)c(Cc4ccc(OCC)cc4)c3)(O1)[C@H](O)[C@@H](O)[C@@H]2O]

To a vigorously stirred solution of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (1A, 288 mg, 0.659 mmol) in collidine (6.6 mL) cooled to −35 degrees Celsius was added drop-wise over 10 minutes ethylchloroformate (0.112 mL, 1.19 mmol). The reaction mixture was allowed to stir overnight at room temperature. The reaction was quenched with an aqueous solution of saturated citric acid and extracted with ethyl acetate (2 times). The combined organic layers were washed with brine, dried over magnesium sulfate, filtered and concentrated under reduced pressure. The crude material was purified by flash chromatography over silica gel using the biotage automated chromatography unit (50 g silica gel column) and eluting with a gradient of 0 to 20% methanol in dichloromethane. 134 mg (40% yield) of desired product as a white solid.

(LCMS) 526 (M+$NH_4^+$: positive mode). $^1$H NMR (400 MHz, METHANOL-$d_4$) delta ppm 1.25 (t, J=7.1 Hz, 3 H), 1.35 (t, J=7.0 Hz, 3 H), 3.52 (d, J=7.8 Hz, 1 H), 3.59 (d, J=7.8 Hz, 1 H), 3.61-3.66 (m, 1 H), 3.76 (d, J=8.2 Hz, 1 H), 3.98 (q, J=7.0 Hz, 2 H), 4.03 (s, 2 H), 4.15 (q, 2 H), 4.19 (d, J=7.8 Hz, 1 H), 4.23 (d, J=11.9 Hz, 1 H), 4.46 (d, J=12.1 Hz, 1 H), 6.79 (d, J=8.6 Hz, 2 H), 7.08 (d, J=8.4 Hz, 2 H), 7.35 (s, 2 H), 7.42 (s, 1 H).

Example 5

[$D_5$]-(1S,2S,3S,4R,5S)-5-[4-chloro-3-(4-ethoxy-benzyl)-phenyl]-1-hydroxymethyl-6,8-dioxa-bicyclo [3.2.1]octane-2,3,4-triol

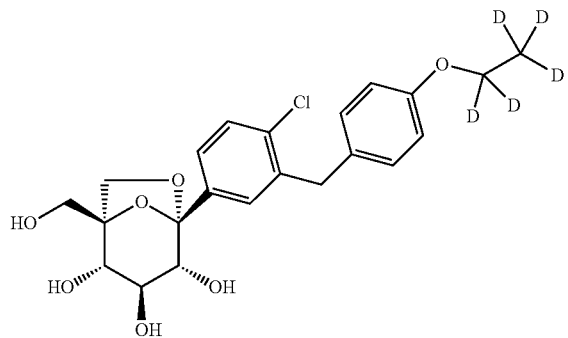 [SMILES: [2H]C([2H])([2H])C([2H])([2H])Oc1ccc(Cc2cc([C@]34OC[C@](CO)(O3)[C@@H](O)[C@H](O)[C@H]4O)ccc2Cl)cc1]

To a solution of (1S,2S,3S,4R,5S)-5-[4-chloro-3-(4-hydroxy-benzyl)-phenyl]-1-hydroxymethyl-6,8-dioxa-bicyclo [3.2.1]octane-2,3,4-triol (54 mg, 0.13 mmol) in acetonitrile (0.5 mL) was added potassium carbonate (55 mg, 0.40 mmol) followed by the addition of iodoethane-d5 (0.016 mL, 0.198 mmol). The reaction mixture was allowed to stir at room temperature for 4 hours and was then heated to 50 degrees Celsius for 16 hours. The reaction was quenched with water (20 mL) and the resulting mixture was extracted 3 times with ethyl acetate (20 mL). The combined organic layers were washed with brine, dried over sodium sulfate, filtered and concentrated under reduced pressure. The crude material was purified by flash chromatography using the ISCO automated chromatography unit (4 g silica gel column) eluting with a gradient of 0 to 23% methanol in dichloromethane. 28.3 mg (48% yield) of the desired product was obtained as a white solid. LCMS 486 (M+$HCO_2^-$, negative mode). $^1$H NMR (400 MHz, METHANOL-d4) delta ppm 3.52 (d, J=7.8 Hz, 1 H), 3.57 (dd, J=7.4, 1.0 Hz, 1 H), 3.62 (t, J=7.8 Hz, 1 H), 3.66 (d, J=12.3 Hz, 1 H), 3.75 (d, J=8.2 Hz, 1 H), 3.81 (d, J=12.5 Hz, 1 H), 4.01 (s, 2 H), 4.12 (d, J=7.4 Hz, 1 H), 6.77 (d, J=8.8 Hz, 2 H), 7.06 (d, J=8.6 Hz, 2 H), 7.31-7.34 (m, 1 H), 7.34-7.39 (m, 1 H), 7.43 (d, J=1.8 Hz, 1 H).

Example 6

Acetic acid 2-{4-[2-chloro-5-((1S,2S,3S,4R,5S)-2,3,4-trihydroxy-1-hydroxymethyl-6,8-dioxa-bicyclo [3.2.1]oct-5-yl)-benzyl]-phenoxy}-ethyl ester

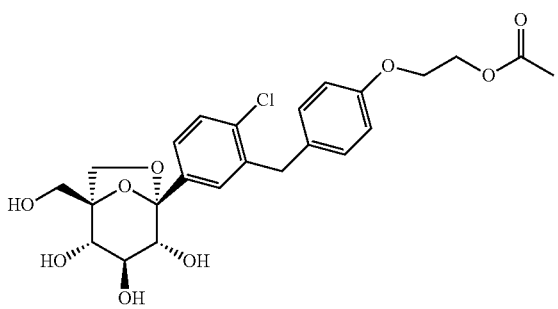 [SMILES: CC(=O)OCCOc1ccc(Cc2cc([C@]34OC[C@](CO)(O3)[C@@H](O)[C@H](O)[C@H]4O)ccc2Cl)cc1]

To a solution of (1S,2S,3S,4R,5S)-5-[4-chloro-3-(4-hydroxy-benzyl)-phenyl]-1-hydroxymethyl-6,8-dioxa-bicyclo [3.2.1]octane-2,3,4-triol (38 mg, 0.093 mmol) in acetonitrile (0.9 mL) was added potassium carbonate (40 mg, 0.28 mmol) followed by the addition of acetic acid 2-bromo-ethyl ester (0.012 mL, 0.112 mmol) and the resulting mixture was heated to 50 degrees Celsius for 72 hours. The reaction showed some product formation but the majority of starting material remained. An additional 2 equivalents of acetic acid 2-bromo-ethyl ester was added and the mixture was heated at 50 degrees Celsius for an additional 24 hours. Water (20 mL) and ethyl acetate were added, the two phases separated and the aqueous phase was extracted 3 times with ethyl acetate (20 mL). The combined organic layers were washed with brine, dried over sodium sulfate, filtered and concentrated under reduced pressure. The crude material was purified by flash chromatography over silica gel using the ISCO automated chromatography unit (4 g silica gel column) and eluting with a gradient of 0 to 30% methanol in dichloromethane. 10 mg (22% yield) of a ~2:1 mixture of the desired product contaminated with some unidentified compound was obtained. LCMS 539 M+HCOO$^-$, negative mode).

The compound was purified by HPLC on a Phenomenex Lux Cellulose-2 5u column eluting with a flow rate of 28 mL/min. and a mobile phases A: heptane and B: ethanol. The product was eluted using a gradient of 5% ethanol for 2 minutes and increased to 100% ethanol at time 10.0 minutes to give 1.1 mg of the desired product.

(LCMS positive mode M+Na+=517)
$^1$H NMR (500 MHz, METHANOL-d4) delta ppm 2.07 (s, 3 H), 3.56 (d, J=7.8 Hz, 1 H), 3.58-3.63 (m, 1 H), 3.64-3.72 (m, 2 H), 3.79 (d, 1 H), 3.85 (d, J=12.4 Hz, 1 H), 4.06 (s, 2 H), 4.13-4.19 (m, 3 H), 4.36-4.41 (m, 2 H), 6.82-6.88 (m, 2 H), 7.09-7.15 (m, 2 H), 7.35-7.43 (m, 2 H), 7.47 (d, J=2.2 Hz, 1 H). LCMS (ES): 495.4 (M+H$^+$).

Example 7

(1S,2S,3S,4R,5S)-5-{4-Chloro-3-[4-(2-hydroxy-ethoxy)-benzyl]-phenyl}-1-hydroxymethyl-6,8-dioxa-bicyclo[3.2.1]octane-2,3,4-triol

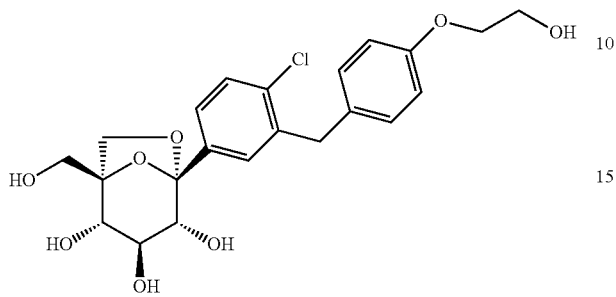

To a solution of (1S,2S,3S,4R,5S)-5-[4-chloro-3-(4-hydroxy-benzyl)-phenyl]-1-hydroxymethyl-6,8-dioxa-bicyclo[3.2.1]octane-2,3,4-triol (14 mg, 0.034 mmol) in acetonitrile (0.5 mL) was added potassium carbonate (14 mg, 0.1 mmol) followed by the addition of (2-bromo-ethoxymethyl)-benzene (0.010 mL, 0.063 mmol) and the reaction mixture was heated to 50 degrees Celsius for 24 hours. The reaction showed some product formation but the majority of starting material remained. An additional 3 equivalents of potassium carbonate was added, the temperature was increased to 83 degrees Celsius and the reaction mixture stirred for an additional 5 hours. The reaction mixture was cooled to room temperature, water (20 mL) and ethyl acetate were added, the organic phase separated and the aqueous phase was extracted 3 times with ethyl acetate (20 mL). The combined organic layers were washed with brine, dried over sodium sulfate, filtered and concentrated under reduced pressure. The crude material was purified by flash chromatography over silica gel using the ISCO automated chromatography unit (4 g silica gel column) and eluting with a gradient of 0 to 23% methanol in dichloromethane. 4 mg of the desired compound (1S,2S,3S,4R,5S)-5-(3-(4-(2-(Benzyloxy)ethoxy)benzyl)-4-chlorophenyl)-1-(hydroxymethyl)-6,8-dioxabicyclo[3.2.1]octane-2,3,4-triol was obtained. LCMS 587 (M+HCO$_2^-$, negative mode). $^1$H NMR (500 MHz, METHANOL-d4) delta ppm 3.56 (d, J=8.1 Hz, 1 H), 3.60 (d, J=7.6 Hz, 1 H), 3.63-3.67 (m, 1 H), 3.69 (d, J=12.7 Hz, 2 H), 3.79 (d, J=8.3 Hz, 1 H), 3.82 (d, J=4.6 Hz, 1 H), 3.83-3.87 (m, 1 H), 4.05 (s, 2 H), 4.11-4.14 (m, 2 H), 4.16 (d, J=7.3 Hz, 1 H), 4.62 (s, 2 H), 6.86 (d, J=8.5 Hz, 2 H), 7.12 (d, J=8.5 Hz, 2 H), 7.29 (d, J=7.1 Hz, 1 H), 7.31-7.43 (m, 6 H), 7.47 (s, 1 H).

To a solution of intermediate (1S,2S,3S,4R,5S)-5-(3-(4-(2-(Benzyloxy)ethoxy)benzyl)-4-chlorophenyl)-1-(hydroxymethyl)-6,8-dioxabicyclo[3.2.1]octane-2,3,4-triol (4 mg, 0.007 mmol) in a mixture of ethanol and tetrahydrofurane (1 mL, 4 to 1 in volume) was successively added formic acid (12 microL, 0.30 mmol) and palladium black (7.5 mg, 0.07 mmol). The reaction mixture was stirred at room temperature for 2 hours, the palladium was filtered through a pad of Celite®, the filtrate was evaporated and the residue was dried under high vacuum to afford 2.6 mg (80% yield) of the desired product. LCMS 453.5 (M+H$^+$; positive mode). $^1$H NMR (500 MHz, METHANOL-d$_4$) delta ppm 3.56 (d, J=7.8 Hz, 1 H), 3.58-3.72 (m, 4 H), 3.79 (d, J=7.8 Hz, 1 H), 3.82-3.88 (m, 2 H), 4.02 (t, J=4.9 Hz, 2 H), 4.05 (s, 2 H), 4.16 (d, J=7.6 Hz, 1 H), 6.84-6.89 (m, 2 H), 7.11 (d, J=8.5 Hz, 2 H), 7.35-7.42 (m, 2 H), 7.47 (d, J=2.0 Hz, 1 H).

Example 8

(1S,2S,3S,4R,5S)-5-[4-Chloro-3-(4-ethoxy-benzyl)-phenyl]-1-fluoromethyl-6,8-dioxa-bicyclo[3.2.1]octane-2,3,4-triol

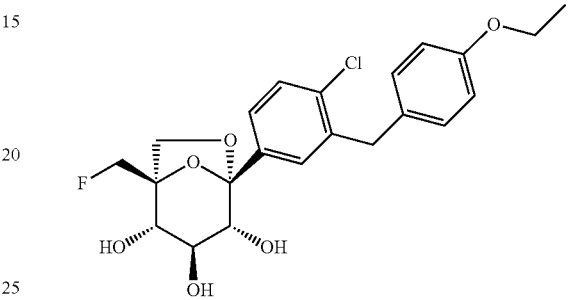

To a solution of {(1S,2S,3S,4R,5S)-2,3,4-Tris-benzyloxy-5-[4-chloro-3-(4-ethoxy-benzyl)-phenyl]-6,8-dioxa-bicyclo[3.2.1]oct-1-yl}-methanol (616 mg, 0.871 mmol) in dichloromethane (3 mL) at 0 degrees Celsius was added diethylaminosulfur trifluoride (170 microL, 1.3 mmol) and the resulting mixture was slowly warmed to room temperature and stirred at this temperature for 16 hours. The mixture was diluted with dichloromethane and washed with a saturated solution of aqueous sodium bicarbonate, dried over sodium sulfate, filtered and concentrated in vacuo. The residue was purified by flash chromatography over silica gel using a 40 g redisep silica cartridge (eluting with a gradient of 0 to 20% ethyl acetate in heptane) to afford (1S,2S,3S,4R,5S)-2,3,4-tris-benzyloxy-5-[4-chloro-3-(4-ethoxy-benzyl)-phenyl]-1-fluoromethyl-6,8-dioxa-bicyclo[3.2.1]octane as a colorless oil (40 mg, 7% yield). (LCMS) 753.4 (M+HCOO$^-$: negative mode).

To a suspension of (1S,2S,3S,4R,5S)-2,3,4-tris-benzyloxy-5-[4-chloro-3-(4-ethoxy-benzyl)-phenyl]-1-fluoromethyl-6,8-dioxa-bicyclo[3.2.1]octane (40 mg, 0.06 mmol) and palladium black (40 mg, 0.38 mmol, Aldrich® high surface area) in ethanol (0.5 mL) and tetrahydrofuran (0.1 mL) was added formic acid (0.085 mL, 2.24 mmol) and the resulting mixture was stirred at room temperature for 1.5 hours. Ethyl acetate was added and the mixture was filtered through a short pad of Celite® and concentrated in vacuo. The crude material was purified by flash chromatography over silica gel using a 4 g redisep silica cartridge (eluting with a gradient of 50 to 100% ethyl acetate in heptane) to afford the title compound as a solid (15.6 mg, 63% yield). (LCMS) 483.0 (M+HCOO$^-$: negative mode). $^1$H NMR (500 MHz, METHANOL-d$_4$) delta ppm 7.44 (s, 1 H), 7.38 (s, 1 H), 7.37 (s, 1 H), 7.09-7.12 (m, 2 H), 6.80-6.83 (m, 2 H), 4.71 (dd, J=46.59, 10.49 Hz, 1 H), 4.50 (dd, J=48.30, 10.73 Hz, 1 H), 4.19 (dd, J=7.56, 0.98 Hz, 1 H), 4.04 (d, J=0.98 Hz, 2 H), 4.00 (q, J=6.99 Hz, 2 H), 3.80 (dd, J=8.29, 0.98 Hz, 1 H), 3.67 (t, J=8.17 Hz, 1 H), 3.54-3.57 (m, 2 H), 1.37 (t, 3 H).

Example 9

(1S,2S,3S,4R,5S)-5-{4-chloro-3-[(4-ethoxy-phenyl)-hydroxy-methyl]-phenyl}-1-hydroxymethyl-6,8-dioxa-bicyclo[3.2.1]octane-2,3,4-triol

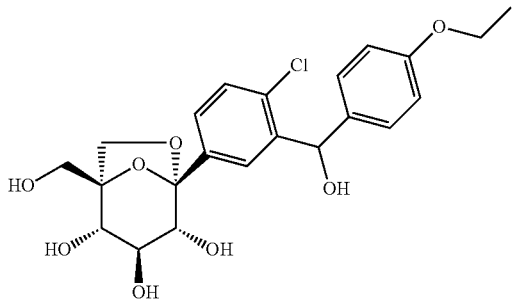 [SMILES: CCOc1ccc(C(O)c2cc([C@]34OC[C@](CO)(O3)[C@@H](O)[C@H](O)[C@H]4O)ccc2Cl)cc1]

To a solution of acetic acid (1R,2S,3S,4R,5S)-3,4-diacetoxy-1-acetoxymethyl-5-[4-chloro-3-(4-ethoxy-benzoyl)-phenyl]-6,8-dioxa-bicyclo[3.2.1]oct-2-yl ester (see Example 11 for preparation; 85 mg, 0.14 mmol) in methanol (3 mL) was added sodium borohydride (25 mg, 0.66 mmol) at room temperature. After one hour, the reaction was quenched by the addition of water (20 mL) and the resulting mixture was concentrated under reduced pressure. The resulting aqueous layer was extracted three times with ethyl acetate (15 mL). The combined organic layers were washed with brine, dried over sodium sulfate, filtered and concentrated under reduced pressure. To a solution of this crude material in methanol (5 mL) was added sodium methoxide in methanol (25% wt) until pH 12 was obtained and the resulting mixture was stirred at room temperature. After 16 hours, the reaction mixture was neutralized by the addition of Dowex Monosphere 650C (H) cation exchange resin (the resin was washed with methanol 3 times before use) until the pH of the solution was <7. The reaction mixture was filtered and concentrated under reduced pressure. The resulting material was precipitated from ethyl acetate and heptane. The resulting solid was washed with heptane 2 times and dried under reduced pressure to yield the desired product (58.9 mg, 93% yield) as a white solid. MS (LCMS) 497.3 (M–HCOO⁻, negative mode)¹H NMR (400 MHz, METHANOL-$d_4$) delta ppm 1.33 (t, J=6.9 Hz, 6 H), 3.56 (d, J=8.0 Hz, 1 H), 3.59-3.64 (m, 3 H), 3.64-3.69 (m, 2 H), 3.68 (d, J=12.5 Hz, 2 H), 3.78 (d, J=8.2 Hz, 2 H), 3.84 (d, J=12.5 Hz, 2 H), 3.98 (q, J=7.0 Hz, 4 H), 4.15 (d, J=7.4 Hz, 1 H), 4.16 (d, J=7.4 Hz, 1 H), 6.04 (s, 1 H), 6.05 (s, 1 H), 6.80 (d, J=8.4 Hz, 4 H), 7.21 (d, J=8.6 Hz, 2 H), 7.22 (d, J=8.6 Hz, 2 H), 7.29 (d, J=8.2 Hz, 2 H), 7.40-7.42 (m, 2 H), 7.91 (d, J=2.0 Hz, 1 H), 7.93 (d, J=2.0 Hz, 1 H).

Analytical method: Column: Chiralpak AD-H (4.6 mm×25 cm), Flow rate: 2.5 mL/minute, mobile phase: 65/35 $CO_2$/propanol; UV detection: 210 nm. Peak 1 ($R_t$=2.80 minutes, 45.5% area), Peak 2 (R=5.51 minutes, 54.5% area).

As depicted in Scheme 6, Example 9 could also be prepared according to the procedures described in steps 1 to 6 of Scheme 2 using the appropriate organometallic reagent (IX-1) wherein M is Li or Mg, X' is Cl, Br or I and p is 0-2 ($R^7$ is OPMB, OBn, OTBS, OTMS, OTES, OTIPS, OAllyl, OBOM, OPMBM, ODMBM, OMOM, OMEM, OMTM, OSEM, OM(X')$_p$ or any suitably protected precursor to the claimed compound example 9).

Scheme 6

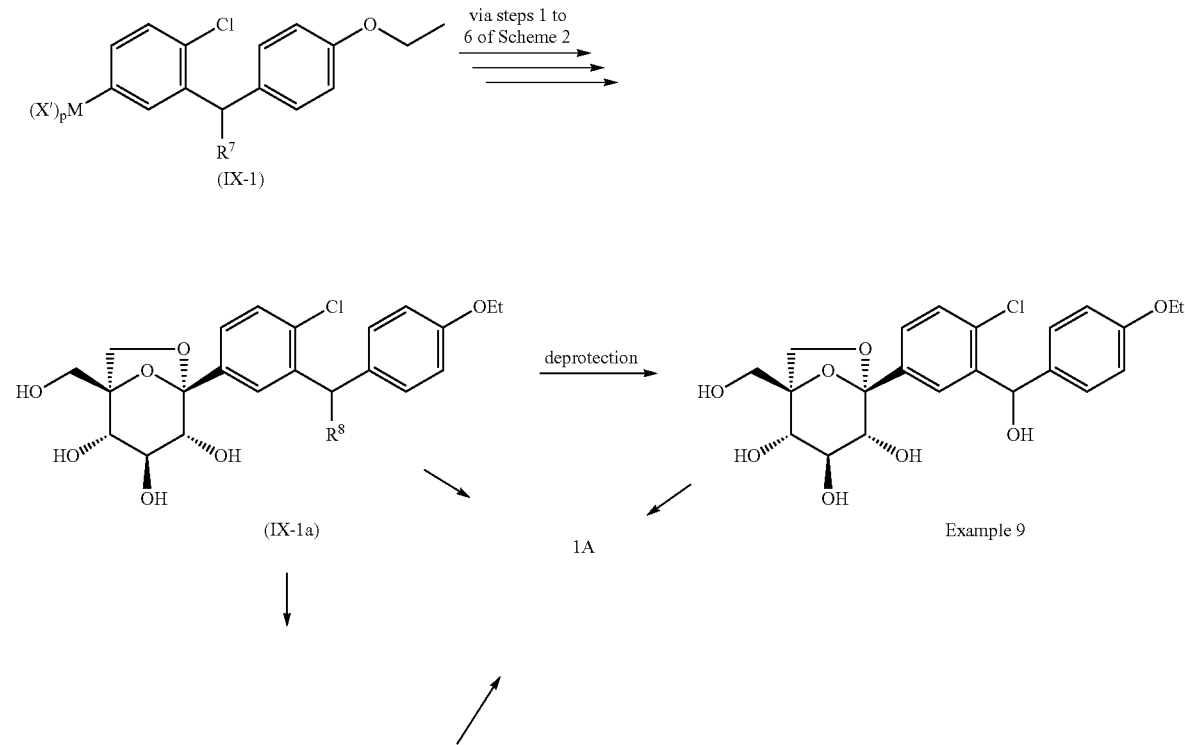

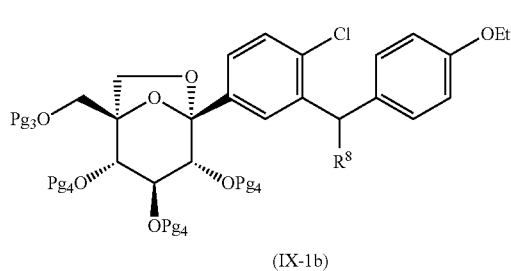

(IX-1b)

Depending on $R^8$ ($R^8$ is OPMB, OBn, OTBS, OTMS, OTES, OTIPS, OAllyl, OBOM, OPMBM, ODMBM, OMOM, OMEM, OMTM, OSEM, OH or any suitably protected precursor to the claimed compound example 9), the compounds of general structure (IX-1a) obtained from the synthetic route exemplified in Scheme 2 (steps 1 to 6) could be easily converted to Example 9 from the present invention using well known protecting group manipulation sequences known by those skilled in the art. For a general description of protecting groups and their use, see T. W. Greene, *Protective Groups in Organic Synthesis*, John Wiley & Sons, New York, 1991. In the event that compound (IX-1a) is submitted to hydrogenolysis conditions (such conditions could be but are not limited to: Pd black in the presence of formic acid in an alcoholic solvent such as ethanol with the optional presence of a co-solvent such as tetrahydrofuran at a temperature ranging from about 0 to about 50 degrees Celsius; alternative conditions could involve the use of Pd—C or Pd(OH)$_2$ as catalysts under a hydrogen gas atmosphere in an alcoholic solvent such as ethanol with the optional presence of a co-solvent such as tetrahydrofuran at a temperature ranging from about 0 to about 50 degrees Celsius and with the optional presence of an acid like acetic acid, trifluoroacetic acid, hydrochloric acid or formic acid), then compound 1A could be obtained instead of Example 9. Alternatively, compound 1A could be obtained by treatment of a solution of (IX-1a) in a solvent such as dichloromethane with a silicon hydride derivative such as triethylsilane in the presence of an acid such as trifluoroacetic acid, formic acid or boron trifluoride diethyletherate at a temperature ranging from about −30 degrees to about 23 degrees Celsius (for a general protocol, see the procedure described in example VII of PCT Publication No. WO 06/089872). The compound 1A thus obtained could be converted to Example 9 via Example 2 following the procedures described in the experimental section.

It may also be advantageous to protect the hydroxyl groups on the dioxa-bicyclo[3.2.1]octane motif. Someone skilled in the art would recognize that compound (IX-1b) could be accessed from (IX-1a) by selective protection of the primary hydroxyl group with a suitable protecting group (Pg$_3$) followed by protection of the remaining secondary hydroxyl groups with suitable protecting groups (Pg$_4$) following similar procedures, for the particular protecting groups chosen, as described in steps 1 and 2 of Scheme 3. For a general description of hydroxyl protecting groups and their use in chemical synthesis, see T. W. Greene, *Protective Groups in Organic Synthesis*, John Wiley & Sons, New York, 1991. In the case where Pg$_3$=Pg$_4$ the protection could be conducted in one step. Functional group manipulation as described for (IX-1a) applied to (IX-1 b) followed by removal of the remaining protecting groups (Pg$_3$) and (Pg$_4$) using the appropriate chemistry for the particular protecting groups could lead to 1A.

The organometallic reagent (IX-1) could be synthesized from the corresponding aryl halide (IX-2) or (IX-3) using protocols of halogen-metal exchange known by those skilled in the art (see experimental section; for an example of halogen-metal exchange followed by nucleophilic addition to a benzaldehyde derivative, see example VI of PCT Publication No. WO 06/089872). The starting aryl halide can be synthesized as follows (see Scheme 7): nucleophilic addition (for an example of nucleophilic addition of an organometallic reagent to a benzaldehyde derivative see: example VI of PCT Publication No. WO 06/089872) of 4-ethoxyphenylmagnesium bromide (Rieke Metals, Inc) or 4-ethoxyphenyllithium (readily available by lithium-halogen exchange starting from 1-ethoxy-4-iodobenzene (TCI America) or 1-bromo-4-ethoxybenzene (TCI America)) to 5-Bromo-2-chlorobenzaldehyde (Apollo Scientific Ltd.) could lead to (5-bromo-2-chlorophenyl)(4-ethoxyphenyl) methanol, which following protection of the resulting hydroxyl group (following protocols known by those skilled in the art; see examples section for further details as well as T. W. Greene, *Protective Groups in Organic Synthesis*, John Wiley & Sons, New York, 1991) would afford aryl halide (IX-2). In a similar fashion aryl halide (IX-3) can be produced from (2-chloro-5-iodophenyl)(4-ethoxyphenyl) methanol starting from 2-chloro-5-iodobenzaldehyde (Aldlab Chemicals, LLC) and 4-ethoxyphenylmagnesium bromide or 4-ethoxyphenyllithium.

Scheme 7

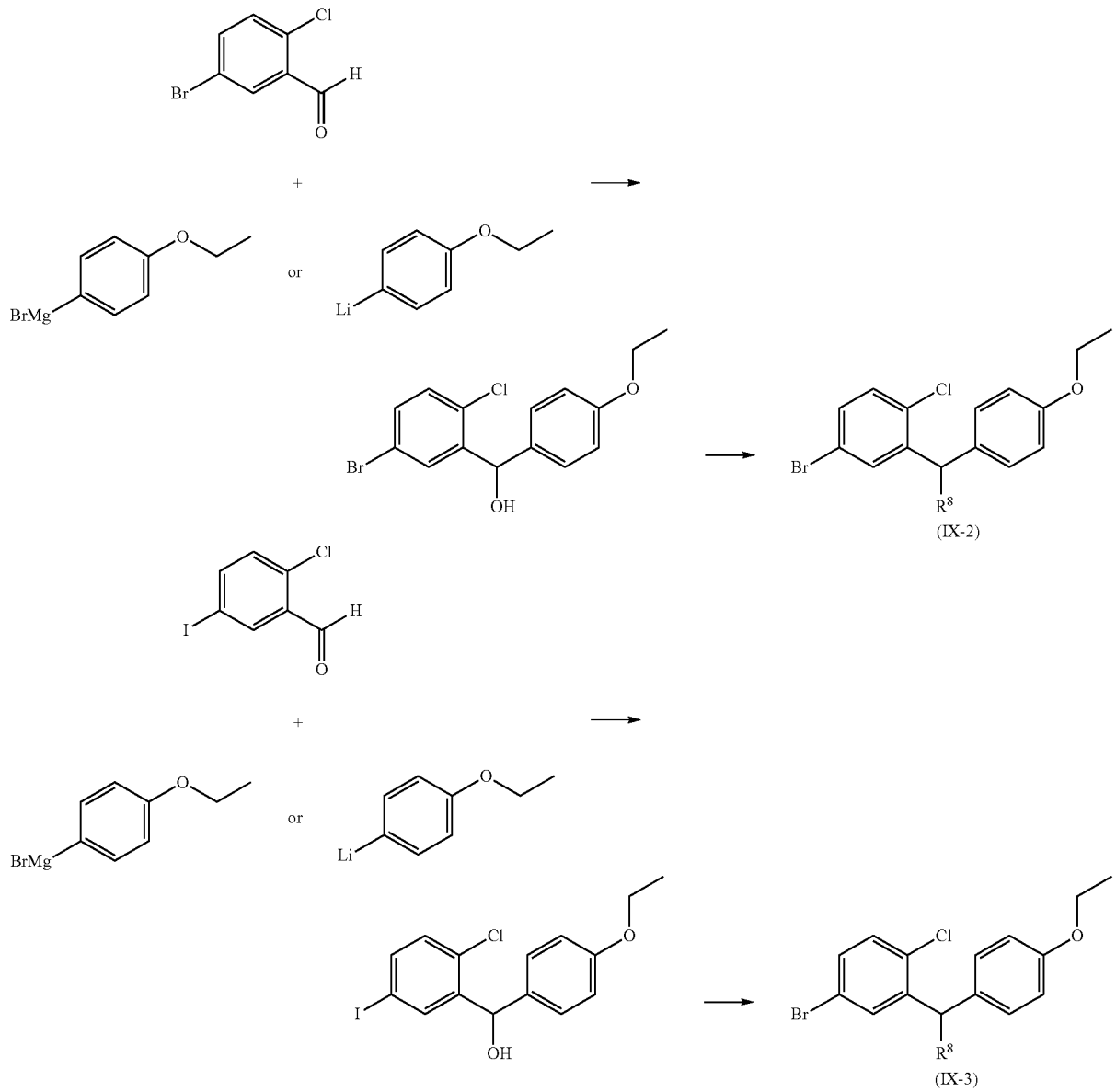

Alternatively, Example 9 could be synthesized via (IX-1a) using the procedure reported by Mascitti, V. et al., *Organic Letters* 12, 2940, (2010) using the corresponding 1,3-dithiane intermediate (IX-4) (where $R^8$ is OPMB, OBn, OTBS, OTMS, OTES, OTIPS, OAllyl, OBOM, OPMBM, ODMBM, OMOM, OMEM, OMTM, OSEM, OH or any suitably protected precursor to the claimed example 9):

(IX-4)

As depicted in Scheme 8, intermediate (IX-4) could be accessed from compounds (IX-2) or (IX-3) by halogen-metal exchange followed by trapping with N,N-dimethylformamide or N-formylmorpholine under classical conditions (see for instance the procedure for the synthesis of 3-(tert-Butyl-dimethyl-silanyloxymethyl)-4-chloro-benzaldehyde in PCT Publication No. WO 06/129237) to produce the corresponding aldehyde (IX-5). Aldehyde (IX-5) could then be converted to the corresponding 1,3-dithiane derivative (IX-4) under conditions known by those skilled in the art (see for instance the formation of compound 1 in Samas, B. et al. *Acta Crystallograohica* E66, o1386, (2010) and the general procedure in Ouyang, Y. et al. *Synthesis,* 3801 (2006)).

Scheme 8

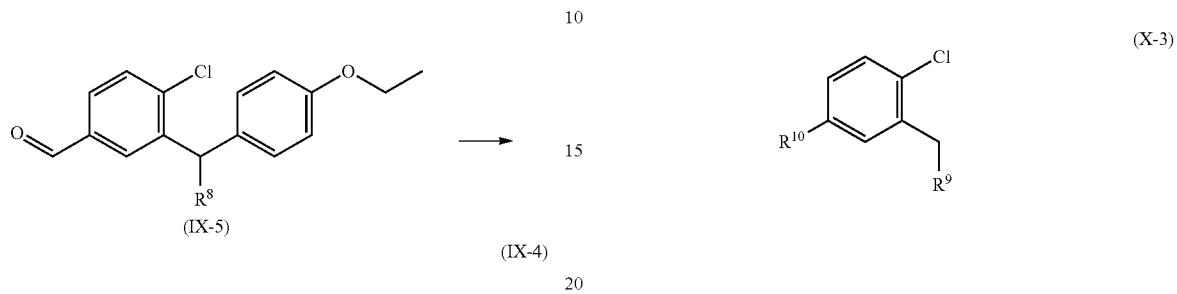

Compounds of general structure (S1-A) in Scheme 1 could also be prepared using the procedure reported by Mascitti, V. et al., Organic Letters 12, 2940, (2010). The desired 1,3-dithiane starting material can be accessed in a similar fashion to (IX-4) starting from the corresponding aryl halide (if $R^5$ is OTBS, see US2007/0054867 for the preparation of {4-[(5-bromo-2-chloro-phenyl)-methyl]-phenoxy}-tert-butyl-dimethyl-silane). Depending on $R^5$, the compounds thus obtained could then be easily functionalized to other compounds of structure (A) from the present invention using well known protective and functional groups manipulation sequences known by those skilled in the art. See examples section for further details.

When using the appropriate organometallic reagent (X-1) wherein M is Li or Mg, X' is Cl, Br or I and p is 0-2 ($R^9$ is H, OPMB, OTBS, OTES, OTIPS, OAllyl, OPh, OBOM, OPMBM, ODMBM, OMOM, OMEM, OMTM, OSEM), the procedures described in steps 1 to 6 of Scheme 2 allow access to intermediates of general structure (X-2) (Scheme 9).

Scheme 9

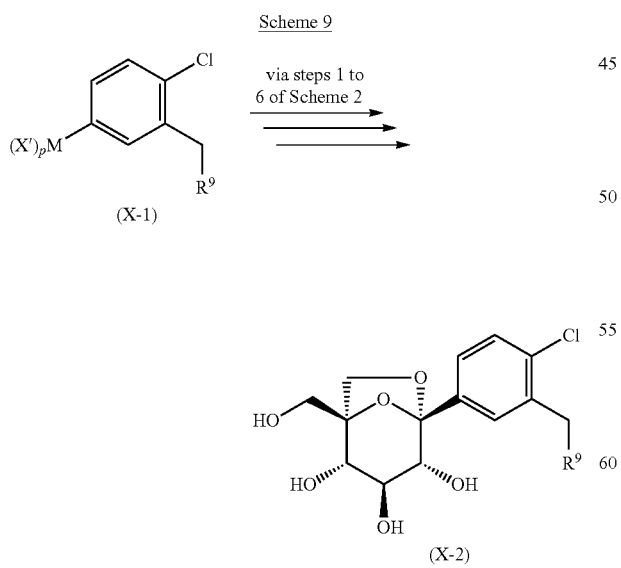

The organometallic reagents (X-1) are accessible from the corresponding aryl halide (X-3), where $R^{10}$ is Cl, Br or I, using general protocols of halogen-metal exchange known by those skilled in the art (see for instance example XII in PCT Publication No. WO 07/031548).

Generally, aryl halides (X-3) where $R^{10}$ is Br or I, are either commercially available (4-bromo-1-chloro-2-methylbenzene is available from TCI America and 1-chloro-4-iodo-2-methylbenzene is available from Best Pharma Tech Inc.) or can be prepared from readily available starting materials (such as (5-bromo-2-chlorophenyl)methanol available from Sigma-Aldrich or (2-chloro-5-iodophenyl)methanol which can be prepared according to example 27 of PCT Publication No. WO 08/077009) by adequate protection of the hydroxyl group following experimental protocols known by those skilled in the art. For a general description of protecting groups and their use, see T. W. Greene, *Protective Groups in Organic Synthesis*, John Wiley & Sons, New York, 1991. More specifically, the following starting materials can be prepared using the procedures described in the corresponding references:

4-bromo-1-chloro-2-((methoxymethoxy)methyl)benzene can be prepared by a procedure described in PCT Publication No. WO 04/093544.

4-bromo-1-chloro-2-(((2-methoxyethoxy)methoxy)methyl) benzene can be prepared by a procedure described in example 12 of U.S. Pat. No. 5,043,142.

(5-bromo-2-chlorobenzyloxy)(tert-butyl)dimethylsilane can be prepared by a procedure described in example 14 of PCT Publication No. WO 06/005914.

(5-bromo-2-chlorobenzyloxy)triisopropylsilane can be prepared by a procedure described to produce compound 17 of the following reference: Lee, J et al. *Bioorganic and Medicinal Chemistry* 18, 2178 (2010).

4-bromo-1-chloro-2-(phenoxymethyl)benzene can be prepared by a procedure described in example VII of PCT Publication No. WO 07/031548.

Following the synthetic routes in Scheme 10, compounds of general structure (X-2) can be converted to intermediates that allow access to compounds claimed in the present invention.

Scheme 10

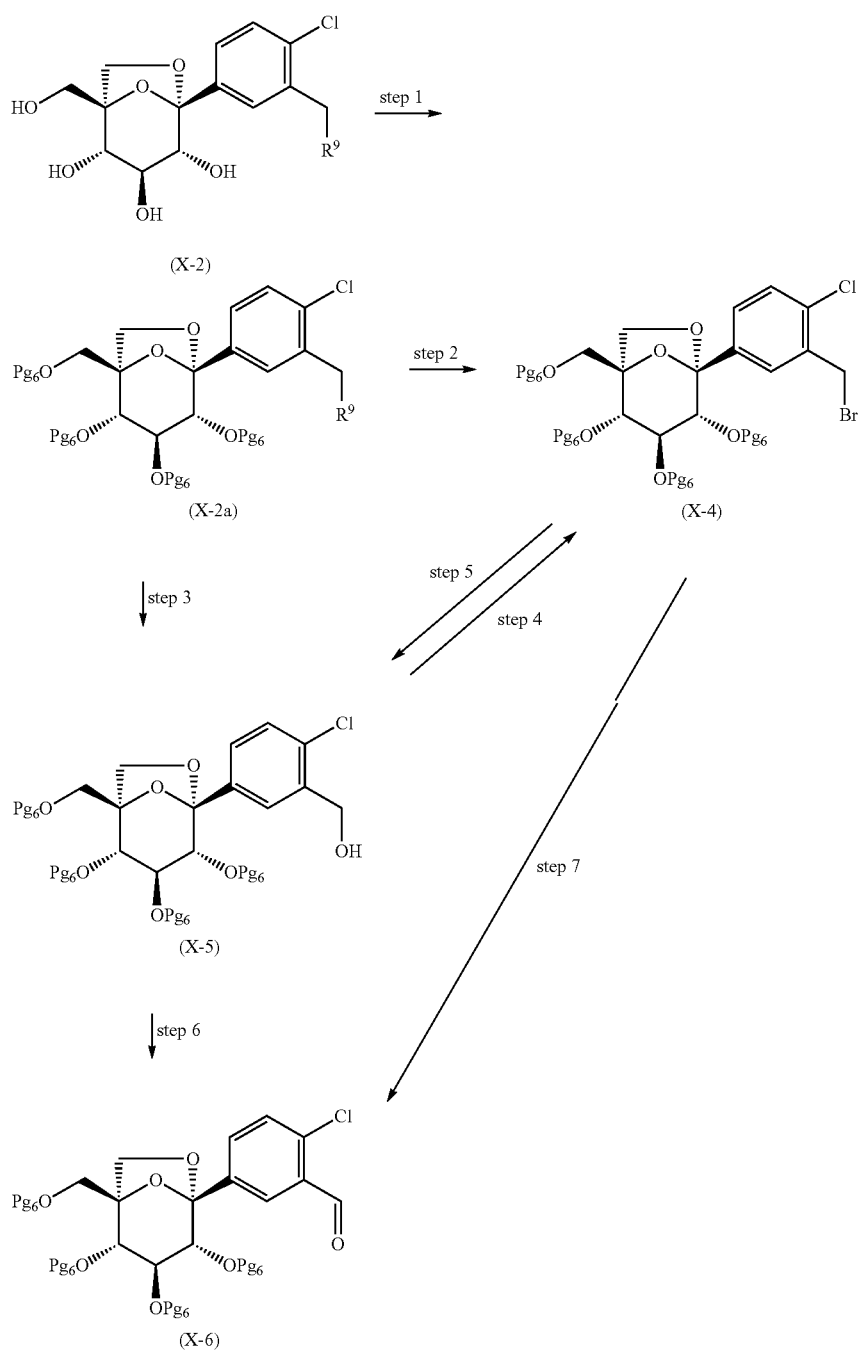

In step 1 of Scheme 10, the hydroxyl groups of (X-2) could be protected by the appropriate protecting groups (Pg$_6$). For example, benzyl groups (Pg$_6$ is Bn) could be introduced by treatment of intermediate (X-2) with benzyl bromide or benzyl chloride in the presence of sodium hydride, potassium hydride, potassium tert-butoxide in a solvent such as tetrahydrofuran, 1,2-dimethoxyethane or N,N-dimethylformamide at a temperature ranging from about 0 degrees Celsius to about 80 degrees Celsius. Conditions involving benzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes could also be used. Acetyl or benzoyl groups (Pg$_6$=Ac or Bz) may be introduced by treatment of intermediate (X-2) with acetyl chloride, acetyl bromide or acetic anhydride or benzoyl chloride or benzoic anhydride in the presence of a base such as triethylamine, N,N-diisopropylethylamine or 4-(dimethylamino)pyridine in a solvent such as tetrahydrofuran, 1,2-dimethoxyethane or dichloromethane at a temperature ranging from about 0 degrees Celsius to about 80 degrees Celsius.

In step 2 of Scheme 10, when R$^9$ is H, bromination of compound (X-2a) with N-bromosuccinimide and dibenzoylperoxide in CCl$_4$ at reflux (see example 2 of EP0151529 for a representative experimental procedure) could be used to obtain (X-4). If R$^9$ is OPh, treatment of a solution of (X-2a) in acetic acid in the presence of HBr at a temperature ranging from about 0 degrees to about 80 degrees Celsius (preferentially about room temperature) could lead to (X-4) (for a representative experimental procedure see example XIV of PCT Publication No. WO 07/031548).

In step 3 of Scheme 10, when R$^9$ is OPMB, OTBS, OTES, OTIPS, OAllyl, OBOM, OPMBM, ODMBM, OMOM, OMEM, OMTM, or OSEM, the protecting group masking the benzyl alcohol functionality in compound (X-2a) may be removed using the appropriate chemistry for the particular protecting group, following procedures known by those skilled in the art, to produce intermediate (X-5). For a general description of protecting groups and their use, see T. W. Greene, *Protective Groups in Organic Synthesis*, John Wiley & Sons, New York, 1991.

In step 4 of Scheme 10, intermediate (X-4) could be produced by treatment of a solution of intermediate (X-5) in a solvent such as tetrahydrofuran or 2-methyltetrahydrofuran in the presence of triphenylphosphine and N-bromosuccinimide (or carbon tetrabromide) at a temperature ranging from about 0 degrees Celsius to about 40 degrees Celsius (for a representative experimental procedure see example II of PCT Publication No. WO 07/031548).

When Pg$_6$ is not Ac or Bz, in step 5 of Scheme 10, intermediate (X-4) could be converted to intermediate (X-5) by (1) conversion of (X-4) to the corresponding benzylic acetate under conditions known by those skilled in the art followed by (2) hydrolysis of the acetate protective group under conditions known by those skilled in the art. For a representative procedure see the protocol for the formation of compound 5 from 4 in Samas, B. et al. *Acta Crystallographica* E66, o1386, (2010).

In step 6 of Scheme 10, intermediate (X-6) could be produced by benzylic oxidation of intermediate (X-5). The Swern oxidation described by Kanji Omura and Daniel Swern in *Tetrahedron*, 34, 1651 (1978) or the Parikh-Doering oxidation described in Parikh, J. et al. *Journal of the American Chemical Society* 89, 5505 (1967) could be used. Modifications of this process known to those skilled in the art may also be used. For example, other oxidants, such as stabilized 2-iodoxybenzoic acid described by Ozanne, A. et al. in *Organic Letters*, 5, 2903 (2003) or the like may also be used. Intermediate (X-6) could also be accessed via a Kornblum oxidation (step 7 of Scheme 10) of intermediate (X-4) (Kornblum, N., et al., *Journal of The American Chemical Society*, 81, 4113 (1959); for a representative procedure see also the formation of compound 6 in Samas, B. et al. *Acta Crystallograohica* E66, o1386, (2010); for a procedure using N-methylmorpholine-N-oxide as a reagent see example VII of PCT Publication No. WO 08/034859). Compound (X-6) could be accessed from (X-5) following procedures similar to those previously described for steps 1 and 2 of Scheme 4.

In step 1 of Scheme 11, activation or functionalization of bromobenzylic derivatives of general structure (X-4) could lead to intermediate (X-7).

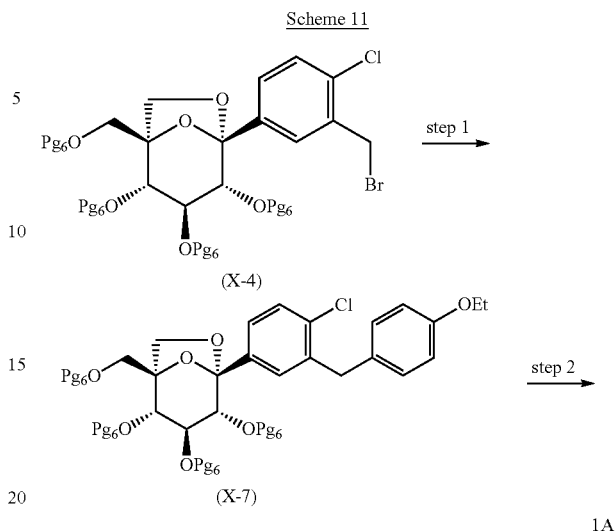

Various methods known by those skilled in the art for the formation of diarylmethane motifs starting from bromobenzyl derivatives could be used (see, Liégault, B. et al. *Chemical Society Reviews* 37, 290, (2008)).

In step 1 of Scheme 11, a Suzuki-type coupling between compound (X-4) and 4-ethoxyphenylboronic acid (available from Matrix Scientific or Frontier Scientific Inc.) under conditions known by those skilled in the art (for classical protocols of Suzuki couplings see for instance example XV of PCT Publication No. WO 07/031548; Nobre, S. M. et al. *Tetrahedron Letters* 45, 8225 (2004); Bandgar, B. P. et al. *Tetrahedron Letters* 45, 6959 (2004); and Table 1 and reference cited in Liégault, B. et al. *Chemical Society Reviews* 37, 290, (2008)) could produce compound (X-7). Potassium (4-ethoxyphenyl)trifluoroborate (available from Combi-Blocks) could also be used in the Suzuki-type coupling with (X-4); for a general procedure for the Suzuki-Miyaura cross-coupling using potassium aryltrifluoroborates, see Molander, G. A. et al. in *Journal of Organic Chemistry* 71, 9198 (2006) and reference cited herein. Additional protocols for Suzuki couplings could also be used (see for instance Srimani, D. et al. *Tetrahedron Letters* 49, 6304, (2008); Fairlamb, I. J. S. et al. *Synthesis* 508 (2009); table 1 entry 7 in Singh, R. et al. *Organic Letters* 7, 1829, (2005). A 4-ethoxyphenylboronic ester derivative such as 2-(4-ethoxyphenyl)-4,4,5,5-tetramethyl-1,3,2-dioxaborolane (see PCT Publication No. WO 06/108695) may also be used as a reagent in the Suzuki couplings mentioned above.

In step 1 of Scheme 11, a Stille-type coupling between (X-4) and tributyl(4-ethoxyphenyl)stannane (for the synthesis and characterization of this reagent see, Wardell, J. L. et al. *Journal of Organometallic Chemistry* 78, 395 (1974)) following protocols known by those skilled in the art could be used to produce (X-7). For representative examples of Stille coupling protocols see, table 2 entry 6 in Crawforth C. M. et al. in *Tetrahedron* 61, 9736 (2005), and Kuribayashi, T. et al. in *Synlett* 737 (1999).

Alternatively, when Pg$_6$ is not Ac or Bz, in step 1 of Scheme 11, a Kumada-type coupling between (X-4) and 4-ethoxyphenylmagnesium bromide (Rieke Metals, Inc) may be used to produce (X-7) following procedures for Kumada-type couplings known by those skilled in the art (see for example footnote 14 in Lopez-Perez, A. et al. *Organic Letters* 11, 5514 (2009)).

Alternatively, when Pg$_6$ is not Ac or Bz, in step 1 of Scheme 11, 1-ethoxy-4-iodobenzene (TCI America) may be treated at low temperature (between about −78 and about 0 degrees Celsius) with a solution of isopropylmagnesium chloride in a solvent such as tetrahydrofuran or the like followed by the addition of CuCN*2LiCl in tetrahydrofuran or the like at the same temperature. The reactive species thus formed may then be reacted with a tetrahydrofuran solution of (X-4) at a temperature ranging from about −20 to about 23 degrees Celsius to produce after work-up compound (X-7) (see procedure described in example X of PCT Publication No. WO 06/089872). Alternatively, in step 1 of Scheme 11, a Negishi-type coupling between (X-4) and bromo(4-ethoxyphenyl)-zinc, iodo(4-ethoxyphenyl)-zinc or chloro(4-ethoxyphenyl)-zinc (prepared from the corresponding aryl halide following protocols known by those skilled in the art) could produce (X-7) following protocols for the Negishi-type coupling known by those skilled in the art (see entry 4 table 1 and typical cross-coupling procedure in de Lang, R-J. et al. in *Tetrahedron* 54, 2953 (1998)).

Alternatively, in step 1 of Scheme 11, the reaction of the indium organometallic reagent tris(4-ethoxyphenyl)indium (prepared from the corresponding Grignard reagent or organolithium reagent) could be reacted with (X-4) to produce (X-7) following the general procedure described (table 4 entry 1) in Perez, I. et al. *Journal of The American Chemical Society* 123, 4155 (2001).

In step 1 of Scheme 11, (X-4) could be converted to the corresponding benzylzinc reagent (following various protocols known by those skilled in the art such as that found in, but not limited to, Utas, J. E. et al. *Synlett* 1965 (2006); Knochel, P. et al. *Organic Letters* 10, 1107 (2008)) and reacted with 1-ethoxy-4-iodobenzene (TCI America) or 1-bromo-4-ethoxybenzene (TCI America) to produce (X-7). For general protocols see, Negishi, E. et al. *Journal of Organic Chemistry* 42, 1821 (1977); Utas, J. E. et al. *Synlett* 1965 (2006); table 2 entry 3 in Stefko, M. et al. *European Journal of Organic Chemistry* 1689 (2008); table 1 entry 3 in Knochel, P. et al. *Organic Letters* 10, 1107 (2008); formation of compound 16 step 2 in Sato, M. et al. *Journal of Medicinal Chemistry* 52, 4869 (2009); table 2 entry 7 and 8 in Knochel, P. et al. *Journal of Organic Chemistry* 73, 7380 (2008).

In step 2 of Scheme 11, the remaining protecting groups (Pg$_6$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce compound 1A which can then be easily functionalized to other compounds of structure (A) from the present invention using well known protective and functional group manipulation sequences known by those skilled in the art. See the examples section for further details. Other conditions known for the removal of benzyl protecting groups may also be used. If Pg$_6$ is Ac or Bz, then acetate and benzoate protecting groups may be removed by treatment of a solution of (X-7) in an alcoholic solvent such as methanol (a co-solvent such as tetrahydrofuran may also be added) in the presence of sodium methoxide at a temperature ranging from about 0 to about 70 degrees Celsius to produce compound 1A. Other conditions known for the removal of acetates and benzoate protecting groups may also be used.

An alternative synthesis of compound (X-7) is presented in Scheme 12. In step 1 of Scheme 12, compound (X-5) may be converted to the corresponding benzylic acetate, benzylic carbonate or benzylic phosphate and subsequently reacted with 4-ethoxyphenylboronic acid (available from Matrix Scientific or Frontier Scientific Inc) following general protocols known by those skilled in the art and respectively reported in Kuwano, R. et al. *Chemical Communications* 5899 (2005), Kuwano, R. et al. *Organic Letters* 7, 945 (2005), McLaughlin, M. *Organic Letters* 7, 4875 (2005). Compound (X-7) thus obtained could then be easily converted to compound 1A following step 2 of Scheme 11.

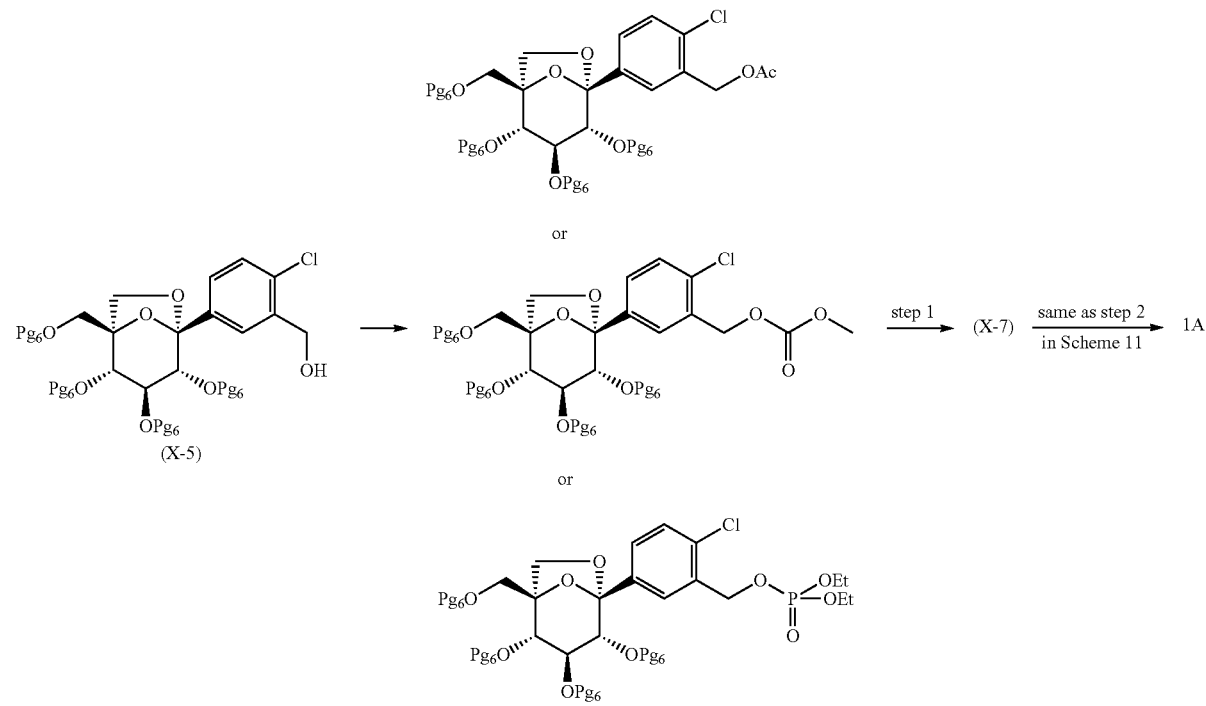

Scheme 12

As described in Scheme 13, compound (X-6) could also be used to access to Example 9 or compound of structure 1A.

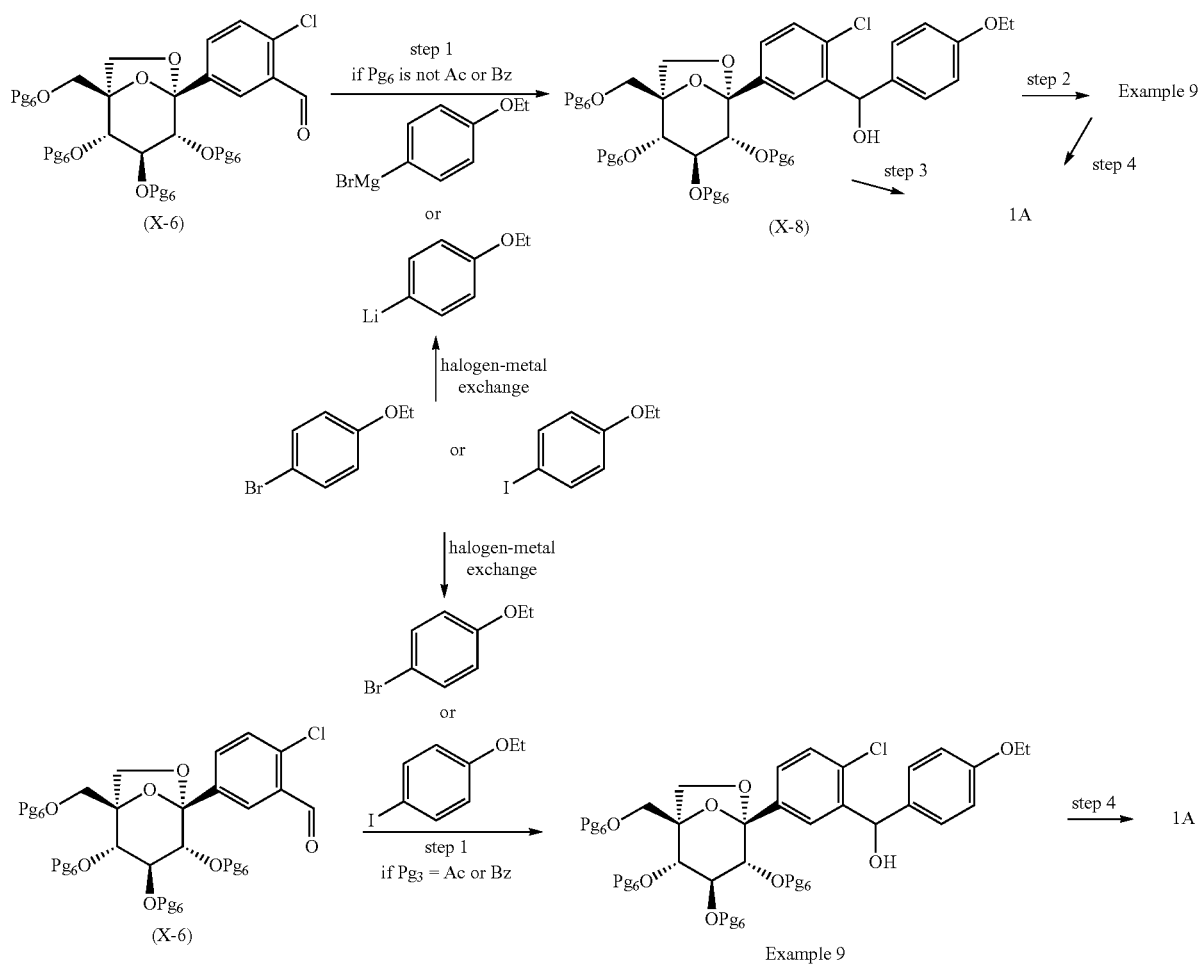

Scheme 13

In step 1 of Scheme 13, compound (X-6) may be treated with an organometallic reagent such as 4-ethoxyphenylmagnesium bromide or 4-ethoxyphenyllithium to produce (X-8) (following protocols known by those skilled in the art for the nucleophilic addition of a Grignard or organolithium reagent to a benzaldehyde derivative; see formation of (IX-2) and (IX-3) or the procedure described in example VI of PCT Publication No. WO 06/089872). In the particular case where $Pg_6$ is Ac or Bz, an excess of the organometallic reagent (4-ethoxyphenylmagnesium bromide or 4-ethoxyphenyllithium) has to be used (see the procedure described for the organometallic addition step of example 1 of PCT Publication No. WO 08/034859) to produce Example 9 after aqueous work-up for such organometallic nucleophilic addition reactions and treatment of the resulting crude mixture with a solution of sodium methoxide (or aqueous solution of potassium or sodium hydroxide) in an alcoholic solvent such as methanol (in the presence of an optional co-solvent such as tetrahydrofuran) at a temperature ranging from about 0 to about 60 degrees Celsius to remove the remaining Ac or Bz protecting groups.

In step 2 of Scheme 13, Example 9 may be produced by removal of the remaining protecting groups ($Pg_6$) using the appropriate chemistry for the particular protecting groups using protocols known by those skilled in the art. For a general description of protecting groups and their use, see T. W. Greene, *Protective Groups in Organic Synthesis*, John Wiley & Sons, New York, 1991.

In the event that hydrogenolysis conditions are used (for example if $Pg_6$ is Bn; such conditions could be but are not limited to: Pd black in presence of formic acid in an alcoholic solvent such as ethanol with the optional presence of a co-solvent such as tetrahydrofuran at a temperature ranging from about 0 to about 50 degrees Celsius; alternative conditions involve the use of Pd—C or Pd(OH)$_2$ as catalysts under a hydrogen gas atmosphere in an alcoholic solvent such as ethanol with the optional presence of a co-solvent such as tetrahydrofuran at a temperature ranging from about 0 to about 50 degrees Celsius and with the optional presence of an acid like acetic acid, trifluoroacetic acid, hydrochloric acid or formic acid) then compound 1A may be obtained instead of Example 9 (step 3 of Scheme 13). The compound 1A thus obtained could be converted to Example 9 via Example 2 following the procedures described in the experimental section. In a similar manner, in step 4 of Scheme 13, treatment of Example 9 under hydrogenolysis conditions (for instance, but not limited to, the conditions described above) could provide compound 1A. Alternatively, in step 4 of Scheme 13, compound 1A may be obtained by treatment of a solution of Example 9 in a solvent such as dichloromethane with a silicon hydride derivative such as triethylsilane in the presence of an acid such as trifluoroacetic acid, formic acid or boron trifluoride diethyletherate at a temperature ranging from about −30 degrees to about 23 degrees Celsius (for a general protocol, see the procedure described in example VII of PCT Publication No. WO 06/089872).

Alternatively, in step 3 of Scheme 13, compound 1A may be accessed from intermediate (X-8) by (1) treatment under hydrogenolysis conditions (for instance, but not limited to, the conditions described above) or treatment with a silicon hydride derivative under acidic conditions (for instance, but not limited to, the conditions described above) and (2) removal of the remaining protecting groups (Pg$_6$) using the appropriate chemistry for the particular protecting groups.

Starting from (X-2), it may also be advantageous to selectively protect the hydroxyl groups on the dioxa-bicyclo [3.2.1]octane motif (Scheme 14). Someone skilled in the art would recognize that compound (X-2b) could be accessed from (X-2) by selective protection of the primary hydroxyl group with a suitable protecting group (Pg$_3$) followed by protection of the remaining secondary hydroxyl groups with suitable protecting groups (Pg$_4$) following similar procedures, for the particular protecting groups chosen, described in steps 1 and 2 of Scheme 3. In a similar way described for (X-2a), compound (X-2b) could lead to intermediates (X-4a), (X-5a), and (X-6a) (Scheme 14). In turn, (X-4a), (X-5a), and (X-6a) could be converted to Example 9 and/or 1A following the protocols described in Schemes 11, 12 and 13 by replacing the deprotection step of protecting group (Pg$_6$) by the removal of the remaining protecting groups (Pg$_3$) and (Pg$_4$) using the appropriate chemistry for the particular protecting groups.

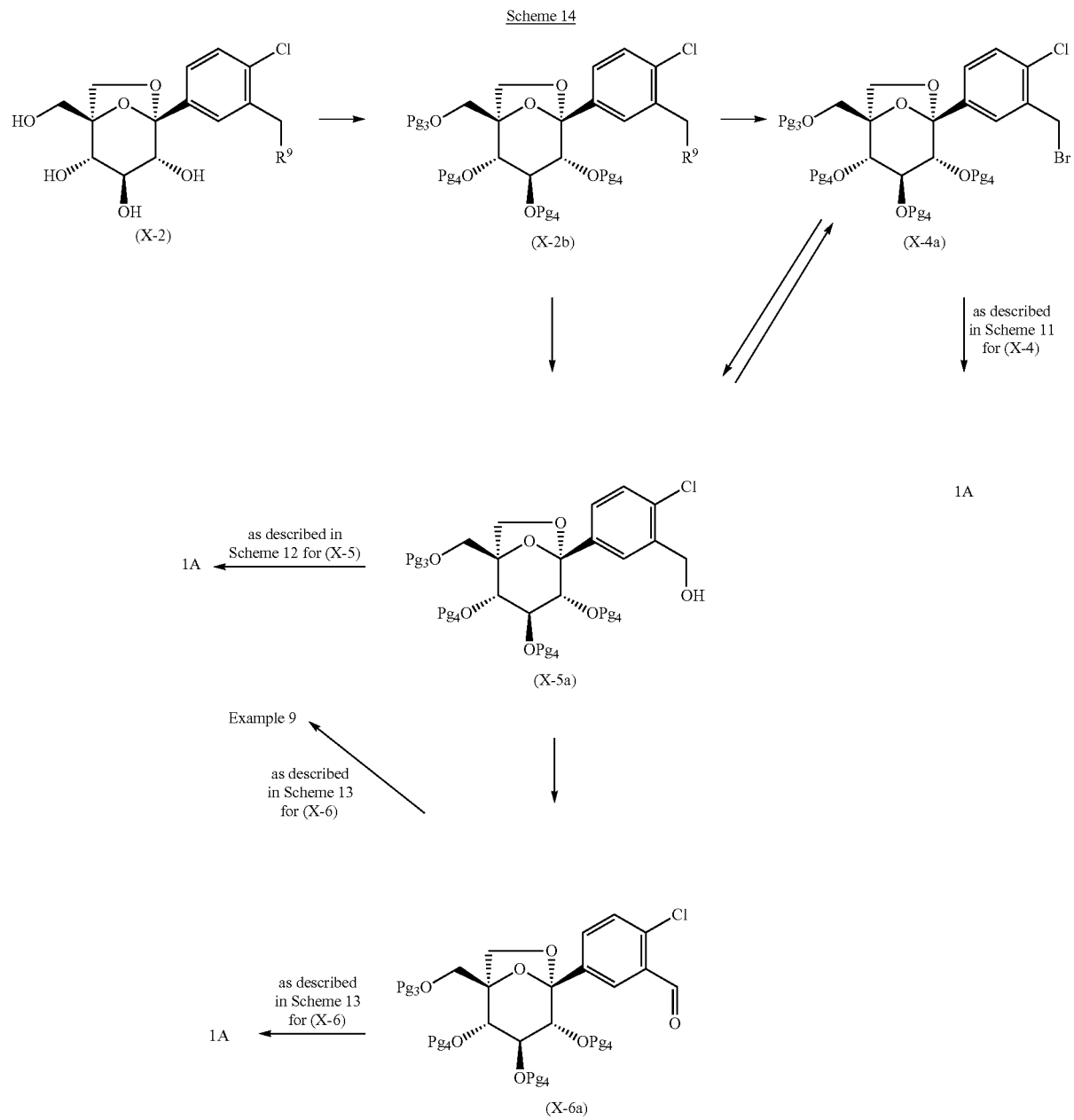

Scheme 14

Example 10

(1S,2S,3S,4R,5S)-5-[4-Chloro-3-(4-ethoxy-benzyl)-phenyl]-1-chloromethyl-6,8-dioxa-bicyclo[3.2.1]octane-2,3,4-triol

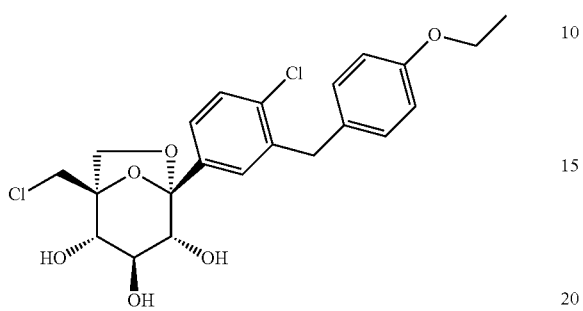

To a solution of {(1S,2S,3S,4R,5S)-2,3,4-tris-benzyloxy-5-[4-chloro-3-(4-ethoxy-benzyl)-phenyl]-6,8-dioxa-bicyclo[3.2.1]oct-1-yl}-methanol (200 mg, 0.28 mmol) in dichloromethane (3 mL) at 0 degrees Celsius was added diethylaminosulfur trifluoride (40 microL, 0.30 mmol) and the resulting mixture was slowly warmed to room temperature and stirred at this temperature for 16 hours. The mixture was diluted with dichloromethane and washed with a saturated solution of aqueous sodium bicarbonate, and brine, dried over sodium sulfate, filtered and concentrated in vacuo. The residue was purified by flash chromatography over silica gel using a 12 g redisep silica cartridge (eluting with a gradient of 0 to 20% ethyl acetate in heptane) to afford a mixture of (1S,2S,3S,4R,5S)-2,3,4-tris-benzyloxy-5-[4-chloro-3-(4-ethoxy-benzyl)-phenyl]-1-fluoromethyl-6,8-dioxa-bicyclo[3.2.1]octane and (1S,2S,3S,4R,5S)-2,3,4-tris-benzyloxy-5-[4-chloro-3-(4-ethoxy-benzyl)-phenyl]-1-chloromethyl-6,8-dioxa-bicyclo[3.2.1]octane as a colorless oil (50 mg). (MS) 725 (M+H$^+$, positive mode).

To a suspension of a mixture of (1S,2S,3S,4R,5S)-2,3,4-tris-benzyloxy-5-[4-chloro-3-(4-ethoxy-benzyl)-phenyl]-1-fluoromethyl-6,8-dioxa-bicyclo[3.2.1]octane and (1S,2S,3S,4R,5S)-2,3,4-tris-benzyloxy-5-[4-chloro-3-(4-ethoxy-benzyl)-phenyl]-1-chloromethyl-6,8-dioxa-bicyclo[3.2.1]octane (50 mg, 0.07 mmol) and palladium black (50 mg, 0.38 mmol, Aldrich® high surface area) in ethanol (0.5 mL) and tetrahydrofuran (0.1 mL) was added formic acid (0.10 mL, 2.80 mmol) and the resulting mixture was stirred at room temperature for 1.5 hours. Ethyl acetate was added and the mixture was filtered through a short pad of Celite® and concentrated in vacuo. The crude material was purified by flash chromatography over silica gel using a 4 g redisep silica cartridge (eluting with a gradient of 50 to 100% ethyl acetate in heptane) to afford the title compound as a solid (8.6 mg; ~80% pure, contaminated with some Example 8).

(LCMS) 455.2 (M+H$^+$: positive mode). $^1$H NMR (400 MHz, METHANOL-d$_4$) delta ppm 7.40 (t, J=1.17 Hz, 1 H), 7.34 (s, 1 H), 7.34 (s, 1 H), 7.05-7.09 (m, 2 H), 6.76-6.80 (m, 2 H), 4.18 (d, J=7.61 Hz, 1 H), 4.01 (s, 2 H), 3.97 (q, J=7.03 Hz, 2 H), 3.90 (d, J=12.30 Hz, 1 H), 3.83 (dd, J=8.20, 1.56 Hz, 1 H), 3.72 (d, J=12.30 Hz, 1 H), 3.60-3.65 (m, 2 H), 3.50-3.54 (m, 1 H), 1.33 (t, J=7.03 Hz, 3 H).

Example 11

(1S,2S,3S,4R,5S)-5-{4-Chloro-3-[(R)-(4-ethoxy-phenyl)-hydroxy-methyl]-phenyl}-1-hydroxymethyl-6,8-dioxa-bicyclo[3.2.1]octane-2,3,4-triol (9A-1) and (1S,2S,3S,4R,5S)-5-{4-Chloro-3-[(S)-(4-ethoxy-phenyl)-hydroxy-methyl]-phenyl}-1-hydroxymethyl-6,8-dioxa-bicyclo[3.2.1]octane-2,3,4-triol (9A-2)

9A-1

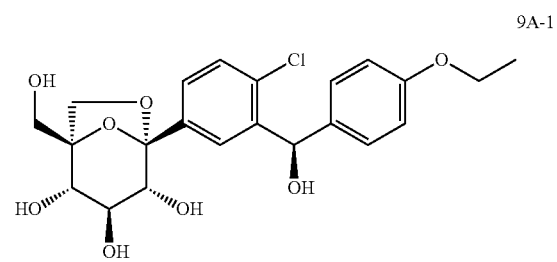

9A-2

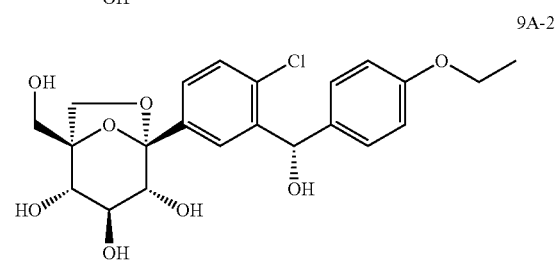

To a solution of acetic acid (1R,2S,3S,4R,5S)-3,4-diacetoxy-1-acetoxymethyl-5-[4-chloro-3-(4-ethoxy-benzyl)-phenyl]-6,8-dioxa-bicyclo[3.2.1]oct-2-yl ester (Example 2; 344 mg, 0.569 mmol) in carbon tetrachloride (8 mL) was added N-bromosuccinimide (159 mg, 0.893 mmol) followed by the addition of 2,2'-azobisisobutyronitrile (AIBN, 8 mg, 0.05 mmol) and the reaction mixture was heated at reflux under nitrogen. After 16 hours, the reaction mixture was cooled to room temperature, water (50 mL) and dichloromethane (25 mL) were added and the resulting mixture was stirred for 24 hours at room temperature. The layers were separated and the aqueous layer was extracted two additional times with dichloromethane (25 mL). The combined organic layers were washed with brine (20 mL), dried over magnesium sulfate, filtered through a pad of celite, and concentrated under reduced pressure. The crude material was chromatographed with the Biotage SP4 automated chromatography unit (SNAP 25 g silica gel column) eluting with a gradient of 0-80% ethyl acetate in heptane to produce 316 mg (89% yield) of acetic acid (1R,2S,3S,4R,5S)-3,4-diacetoxy-1-acetoxymethyl-5-{4-chloro-3-[(4-ethoxy-phenyl)-hydroxy-methyl]-phenyl}6,8-dioxa-bicyclo[3.2.1]oct-2-yl ester as a mixture of diastereoisomers at the bis-benzylic position.

To a solution of acetic acid (1R,2S,3S,4R,5S)-3,4-diacetoxy-1-acetoxymethyl-5-{4-chloro-3-[(4-ethoxy-phenyl)-hydroxy-methyl]-phenyl}6,8-dioxa-bicyclo[3.2.1]oct-2-yl ester (400 mg, 0.644 mmol) in dichloromethane (10 mL) at 0 degrees Celsius was added Dess-Martin periodinane reagent (609 mg, 1.0 mmol) and the reaction mixture was allowed to stir at this temperature for 1.5 hours. The reaction mixture was then diluted with dichloromethane (20 mL) followed by the addition of a saturated aqueous solution of sodium bicarbonate (20 mL) and a saturated aqueous solution of sodium thiosulfate (20 mL). The mixture was allowed to stir vigorously for 30 minutes before separating the layers. The aqueous layer was washed with dichloromethane (2×20 mL) and the combined organic layers were dried over magnesium sulfate, filtered and concentrated under reduced pressure. The crude material was chromatographed using the Biotage SP4 automated chromatography unit (SNAP 25 g silica gel column) and eluting with a gradient of 0-80% ethyl acetate in heptane to produce 178 mg (44.7% yield) of acetic acid (1R,2S,3S,4R,5S)-3,4-diacetoxy-1-acetoxymethyl-5-[4-chloro-3-(4-ethoxy-benzoyl)-phenyl]-6,8-dioxa-bicyclo[3.2.1]oct-2-yl ester and 145 mg of a 4/1 mixture of acetic acid (1R,2S,3S,4R,5S)-3,4-diacetoxy-1-acetoxymethyl-5-[4-chloro-3-(4-ethoxy-benzoyl)-phenyl]-6,8-dioxa-bicyclo[3.2.1]oct-2-yl ester/ acetic acid (1R,2S,3S,4R,5S)-3,4-diacetoxy-1-acetoxymethyl-5-{4-chloro-3-[(4-ethoxy-phenyl)-hydroxy-methyl]-phenyl}6,8-dioxa-bicyclo[3.2.1]oct-2-yl ester. Data for acetic acid (1R,2S,3S,4R,5S)-3,4-diacetoxy-1-acetoxymethyl-5-[4-chloro-3-(4-ethoxy-benzoyl)-phenyl]-6,8-dioxa-bicyclo[3.2.1]oct-2-yl ester: MS (LCMS) 619 (M+H$^+$; positive mode) $^1$H NMR (400 MHz, METHANOL-d$_4$) delta ppm 1.40 (t, J=7.0 Hz, 3 H), 1.81 (s, 3 H), 1.94 (s, 3 H), 2.01 (s, 3 H), 2.03 (s, 3 H), 3.78 (d, J=8.2 Hz, 1 H), 4.01 (d, J=12.7 Hz, 1 H), 4.12 (q, J=6.9 Hz, 2 H), 4.43 (d, J=8.4 Hz, 1 H), 4.59 (d, J=12.9 Hz, 1 H), 5.25 (d, J=8.0 Hz, 1 H), 5.38 (t, J=8.0 Hz, 1 H), 5.44 (d, J=8.2 Hz, 1 H), 6.98 (d, J=8.8 Hz, 2 H), 7.44 (d, J=2.0 Hz, 1 H), 7.52 (d, J=8.4 Hz, 1 H), 7.62 (dd, J=8.4, 2.0 Hz, 1 H), 7.68 (d, J=8.8 Hz, 2 H).

To a solution of the above 4/1 mixture of acetic acid (1R,2S,3S,4R,5S)-3,4-diacetoxy-1-acetoxymethyl-5-[4-chloro-3-(4-ethoxy-benzoyl)-phenyl]-6,8-dioxa-bicyclo[3.2.1]oct-2-yl ester/acetic acid (1R,2S,3S,4R,5S)-3,4-diacetoxy-1-acetoxymethyl-5-{4-chloro-3-[(4-ethoxy-phenyl)-hydroxy-methyl]-phenyl}6,8-dioxa-bicyclo[3.2.1]oct-2-yl ester (145 mg) in methanol (2.5 mL) was added sodium borohydride (35 mg, 0.92 mmol) at room temperature. After one hour, the reaction mixture was quenched by the addition of water (20 mL) and the resulting mixture was concentrated under reduced pressure. The resulting aqueous layer was extracted three times with ethyl acetate (15 mL). The combined organic layers were washed with brine (20 mL), dried over sodium sulfate, filtered and concentrated under reduced pressure.

To a solution of the crude material in methanol (5 mL) was added sodium methoxide in methanol (25% wt) until pH 12 was obtained and the resulting mixture was stirred at room temperature. After 16 hours, the reaction mixture was neutralized by the addition of Dowex Monosphere 650C (H) cation exchange resin until the pH of the solution was <7. The reaction mixture was filtered and concentrated under reduced pressure yielding 100 mg of the desired product as a mixture of diastereoisomers (see Example 9). The resulting mixture was separated by chiral HPLC. Purification method: Column: Chiralpak AD-H (10×250), Flow rate: 10.0 mL/minute, back pressure: 120 Bar, mobile phase: 65/35 CO$_2$/propanol; UV detection: 210 nm.

The configuration of the carbon at the bis-benzylic position in compounds 9A-1 and 9A-2 was arbitrarily assigned to R and S respectively.

(9A-1): (17.5 mg, 16.5% yield); R$_t$=4.68 minutes; the fractions containing the product were concentrated under reduced pressure. The resulting material was precipitated from ethyl acetate and heptane. The resulting white solid was washed with heptane 2 times and dried under reduced pressure.

MS (LCMS) 451.2 (M–H$^+$, negative mode)$^1$H NMR (400 MHz, METHANOL-d4) delta ppm 1.33 (t, J=6.9 Hz, 3 H), 3.62 (d, J=7.6 Hz, 2 H), 3.67 (t, J=8.0 Hz, 1 H), 3.68 (d, J=11.9 Hz, 1 H), 3.79 (d, J=8.0 Hz, 1 H), 3.83 (d, J=12.5 Hz, 1 H), 3.97 (q, J=6.9 Hz, 2 H), 4.16 (d, J=7.4 Hz, 1 H), 6.04 (s, 1 H), 6.80 (d, J=8.8 Hz, 2 H), 7.22 (d, J=8.6 Hz, 2 H), 7.29 (d, J=8.4 Hz, 1 H), 7.42 (dd, J=8.2, 2.0 Hz, 1 H), 7.93 (d, J=2.0 Hz, 1 H). HRMS calculated for C$_{22}$H$_{25}$O$_8$Cl (M) 452.1238. found 452.1237.

(9A-2): (25.9 mg, 24.4% yield); R$_t$=10.26 minutes; the fractions containing the product were concentrated under reduced pressure. The resulting material was precipitated from ethyl acetate and heptane. The resulting white solid was washed with heptane 2 times and dried under reduced pressure.

MS (LCMS) 497.2 (M+HCOO$^-$, negative mode)$^1$H NMR (400 MHz, METHANOL-d4) delta ppm 1.33 (t, J=6.9 Hz, 3 H), 3.56 (d, J=7.8 Hz, 1 H), 3.61 (d, J=7.2 Hz, 1 H), 3.66 (t, J=8.0 Hz, 1 H), 3.68 (d, J=12.8, 1 H), 3.79 (d, J=8.2 Hz, 1 H), 3.84 (d, J=12.5 Hz, 1 H), 3.97 (q, J=7.0 Hz, 2 H), 4.15 (d, J=7.4 Hz, 1 H), 6.05 (s, 1 H), 6.80 (d, J=8.4 Hz, 2 H), 7.21 (d, J=8.4 Hz, 2 H), 7.29 (d, J=8.4 Hz, 1 H), 7.41 (dd, J=8.2, 1.6 Hz, 1 H), 7.91 (d, J=1.6 Hz, 1 H). HRMS calculated for C$_{22}$H$_{25}$O$_8$Cl (M) 452.1238. found 452.1235.

Example 12

[2-Chloro-5-((1S,2S,3S,4R,5S)-2,3,4-trihydroxy-1-hydroxymethyl-6,8-dioxa-bicyclo[3.2.1]oct-5-yl)-phenyl]-(4-ethoxy-phenyl)-methanone

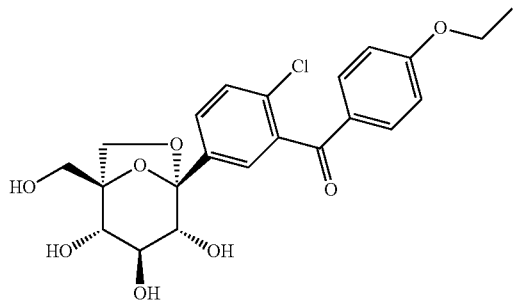 [SMILES: CCOc1ccc(C(=O)c2cc([C@]34OC[C@](CO)(O3)[C@@H](O)[C@H](O)[C@H]4O)ccc2Cl)cc1]

To a solution of acetic acid (1R,2S,3S,4R,5S)-3,4-diacetoxy-1-acetoxymethyl-5-[4-chloro-3-(4-ethoxy-benzoyl)-phenyl]-6,8-dioxa-bicyclo[3.2.1]oct-2-yl ester (see Example 11 for preparation; 65 mg, 0.10 mmol) in methanol (3 mL) and tetrahydrofuran (2 mL) was added sodium methoxide in methanol (25% wt) until pH 12 was obtained and the resulting mixture was stirred at room temperature. After 16 hours, the reaction mixture was neutralized by the addition of Dowex Monosphere 650C (H) cation exchange resin until the pH of the solution was <7, filtered and concentrated under reduced pressure. The resulting material was precipitated from ethyl acetate and heptanes and the resulting white solid was washed with heptane 2 times and dried under reduced pressure to yield the desired product (44.5 mg, 94% yield). MS (LCMS) 451.1 (M+H$^+$; positive mode)$^1$H NMR (400 MHz, METHANOL-d$_4$) delta ppm 1.40 (t, J=6.9 Hz, 3 H), 3.55 (d, J=8.0 Hz, 1 H), 3.60 (d, J=7.4 Hz, 1 H), 3.65 (t, J=8.1 Hz, 1 H), 3.67 (d, J=12.5 Hz, 1 H), 3.77 (d, J=8.0 Hz, 1 H), 3.83 (d, J=12.5 Hz, 1 H), 4.12 (q, J=7.0 Hz, 2 H), 4.14 (d, J=7.6 Hz, 1 H), 6.98 (d, J=8.8 Hz, 2 H), 7.48 (d, J=8.4 Hz, 1 H), 7.52 (d, J=2.0 Hz, 1 H), 7.65 (dd, J=8.4, 2.0 Hz, 1 H), 7.73 (d, J=8.8 Hz, 2 H). HRMS calculated for C$_{22}$H$_{23}$O$_8$Cl (M) 450.1081. found 450.1079.

Pharmacological Testing

The practice of the instant invention for the treatment of diseases modulated by the inhibition of SGLT2 can be evidenced by activity in at least one of the protocols described hereinbelow.

Biological Assays

In-Vitro Assay

The SGLT2 functional assay was designed to detect the inhibition of methyl-alpha-D glucopyranoside (AMG—a non-metabolizable form of glucose) uptake via the SGLT2 transporter. The SGLT2 transporter recovers glucose from the proximal tubules of the kidney; its inhibition results in sugar wasted in the urine. The positive control compound, Phlorizin, is a known inhibitor of glucose uptake for SGLT2 and was used for comparing the high percent effect of SGLT2 inhibition of the test compounds.

CHO-FlpIn (Invitrogen, Carlsbad, Calif.) cells stably expressing human SGLT2 (pcDNA5/FRT) were plated in Iso-TC 96 well plates (Perkin Elmer, Waltham, Mass.) at a density of 100,000 cells/well in 100 microL of growth media (1:1 F-12/DMEM media (Gibco, Carlsbad, Calif.), 10% FBS (Sigma, St. Louis Mo.), 1× Pen/Strep (Gibco, Carlsbad, Calif.), 600 microg/mL Hygromycin (Invitrogen, Carlsbad, Calif.)). Prior to treating with test compound, confluent cells were serum starved for 2 hours at 37° C. in 1:1 F-12/DMEM media, replacing with fresh F-12/DMEM media after 1 hour. Test compounds in dimethylsulfoxide (Sigma, St. Louis, Mo.) were diluted 100 fold in uptake buffer (140 mM NaCl (Promega, Madison, Wis.), 2 mM KCl (Teknova, Hollister, Calif.), 1 mM $CaCl_2$ (Teknova, Hollister, Calif.), 1 mM $MgCl_2$ (Teknova, Hollister, Calif.), and 10 mM HEPES (Gibco, Carlsbad, Calif.) to cell plates pre-rinsed with uptake buffer. Cells were pre-incubated with test compound for 15 minutes prior to the addition of 50 microL AMG (40 nCi AMG [U-$^{14}$C] (Perkin Elmer, Waltham, Mass.) in unlabelled AMG (Aldrich, St. Louis, Mo.)) per well yielding a final concentration of 11.33 microM AMG.** Cell plates were then incubated for 3 hours at 37° C. for AMG uptake. After incubation, cells were washed twice with ice cold wash buffer (uptake buffer containing 200 microM Phlorizin (Sigma), air dried and lysed in 30 microL of 200 mM NaOH and 1% SDS buffer on an orbital shaker. Microscint 40 (Perkin Elmer, Waltham, Mass.) was added to the lysed cells (giving a final volume of 200 microL) and mixed by orbital shaking for 30 minutes. Plates were stored in the dark overnight and quantitated in the 1540 Microbeta Trilux (Wallac, Waltham, Mass.) using a normalized protocol for $^{14}$C detection. The percent effect of test compounds to inhibit AMG uptake was calculated using the following calculation:

[% Effect=((ZPE−T)/(ZPE−HPE))×100%]

where "ZPE" is the corrected counts per minute (CCPM) in control wells containing 0.5% DMSO, "T" is the CCPM in wells containing test compound at various concentrations of the standard curve, and "HPE" is the high percent effect referring to the CCPM in control wells containing 10 microM Phlorizin. The $IC_{50}$ values were calculated using a dose response equation and are summarized for the compounds tested in Table 1.

** For test compound 1, cells were pre-incubated with test compound 1 for 15 minutes prior to the addition of the appropriate amount of AMG (40 nCi AMG [U-$^{14}$C] (Perkin Elmer, Waltham, Mass.) in unlabelled AMG (Aldrich, St. Louis, Mo.)) per well yielding a final concentration of 200 microM AMG.

Abbreviations used in the in vitro testing description include:
SGLT2 Type 2 sodium/glucose co-transporter
AMG methyl-α-D Glucopyranoside
DMEM Dulbecco's Modified Eagle's Medium
IC50 50% Inhibition Concentration
FBS Fetal Bovine Serum
DMSO Dimethylsulfoxide
SDS Sodium Dodecyl Sulfate
CHO-FlpIn Chinese Hamster Ovary cell containing the FRT site

TABLE 1

| Test Compound | Run No. | hSGLT1 $IC_{50}$ nM | hSGLT2 $IC_{50}$ nM |
|---|---|---|---|
| 1 | 1 | Not tested | 2.6** |
| 2 | 1 | 10,000 | 1090 |
|   | 2 | 10,000 | 1770 |
| 3 | 1 | 3470 | 5 |
|   | 2 | 5830 | 6.7 |
| 4 | 1 | 3360 | 45.9 |
| 8 | 1 | 1968 | 4 |
|   | 2 | 1895 | 3 |
|   | 3 | 1997 | 4 |

Throughout this application, various publications are referenced. The disclosures of these publications in their entireties are hereby incorporated by reference into this application for all purposes.

It will be apparent to those skilled in the art that various modifications and variations can be made in this invention without departing from the scope or spirit of the invention. Other embodiments of the invention will be apparent to those skilled in the art from consideration of the specification and practice of the invention disclosed herein. It is intended that the specification including the examples be considered as exemplary only, with a true scope and spirit of the invention being indicated by the following claims.

What is claimed is:

1. A method for treating obesity in humans comprising the step of administering to a human in need of such treatment a therapeutically effective amount of a pharmaceutical composition comprising: (i) (1S,2S,3S,4R,5S)-5-[-4-chloro-3-(4-ethoxy-benzyl)-phenyl]-1-hydroxymethyl-6,8-dioxa-bicyclo[3.2.1]octane-2,3,4-triol; (ii) a pharmaceutically acceptable excipient, diluent, or carrier and (iii) sitagliptin; or a pharmaceutically acceptable salt thereof.

2. A method for treating Type 2 diabetes in humans comprising the step of administering to a human in need of such treatment a therapeutically effective amount of a pharmaceutical composition comprising: (i) (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol; (ii) a pharmaceutically acceptable excipient, diluent, or carrier and (iii) sitagliptin; or a pharmaceutically acceptable salt thereof.

* * * * *